United States Patent [19]

Woodard et al.

[11] Patent Number: 5,496,956
[45] Date of Patent: Mar. 5, 1996

[54] HERBICIDAL SUBSTITUTED ARYL-HALOALKYLPYRAZOLES

[75] Inventors: Scott S. Woodard, Ballwin; Bruce C. Hamper, Kirkwood; Kurt Moedritzer, Webster Groves; Michael D. Rogers, Maryland Heights; Deborah A. Mischke, Defiance; Gerard A. Dutra, St. Louis, all of Mo.

[73] Assignee: Monsanto Company, St. Louis, Mo.

[21] Appl. No.: 416,570

[22] Filed: Apr. 4, 1995

Related U.S. Application Data

[62] Division of Ser. No. 144,384, Nov. 2, 1993, which is a division of Ser. No. 763,762, Sep. 25, 1991, Pat. No. 5,281,571, which is a continuation-in-part of Ser. No. 600,031, Oct. 18, 1990, abandoned.

[51] Int. Cl.$^6$ .................................................. C07D 231/10
[52] U.S. Cl. ............................................................ 548/377.1
[58] Field of Search ................................................. 548/377.1

[56] References Cited

PUBLICATIONS

CA 117:69859p Preparation of . . . –pyrazoles. Dutra et al., p. 802, 1992.

*Primary Examiner*—Joseph K. McKane
*Attorney, Agent, or Firm*—Joan Thierstein; Grace L. Bonner; Richard H. Shear

[57] ABSTRACT

The invention herein relates to certain substituted-arylpyrazole compounds, herbicidal compositions containing same, herbicidal methods of use and processes for preparing said compounds.

3 Claims, No Drawings

HERBICIDAL SUBSTITUTED ARYL-HALOALKYLPYRAZOLES

This is a Divisional of application Ser. No. 08/144,384, filed on Nov. 2, 1993, now pending, which is a divisional of Ser. No. 07/763,762, filed on Sep. 25, 1991, now U.S. Pat. No. 5,281,571, which is a continuation-in-part of Ser. No. 07/600,031, filed on Oct. 18, 1990, now abandoned.

FIELD OF THE INVENTION

The field of the invention contemplated herein pertains to herbicidal compounds generically defined by the above title, to compositions containing same and processes for preparing said compounds.

BACKGROUND OF THE INVENTION

Various substituted 3-aryl- and 5-arylpyrazole type compounds are known in the literature. Such compounds have various utilities, e.g., as chemical intermediates, pharmaceuticals and herbicides.

Among the substituted 3-aryl-5-(halo)alkylpyrazoles and 5-aryl-3-(halo)alkylpyrazoles in the art are those having a variety of substituent radicals on the aryl and/or pyrazole moieties of the compound, e.g., alkyl, carboxyl, alkoxycarbonyl, formyl, phenyl and phenyl substituted with various groups such as alkyl, halo or nitro groups, etc. For example, compounds of this type are known wherein the aryl moiety is a substituted or unsubstituted phenyl radical, in which the substituent radicals are alkyl, cycloalkyl, alkaryl, halogen, trifluoromethyl, etc., and the pyrazolyl radical is substituted in various positions on the nitrogen or carbon atoms with alkyl, halogen, alkoxy, hetero-cycles, $S(O)_nR$ members, wherein n is 0–2 and R may be a variety of radicals such as those substituted on the aryl or pyrazole moieties.

Compounds of the above type having utility as herbicides, typically require application rates as high as five or ten or more kilograms per hectare to achieve adequate weed control. Accordingly, it is an object of this invention to provide a novel class of arylpyrazole-type compounds having uniquely high phytotoxic unit activity against a spectrum of weeds, including narrow-leaf and broadleaf weeds yet maintain a high degree of safety in a plurality of crops, especially small grains and/or row crops such as wheat, barley, corn, soybeans, peanuts, etc.

The 1-(halo)alkyl-3-(substituted)aryl-4-halo-5-haloalkylpyrazoles and 1-(halo)alkyl-5-(substituted)aryl-4-halo-3-haloalkylpyrazoles described herein are new.

SUMMARY OF THE INVENTION

This invention relates to herbicidally-active compounds, compositions containing these compounds, processes for making them and herbicidal methods of using the same.

The herbicidal compounds of this invention are characterized by the structure of Formula I

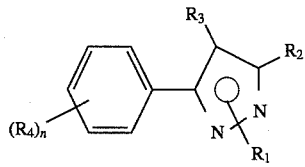

and agriculturally-acceptable salts and hydrates thereof wherein $R_1$ is independently $C_{1-8}$ alkyl; $C_{3-8}$ cycloalkyl, cycloalkenyl, cycloalkylalkyl, or cycloalkenylalkyl; $C_{2-8}$ alkenyl or alkynyl; benzyl; wherein the above members may be optionally substituted with halogen, amino, nitro, cyano, hydroxy, alkoxy, alkylthio,

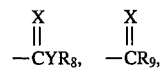

$YR_{10}$, or $NR_{11}R_{12}$;

$R_2$ is $C_{1-5}$ haloalkyl;

$R_3$ is halogen;

$R_4$ is an $R_1$ member, thioalkyl, alkoxyalkyl or polyalkoxyalkyl, carbamyl, halogen, amino, nitro, cyano, hydroxy, $C_{1-10}$ heterocycle containing 1–4 O, $S(O)_m$ and/or $NR_{18}$ hetero atoms, $C_{6-12}$ aryl, aralkyl or alkaryl,

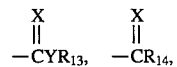

$YR_{15}$ or $NR_{16}R_{17}$ group. Any two $R_4$ groups may be combined through a saturated and/or unsaturated carbon, —(C=X)—, and/or hetero O, $S(O)_m$ and/or $NR_{18}$ linkage to form a cyclic ring having up to 9 ring members which may be substituted with any of the $R_4$ members;

X is O, $S(O)_m$, $NR_{19}$ or $CR_{20}R_{21}$;

Y is O, $S(O)_m$ or $NR_{22}$;

$R_{8-22}$ are hydrogen or one of the $R_4$ members;

m is 0–2 and n is 1–5.

A preferred subgenus of the substituted-arylpyrazolyl compounds in this invention are those according to Formula II

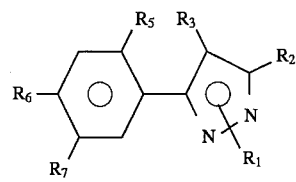

and agriculturally-acceptable salts and hydrates thereof wherein $R_1$ is $C_{1-5}$ alkyl, alkylthio, alkoxyalkyl, $C_{2-4}$ alkenyl, benzyl, which members may optionally be substituted with halogen, amino, nitro, cyano, hydroxy

groups;

$R_2$, $R_3$, X, Y and $R_8$ are as defined for Formula I;

$R_5$ is halogen or hydrogen;

$R_6$ and $R_7$ are as defined for the $R_4$ member of Formula I.

Particularly preferred compounds of this invention are those according to Formula III

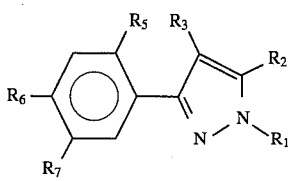

and agriculturally-acceptable salts and hydrates thereof wherein $R_1$ is $C_{1-5}$ alkyl;

$R_2$, $R_3$ and $R_5$ are as previously defined;

$R_6$ is halogen, nitro, cyano, $YR_{10}$;

$R_7$ is hydrogen or an $R_4$ member and $R_6$ and $R_7$ are combined through a saturated and/or unsaturated carbon, —(C=X)—, and/or hetero O, $S(O)_m$ and/or $NR_{18}$ linkage to form a cyclic ring having up to 9 ring members which may be substituted with any of the $R_4$ members, provided that when said linkage contains

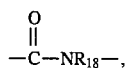

said cyclic ring has at least six ring members and

X, Y, $R_{18}$ and m are as previously defined.

Still more preferred are compounds according to Formula III and agriculturally-acceptable salts and hydrates thereof wherein $R_1$ is methyl;

$R_2$ is $CF_3$, $CF_2Cl$ or $CF_2H$;

$R_3$ is chloro or bromo;

$R_5$ is fluoro;

$R_6$ is chloro;

$R_7$ is propargyloxy, allyloxy, polyalkoxy, $OCH(R_{23})COR_{24}$ where $R_{23}$ is hydrogen, methyl or ethyl and $R_{24}$ is $YR_{10}$ or $NR_{11}R_{12}$;

$R_6$ and $R_7$ are combined through an $-OCH_2(C=O)N(R_{18})-$ linkage to give a fused six member ring and Y, $R_{10}$–$R_{12}$ and $R_{18}$ are as previously defined.

Preferred species according to this invention include the following:

4-Chloro-3-(4-chloro-2-fluoro-5-propargyloxyphenyl)-1-methyl-5-(trifluoromethyl)-1H-pyrazole, 2-(2-Chloro-5-(4-chloro-1-methyl-5-(trifluoromethyl)-1H-pyrazol-3-yl)-4-fluorophenoxy)propanoic acid, ethyl ester, (2-Chloro-5-(4-chloro-1-methyl-5-(trifluoromethyl)-1H-pyrazol-3-yl)-4-fluorophenoxy) acetic acid, 1-methylethyl ester, 4-Chloro-3-(4-chloro-2-fluoro-5-(methoxymethoxy)phenyl)-1-methyl-5-(trifluoromethyl)-1H-pyrazole, 4-Chloro-3-(4-chloro-2-fluoro-5-(methoxyethoxy)phenyl)-1-methyl-5-(trifluoromethyl)-1H-pyrazole, (2-Chloro-5-(4-chloro-1-methyl-5-(trifluoromethyl)-1H-pyrazol-3-yl)-4-fluorophenoxy)acetic acid, 1,1-dimethylethyl ester, (2-Chloro-5-(4-chloro-1-methyl-5-(trifluoromethyl)-1H-pyrazol-3-yl)-4- fluorophenoxy)acetic acid, 2-Chloro-5-(4-chloro-1-methyl-5-(trifluoromethyl)-1H-pyrazol-3-yl)-4-fluorobenzoic acid, 2-ethoxy-1-methyl-2-oxoethyl ester, 2-Chloro-5-(4-chloro-1-methyl-5-(trifluoromethyl)-1H-pyrazol-3-yl)-4-fluorobenzoic acid, 2-methoxy-1-methyl-2-oxoethyl ester, 2-Chloro-5-(4-chloro-1-methyl-5-(trifluoromethyl)-1H-pyrazol-3-yl)-4-fluorobenzoic acid, ethyl ester, 2-Chloro-5-(4-chloro-1-methyl-5-(trifluoromethyl)-1H-pyrazol-3-yl)-4-fluorobenzoic acid, 1-methylethyl ester and 6-(4-Chloro-1-methyl-5-(trifluoromethyl)-1H-pyrazol-3-yl)-7-fluoro-4-(2-propynyl)-2H-1,4-benzoxazin-3-(4H)-one.

While all of the above compounds have exhibited particularly efficacious use in a plurality of crops, tests to date indicate that those of most preferred interest are the Compound Nos. 135, 137, 261, 282 and 446. These compounds collectively provide outstanding control of resistant broadleaf weeds such as pigweed, cocklebur, velvetleaf and hemp sesbania in various crops such as corn, soybean and nuts and in forestry against trees and vines. Other of the compounds of this invention exhibit excellent herbicidal effect against weeds in other crops such as wheat and barley.

Some of the compounds of the present invention may have more than one possible stereoisomer and these stereoisomers may differ in herbicidal efficacy. The structures illustrated are intended to include all possible stereoisomers.

The above compounds may be suitably applied in a variety of application modes, e.g., pre-emergent and/or postemergent, surface applied, pre-plant incorporated, etc.

Another aspect of this invention relates to processes for preparing the compounds according to Formulae I–III and their precursors, intermediates and/or starting materials. These process aspects will be discussed in more detail below.

Other aspects of this invention relate to herbicidal compositions containing the compounds of Formulae I–III and to herbicidal methods of using those compositions to control undesirable weeds.

It is further within the purview of this invention that the substituted-arylpyrazole compounds of Formulae I–III be formulated in compositions containing other herbicidal compounds as co-herbicides, e.g., acetamides, esp., acetanilides, thiocarbamates, ureas, sulfonylureas, sulfonamides, imidazolinones, benzoic acid and its derivatives, diphenyl ethers, salts of glyphosate, etc.

Other additaments may be included in such herbicidal formulations as desired and appropriate, e.g, antidotes (safeners) for the herbicide(s), plant disease control agents, such as fungicides, insecticides, nematicides and other pesticides.

As used herein, the terms "alkyl", "alkenyl", alkynyl" when used either alone or in compound form, e.g., haloalkyl, haloalkenyl, alkoxy, alkoxyalkyl, etc., are intended to embrace linear or branched-chain members. Preferred alkyl members are the lower alkyls having from 1 to 4 carbon atoms and preferred alkenyl and alkynyl members are those having from 2 to 4 carbon atoms.

The term "haloalkyl" is intended to mean alkyl radicals substituted with one or more halogen (chloro, bromo, iodo or fluoro) atoms; preferred members of this class are those having from 1 to 4 carbon atoms, especially the halomethyl radicals, e.g., trifluoromethyl. In polyhaloalkyl members, the halogens can all be the same or mixed halogens.

Representative, non-limiting alkyl, alkenyl, alkynyl, cycloalkyl, cycloalkylalkyl, cycloalkenyl and cycloalkenylalkyl members include the following:

Methyl, ethyl, the isomeric propyls, butyls, pentyls, hexyls, heptyls, octyls, nonyls, decyls, etc.; vinyl, allyl, crotyl, methallyl, the isomeric butenyls, pentenyls, hexenyls, heptenyls, octenyls; ethynyl, the isomeric propynyls, butynyls, pentynyls, hexynyls, etc.; the alkoxy, polyalkoxy, alkoxyalkyl and polyalkoxyalkyl analogs of the foregoing alkyl groups, e.g., methoxy, ethoxy, propoxys, butoxys, pentoxys and hexoxys and corresponding polyalkoxys and alkoxyalkyls, e.g., methoxymethoxy, methoxyethoxy, ethoxymethoxy, ethoxyethoxy, methoxymethyl, methoxyethyl, ethoxymethyl, ethoxyethyl, propoxymethyl, isopropoxymethyl, butoxymethyl, isobutoxymethyl, tertbutoxymethyl, pentoxymethyl, hexoxymethyl, etc., cyclopropyl, cyclobutyl, cyclopentyl, cyclohexyl, cycloheptyl, cyclopropylmethyl, cyclobutylmethyl, cyclopentylmethyl, etc.; the isomeric cyclopentenes, cyclohexenes and cycloheptenes having mono- or di-unsaturation; representative aryl, aralkyl and alkaryl groups include phenyl, the isomeric tolyls and xylyls, benzyl, naphthyl, etc.

Representative mono-, di- and tri- haloalkyl members include: chloromethyl, chloroethyl, bromomethyl, bromoethyl, iodomethyl, iodoethyl, chloropropyl, bromopropyl, iodopropyl, 1,1-dichloromethyl, 1,1-dibromomethyl, 1,1-dichloropropyl, 1,2-dibromopropyl, 2,3-dibromopropyl, 1-chloro-2-bromoethyl, 2-chloro-3-bromopropyl, trifluoromethyl, trichloromethyl, etc.

Representative heterocyclic members include: alkylthiodiazolyl; piperidyl; piperidylalkyl; dioxolanylalkyl; thiazolyl; alkylthiazolyl; benzothiazolyl; halobenzothiazolyl; furyl; alkyl-substituted furyl; furylalkyl; pyridyl; alkylpyridyl; alkyloxazolyl; tetrahydrofurylalkyl; 3-cyanothienyl; thienylalkyl; alkyl-substituted thienyl; 4,5-polyalkylenethienyl; piperidinyl; alkylpiperidinyl; pyridyl; di- or tetrahydropyridinyl; alkyltetrahydromorpholyl; alkylmorpholyl; azabicyclononyl; diazabicycloalkanyl, benzoalkylpyrrolidinyl; oxazolidinyl; perhydrooxazolidinyl; alkyloxazolidyl; furyloxazolidinyl, thienyloxazolidinyl, pyridyloxazolidinyl, pyrimidinyloxazolidinyl, benzooxazolidinyl, $C_{3-7}$ spirocycloalkyloxazolidinyl, alkylaminoalkenyl; alkylideneimino; pyrrolidinyl; piperidonyl; perhydroazepinyl; perhydroazocinyl; pyrazolyl; dihydropyrazolyl; piperazinyl; perhydro-1, 4-diazepinyl; quinolinyl, isoquinolinyl; di-, tetra- and perhydroquinolyl- or -isoquinolyl; indolyl and di- and perhydroindolyl and said heterocyclic members substituted with radicals such as defined in Formulae I–III.

By "agriculturally-acceptable salts" of the compounds defined by the above formulae is meant a salt or salts which readily ionize in aqueous media to form a cation or anion of said compounds and the corresponding salt anion or cation, which salts have no deleterious effect on the herbicidal properties of a given herbicide and which permit formulation of various mixtures, e.g., herbicide-antidote compositions without undue problems of mixing, suspension, stability, applicator equipment use, packaging, etc.

By "herbicidally-effective" is meant the amount of herbicide required to effect a meaningful injury or destruction to a significant portion of affected undesirable plants or weeds. Although of no hard and fast rule, it is desirable from a commercial viewpoint that 80–85% or more of the weeds be destroyed, although commercially significant suppression of weed growth can occur at much lower levels, particularly with some very noxious, herbicide-resistant plants.

DETAILED DESCRIPTION OF THE INVENTION

The compounds according to this invention are suitably prepared by a variety of processes as will be described below.

In broad aspect, the preferred overall process for preparing the compounds of Formulae I–III is best viewed in the separate process steps required to get the necessary intermediates, immediate precursors and end products of the above formulae. The products of "Process I" provide the intermediates necessary for "Processes II–XVI". The products according to Formulae I–III are prepared by either a single process "II–XVI" or any combination of "Processes II–XVI". It is expressly understood that various modifications obvious to those skilled in the art are contemplated. Specific embodiments are described in Examples 1–42 below.

In the sequence of process steps described below, the various symbols defining radical substituents, e.g., $R_1$–$R_{24}$, X, Y, etc. have the same meanings as defined for the compounds of Formulae I–III, unless otherwise qualified or limited.

Process I

This process describes the preparation of important intermediate compounds of Formula B, or isomeric mixtures thereof, which are useful in the overall process scheme for producing compounds of Formulae I–III.

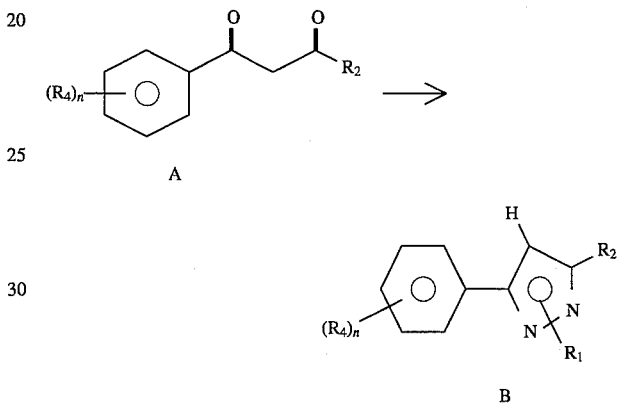

The process for the preparation of a compound of Formula B suitably proceeds from compounds of Formula A. Compounds of Formula A are prepared by known means from substituted acetophenones, which also are known in the art; the structure shown for Formula A is meant to embody all possible tautomeric forms or mixtures thereof. Compounds of Formula A can be prepared in any anhydrous solvent or mixture of solvents; the preferred solvents are ether, alcohols, dimethylsulfoxide, toluene, benzene, etc., by reacting a substituted acetophenone in the presence of an ester with a strong base such as an alkali alkoxide, alkali amide or alkali hydride with alkali alkoxides such as sodium methoxide being preferred. Reaction temperature is in the range of –100° C. to 200° C., preferably –78° C. to 50° C. The reaction period may be chosen from the range of a few minutes to several weeks depending on the amounts of reagents, reaction temperature, etc. After completion of the reaction, the compound of Formula A is isolated by diluting the reaction mixture with water, which may be followed by acidification of the aqueous layer or, alternatively, by diluting the reaction mixture with aqueous acid. Subsequently, the product is isolated by a method such as crystallization or solvent extraction. If necessary, the product is purified by standard methods. The cyclization of this intermediate to give compounds of Formula B can be carried out in any suitable solvent by treatment with hydrazine or substituted hydrazines with alkylhydrazines being preferred. Reaction temperature is in the range of –78° C. to 200° C., preferably 10° C. to 120° C. The reaction period may be chosen from the range of a few minutes to several weeks depending on the amounts of reagents, reaction temperature, etc. The product is isolated after completion of the reaction by filtration and/or concentration of the reaction mixture. If necessary, the product is purified by standard methods such as extraction, crystallization, column chromatography, etc.

In the case of the addition of hydrazine to compounds of Formula A, the resultant pyrazole of Formula C may be treated with an alkylating agent to obtain compounds of Formula B. In this case, products of Formula B can be obtained by treatment of the above compound with an alkylating agent such as methyl iodide, benzyl bromide, allyl bromide, dimethylsulfate, etc. The preferred solvents are toluene, dimethylsulfoxide, acetone, dimethylformamide, dioxane, etc. The reaction may be carried out with or without a base. In cases in which a base is employed, alkali metal carbonates or hydroxides such as sodium carbonate or sodium hydroxide may be used. Reaction temperature is in the range of −78° C. to 200° C., preferably 10° C. to 120° C. The reaction period may be chosen from the range of a few minutes to several weeks depending on the amounts of reagents, reaction temperature, etc. The product is isolated after completion of the reaction by filtration and/or concentration of the reaction mixture. If necessary, the product is purified by standard methods such as extraction, crystallization, column chromatography, etc.

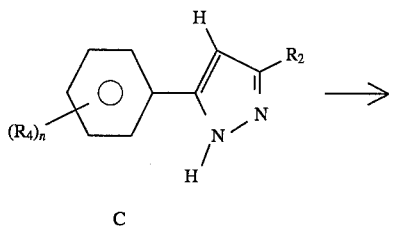

C

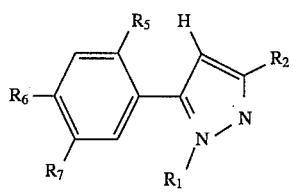

B

Compounds illustrated by Formula C can exist in two possible tautomeric forms, either a 5-arylpyrazole or a 3-arylpyrazole. The 5-arylpyrazole depicted in Formula C is meant to include both possible tautomeric forms. Table 1 shows typical examples of compounds of Formula C.

In all tables herein, boiling points and melting points are measured in degrees Centigrade (° C) and unless otherwise indicated refractive indices are at 25° C.

TABLE 1

PHYSICAL DATA FOR 1-H-5-ARYLPYRAZOLES

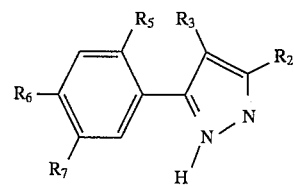

| Compound No. | $R_2$ | $R_3$ | $R_5$ | $R_6$ | $R_7$ | physical data (mp, °C.) |
|---|---|---|---|---|---|---|
| 1 | $CF_3$ | H | H | F | H | 114.5–116.5 |
| 2 | $CF_3$ | H | Cl | F | H | 116.5–117.5 |
| 3 | $CF_2Cl$ | H | F | Cl | $OCH_3$ | 177.0 |
| 4 | $CF_2CF_3$ | H | F | Cl | $OCH_3$ | 135.0 |
| 5 | $CF_3$ | H | F | H | F | 156.0–157.0 |
| 6 | $CF_3$ | H | F | F | H | 157.0–158.0 |
| 7 | $CF_3$ | H | H | Cl | H | 150.0–151.0 |
| 8 | $CF_2Cl$ | H | H | Cl | H | 148.5–150.0 |
| 9 | $CF_3$ | H | F | Cl | $OCH_3$ | 209.0–210.0 |
| 10* | $CF_3$ | Cl | F | Cl | $OCH_3$ | 186.0 |
| 11 | $CF_3$ | H | F | Cl | H | 152.0–154.0 |
| 12 | $CF_2H$ | H | F | H | F | 146.0 |
| 13 | $CF_3$ | H | F | Cl | $CH_3$ | 159.0–160.0 |
| 14 | $CF_3$ | H | F | $OCH_3$ | H | 138.0 |

*Compound No. 10 was prepared from Compound No. 9 by Process II.

The 2-fluoro-4-chloro-5-methoxyacetophenone, used to prepare compound Nos. 3, 4 and 9 by the above process, was prepared from 2-chloro-4-fluoroanisole, which can be obtained from 2-chloro-4-fluorophenol by methods known in the art (C. A. Buehler and D. E. Pearson, Survey of Organic Synthesis, pages 285–382, Wiley-Interscience, New York, 1970). Treatment of 2-chloro-4-fluoroanisole with titanium tetrachloride and dichloromethylmethylether at room temperature gives 2-fluoro-4-chloro-5-methoxybenzaldehyde. The 2-fluoro-4-chloro-5-methoxybenzaldehyde is converted to 2-fluoro-4-chloro-5-methoxyacetophenone by treatment with methyl Grignard followed by oxidation using standard methods known in the art.

The above mentioned 2-fluoro-4-chloro-5-methoxyacetophenone and its analogous precursor, 2-fluoro-4-chloro-5-methoxybenzaldehyde and processes for preparing them are the discovery of other inventors (Bruce C. Hamper and Kindrick L. Leschinsky) employed by the assignee herein.

Tables 2 and 3 show typical examples of compounds prepared by Process I.

TABLE 2

PHYSICAL DATA FOR 1-ALKYL-5-ARYLPYRAZOLES

| Compound No. | $R_1$ | $R^2$ | $R^5$ | $R^6$ | $R^7$ | physical data (mp; nD) |
|---|---|---|---|---|---|---|
| 15 | $CH_3$ | $CF_3$ | Cl | Cl | H | 85.0° C. |
| 16 | $CH(CH_3)_2$ | $CF_3$ | F | Cl | $OCH_3$ | 75.0° C. |
| 17 | $CF_2H$ | $CF_3$ | F | Cl | $OCH_3$ | 76.0° C. |

TABLE 2-continued

PHYSICAL DATA FOR 1-ALKYL-5-ARYLPYRAZOLES

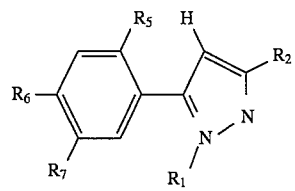

| Compound No. | $R_1$ | $R^2$ | $R^5$ | $R^6$ | $R^7$ | physical data (mp; nD) |
|---|---|---|---|---|---|---|
| 18 | $CH_3$ | $CF_3$ | H | $NO_2$ | H | 116.5–121.0° C. |
| 19 | $CH_3$ | $CF_3$ | H | $NO_2$ | $OCH_3$ | 105.0–107.0° C. |
| 20 | $CH_3$ | $CF_3$ | F | H | F | 38.0–39.0° C. |
| 21 | $CH_3$ | $CF_3$ | F | F | H | 37.0–38.0° C. |
| 22 | $CH_3$ | $CF_3$ | H | Cl | H | 26.6–28.3° C. |
| 23 | $CH_3$ | $CF_2Cl$ | H | Cl | H | 31.0–32.0° C. |
| 24 | $CH_3$ | $CF_3$ | F | Cl | $OCH_3$ | 119.5° C. |
| 25 | $CH_2CH_3$ | $CF_3$ | F | Cl | $OCH_3$ | 84.0° C. |
| 26 | $CH_2CO_2CH_3$ | $CF_3$ | F | Cl | $OCH_3$ | 98.5° C. |
| 27 | $CH_3$ | $CF_3$ | H | $OCH_3$ | $NO_2$ | 140.0° C. |
| 28 | $CH_3$ | $CF_3$ | Cl | Cl | F | nD; 1.5221 (25° C.) |
| 29 | $CH_3$ | $CF_3$ | F | Cl | H | 70.0–72.0° C. |
| 30 | $CH_3$ | $CF_2H$ | F | H | F | 83.0° C. |
| 31 | n-butyl | $CF_3$ | F | Cl | $OCH_3$ | nD; 1.5068 (25° C.) |
| 32 | n-propyl | $CF_3$ | F | Cl | $OCH_3$ | 78.0° C. |
| 33 | benzyl | $CF_3$ | F | Cl | $OCH_3$ | viscous oil |
| 34 | allyl | $CF_3$ | F | Cl | $OCH_3$ | 58.0° C. |
| 35 | $CH_3$ | $CF_3$ | F | Cl | $CH_3$ | 50.0–52.0° C. |

TABLE 3

PHYSICAL DATA FOR 1-ALKYL-3-ARYLPYRAZOLES

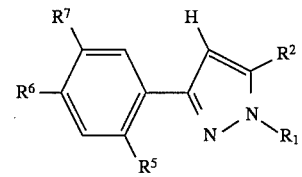

| Compound No. | $R_1$ | $R^2$ | $R^5$ | $R^6$ | $R^7$ | physical data (mp, nD) |
|---|---|---|---|---|---|---|
| 36 | $CH_3$ | $CF_3$ | Cl | Cl | H | 45.0° C. |
| 37 | $CH_3$ | $CF_3$ | F | $OCH_3$ | H | nD 1.5139 (25° C.) |
| 38 | $CH_3$ | $CF_3$ | Cl | F | H | clear oil |
| 39 | $CH_3$ | $CF_3$ | H | $NO_2$ | H | 101.0–103.0° C. |
| 40 | $CH_3$ | $CF_3$ | F | H | F | nD 1.4925 (25° C.) |
| 41 | $CH_3$ | $CF_3$ | F | Cl | $OCH_3$ | 121.0° C. |
| 42 | $CH_3$ | $CF_3$ | F | F | H | 51° C. |
| 43 | $CH_3$ | $CF_3$ | H | Cl | H | 55.5–57.5° C. |
| 44 | $CH_3$ | $CF_2Cl$ | H | Cl | H | 39.3–40.1° C. |
| 45 | Et | $CF_3$ | F | Cl | $OCH_3$ | 73.5° C. |
| 46 | $CH_3$ | $CF_3$ | H | $OCH_3$ | $NO_2$ | 133.0° C. |
| 47 | $CH_3$ | $CF_3$ | Cl | Cl | F | 35.0–38.0° C. |
| 48 | $CH_3$ | $CF_3$ | F | Cl | H | 45.0–47.0° C |
| 49 | $CH_3$ | $CF_2H$ | F | H | F | 48.0–49.0° C. |
| 50 | $CH_3$ | $CF_3$ | F | Cl | $CH_3$ | 48.0–49.0° C. |
| 51 | $CH_2CO_2CH_3$ | $CF_3$ | F | Cl | $OCH_3$ | 116.5° C. |
| 52 | n-butyl | $CF_3$ | F | Cl | $OCH_3$ | 42.0° C. |
| 53 | n-propyl | $CF_3$ | F | Cl | $OCH_3$ | 72.0° C. |
| 54 | $CH(CH_3)_2$ | $CF_3$ | F | Cl | $OCH_3$ | 69.5° C. |
| 55 | $CF_2H$ | $CF_3$ | F | Cl | $OCH_3$ | 116.5° C. |
| 56 | benzyl | $CF_3$ | F | Cl | $OCH_3$ | 69.0° C. |
| 57 | allyl | $CF_3$ | F | Cl | $OCH_3$ | 55.0° C. |
| 58 | $CH_3$ | $CF_2H$ | F | Cl | $CH_3$ | 42.0–43.0° C. |
| 59 | $CH_3$ | $CF_2CF_3$ | F | Cl | $OCH_3$ | 84.0–85.0° C. |
| 60 | $CH_3$ | $CF_2Cl$ | F | Cl | $OCH_3$ | 73.0–74.0° C. |
| 61 | $CH_3$ | $CF_3$ | H | F | H | clear oil |

Process II

In this process description, one class of products according to Formula I wherein $R_3$ is halogen is prepared by the halogenation of the corresponding compound of Formula B. In this process, $R_1$ can be as previously defined and further include hydrogen.

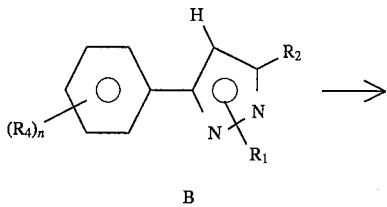

B

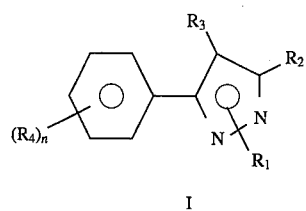

I

Any inert solvent may be used in this reaction that does not markedly hinder the reaction from proceeding or the reaction may be carried out neat. Such solvents include, but are not limited to, organic acids, inorganic acids, hydrocarbons, halogenated hydrocarbons, aromatic hydrocarbons, ethers and sulfides, sulfoxides or sulfones. Halogenating agents suitable for the above reaction include bromine, chlorine, N-bromosuccinimide, N-chlorosuccinimide, sulfuryl chloride, etc. With some halogenating agents it is preferable to use an organic peroxide or light as a catalyst. The amount of halogenating agent can range from less than one molar equivalent to an excess. Reaction temperature is in the range of −100° C. to 200° C., preferably 10° C. to 100° C. The reaction period may be chosen from the range of a few minutes to several weeks depending on the amounts of reagents, reaction temperature, etc. After completion of the reaction the product is isolated by diluting the reaction mixture with water and the product is isolated by a method such as crystallization or solvent extraction. If necessary, the product is purified by standard methods.

Process III

This section describes a process for the preparation of compounds according to Formula D (a Formula I compound in which one of the $R_4$ residues is a nitro group) starting with compounds according to Formula I.

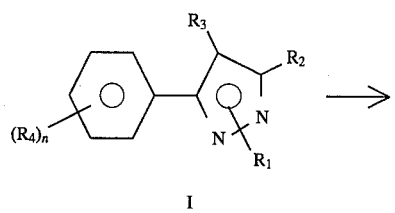

I

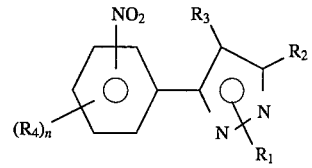

D

Nitrating agents such as concentrated nitric acid, fuming nitric acid, mixtures of nitric acid with concentrated sulfuric acid, alkyl nitrates and acetyl nitrate are suitable for this reaction. Solvents such as mineral acids, organic acids, organic solvents, such as acetic anhydride or methylene chloride, and water or mixtures of these solvents may be used. The nitrating agent may be used in equimolar amounts or in excess. Reaction temperature is in the range of −100° C. to 200° C., preferably −10° C. to 100° C. The reaction period may be chosen from the range of a few minutes to several days depending on the amounts of reagents, reaction temperature, etc. After completion of the reaction the product is isolated by diluting the reaction mixture with water and the product is isolated by methods such as crystallization or solvent extraction. If necessary, the product is purified by standard methods.

Process IV

In this process description, one class of products according to Formula F (one species of Formula II compounds) is prepared by displacement of the Z radical of the corresponding compound of Formula E, wherein Z is any suitable leaving group of the previously defined $R_4$ members.

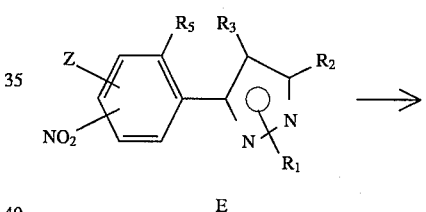

E

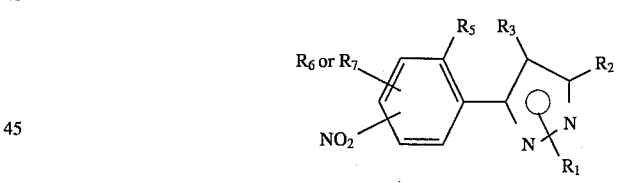

F

Formation of products of Formula F can be carried out by treatment of compounds of Formula E with an alkoxide, thioalkoxide, amine, etc., or an alcohol, mercaptan, amine, etc., in the presence of a base in any suitable solvent or mixture of solvents. The preferred solvents are dimethylsulfoxide, acetone, dimethylformamide, dioxane, water, etc. or mixtures of solvents including two phase mixtures (such as water and methylene chloride or other organic solvent). The base may be an organic base (such as a trialkylamine or another organic amine) or an inorganic base (an alkali carbonate such as potassium carbonate or sodium carbonate or an alkali metal hydroxide such as sodium hydroxide). In the case of two immiscible liquid phases, it may be advantageous to add a phase transfer catalyst such as a benzyltrialkylammonium halide or other ammonium salt. Reaction temperature is in the range of −100° C. to 200° C., preferably −10° C. to 100° C. The reaction period may be chosen from the range of a few minutes to several weeks depending on the amounts of reagents, reaction temperature, etc. The product is isolated after completion of the reaction by filtration and/or concentration of the reaction mixture. If necessary, the product is purified by standard methods such as extraction, crystallization, column chromatography, etc.

Process V

In this process description, compounds of Formula I are prepared from compounds of Formula G (Formula I compounds in which one of the $R_4$ members is a nitro residue).

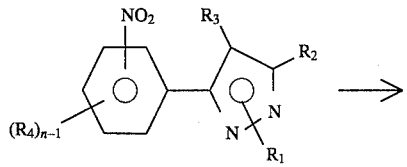

G

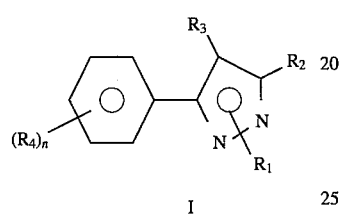

I

A. In the first step of this two step process, compounds according to Formula G are reduced to give a derivative according to Formula I wherein one of the $R_4$ radicals is an amine group. Reducing agents suitable in an acidic medium include, but are not limited to, metals such as iron, zinc, or tin. The reaction solvent can include either organic or inorganic acids, such as acetic acid or hydrochloric acid, and may be used as concentrated acid solutions or dilute aqueous solutions. Reaction temperature is in the range of 0° C. to 200° C., preferably 10° C. to 120° C. The reaction period may be chosen from the range of a few minutes to several weeks depending on the amounts of reagents, reaction temperature, etc.

After completion of the reaction the product is isolated by diluting the reaction mixture with water and the product is isolated by a method such as crystallization or solvent extraction. If necessary, the product is purified by standard methods.

Alternatively, compounds of Formula G may be reduced by catalytic hydrogenation. For catalytic hydrogenation, which may be carried out at atmospheric or elevated pressures, suitable catalysts include Raney nickel, palladium-carbon, palladium black, palladium on any suitable support, palladium oxide, platinum, platinum black, etc. Solvents include any inert solvent which does not markedly hinder the reaction including alcohols, ethers, etc. The product is isolated after completion of the reaction by filtration and concentration of the reaction mixture. If necessary, the product is purified by standard methods such as extraction, crystallization, column chromatography, etc. B. The amine radical of the product of step A can be converted to a variety of functional groups, e.g., a halogen (preferred), cyano, hydroxyl, etc. In the case of conversion of the amine radical to a halogen, a solution or slurry of the product of step A is treated with copper salts including cupric halides, cuprous halides, mixtures of cupric and cuprous halides or other copper salts and their mixtures and with an alkyl nitrite or organic nitrite such as t-butylnitrite. In this reaction any suitable solvent may be employed, although, anhydrous solvents such as anhydrous acetonitrile are preferred. Reaction temperature is in the range of 0° C. to 200° C., preferably 10° C. to 100° C. The reaction period may be chosen from the range of a few minutes to several weeks depending on the amounts of reagents, reaction temperature, etc. The product is isolated after completion of the reaction by filtration and/or concentration of the reaction mixture. If necessary, the product is purified by standard methods such as extraction, crystallization, column chromatography, etc.

Alternative process operations for converting the amine radical to various functional groups, including those mentioned in the preceding paragraph include use of various conventional procedures, e.g., the Sandmeyer, Meerwein, etc., reactions which employ diazonium salts as intermediates.

Process VI

In this process description, compounds according to Formula I, wherein one of the $R_4$ members is YH, are prepared from compounds according to Formula I wherein one of the $R_4$ members is $YR_{15}$ and $R_{15}$ is not hydrogen.

The reaction can be carried out as a solution or suspension in any suitable solvent or neat. A Lewis acid such as, but not limited to, $BBr_3$, $AlCl_3$, etc., or inorganic or organic acids such as concentrated or aqueous hydrochloric acid, sulfuric acid, hydrobromic acid, acetic acid, etc., can be employed. Alternatively, nucleophilic reagents for dealkylation may be employed including trimethylsilyl iodide, cyanide salts, mercaptide salts, alkali metal halides, etc. Reaction temperature is in the range of 0° C. to 200° C., preferably 10° C. to 100° C. The reaction period may be chosen from the range of a few minutes to several weeks depending on the amounts of reagents, reaction temperature, etc. The product is isolated after completion of the reaction by filtration and/or concentration of the reaction mixture. If necessary, the product is purified by standard methods such as extraction, crystallization, column chromatography, etc.

Process VII

In this process description, compounds according to Formula I (which includes Formulae II and III compounds), wherein one of the $R_4$ members is $YR_{15}$ and $R_{15}$ is not hydrogen, are prepared from compounds according to Formula I wherein one of the $R_4$ members is YH or $NR_{16}R_{17}$.

In representative embodiments of this process, formation of products defined above can be carried out by treatment of the starting material with an alkylating agent such as an alkyl halide or alkyl sulfonate, e.g., methyl iodide, allyl bromide, propargyl bromide, methyl phenylsulfonate, etc., or an acylating agent. The reaction may be carried out in any suitable solvent or mixture of solvents, with or without a catalyst, in the presence or absence of a base. The preferred solvents are dimethylsulfoxide, acetone, dimethylformamide, dioxane, etc., or mixtures of solvents including two phase mixtures (such as water and methylene chloride or other organic solvent). In the case of two immiscible liquid phases, it may be advantageous to add a phase transfer catalyst such as a benzyltrialkylammonium halide or other ammonium salt. The base may be an organic base (such as a trialkylamine or another organic amine) or an inorganic base (an alkali carbonate or metal, such as potassium or sodium carbonate or sodium hydroxide). Reaction temperature is in the range of 0° C. to 200° C., preferably 10° C. to 100° C. The reaction period may be chosen from the range of a few minutes to several weeks depending on the amounts of reagents, reaction temperature, etc. The product is isolated after completion of the reaction by filtration and/or concentration of the reaction mixture. If necessary, the product is purified by standard methods such as extraction, crystallization, column chromatography, etc.

Process VIII

This process describes the preparation of compounds of Formula K (Formula II compounds wherein $R_7$ is $YCH_{2-p}(R_{25})_p COYR_{27}$) from the corresponding compounds of Formula H. The radicals $R_{25-27}$ are as previously defined for the said $R_4$ members; the Y members are independently as previously defined and p is an integer from 0 to 2.

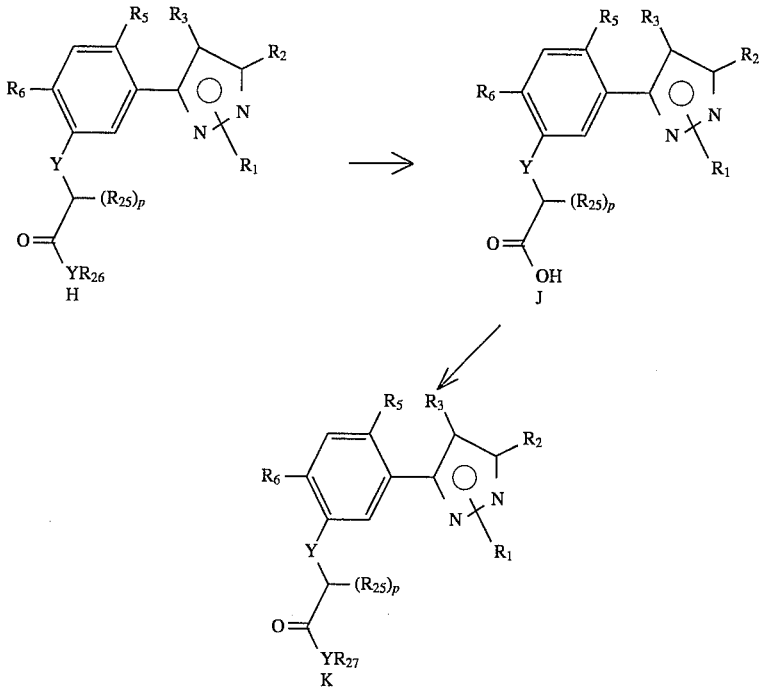

A. In the first step of this two step process, compounds of Formula H are converted to compounds of Formula J by hydrolysis of the $YR_{26}$ radical. The reaction can be carried out in any suitable solvent or mixture of solvents, with or without a catalyst, in the presence of a base or acid. The preferred solvents are water, alcohols, dioxane, dimethylsulfoxide, acetic acid, acetone, dimethylformamide, etc. In the case of base hydrolysis, inorganic bases such as alkali hydroxides are preferred. For acid hydrolysis, inorganic acids such as concentrated hydrochloric acid or sulfuric acid, organic acids or mixtures of such acids may be employed. Reaction temperature is in the range of about 0° C. to 200° C., preferably 10° C. to 100° C. The reaction period may be chosen from the range of a few minutes to several weeks depending on the amounts of reagents, reaction temperature, etc. After completion of the reaction the product is isolated by diluting the reaction mixture with water and/or treating the solution with acid (in the case of base hydrolysis) and the product is isolated by a method such as crystallization or solvent extraction. If necessary, the product is purified by standard methods.

B. The last step of this process is meant to include the transformation of compounds of Formula J to compounds of Formula K by any of the variety of standard techniques for the preparation of derivatives of carboxylic acids. This process step is an esterification or an amide-forming reaction. The esterification can be carried out by using an excess of the alcohol corresponding to the objective ester in the presence of a mineral acid (e.g., sulfuric acid). The amide derivatives can be prepared by treating compounds of Formula J with the desired amine either neat or in a suitable solvent. The esterification or amide-forming reactions can also be carried out in the presence of an inert solvent and a dehydrating agent.

Alternatively, the product of step A can be converted to an acid halide or anhydride and treated with an alcohol or amine. Preparation of the acid halide is carried out in the presence of a halogenating agent such as, but not limited to, thionyl chloride, phosphorus pentachloride, oxalyl chloride, etc., with or without an inert solvent. Any inert solvent which does not interfere with the reaction may be employed. A catalytic amount of an amine base such as triethylamine, pyridine or dimethylformamide or the like may be added for the purpose of promoting this reaction. The reaction temperature is in the range of $-20°$ C. to the boiling point of the solvent used. The reaction period ranges from several minutes to 48 hours depending upon the amounts of reactants used and the reaction temperature. After completion of the reaction, the excess halogenating reagent and solvent(s) are removed from the reaction product by evaporation or distillation. The resultant acid halide may be subjected to an amine or alcohol directly or purified by the usual means.

The acid halide is treated with an alcohol or amine to give a compound of Formula K. The reaction can be carried out in the absence of a solvent, in the presence of an inert solvent or with a mixture of solvents including two phase mixtures (such as water and methylene chloride or other organic solvent). A base such as triethylamine, pyridine, alkali metal hydroxide and/or a catalytic amount of a phase transfer catalyst such as a benzyltrialkylammonium halide or other ammonium salt may be added for the purpose of promoting this reaction. The reaction temperature is in the range of $-20°$ C. to the boiling point of the solvent used. The reaction period ranges from several minutes to 48 hours depending upon the amounts of reactants used and the reaction temperature. The product is isolated after completion of the reaction by filtration and/or concentration of the reaction mixture. If necessary, the product is purified by standard methods such as extraction, crystallization, column chromatography, etc.

Compounds required as starting materials for Processes IX through XI are obtained by the above Processes II–VIII.

Process IX

In this process description, compounds according to Formula N are prepared from compounds according to Formula L (Formula II compounds wherein $R_6$ is $YCH_{2-q}(R_{28})_q COOR_{29}$, $R_7$ is a nitro radical, Y is as previously defined, q is an integer from 0 to 2 and radicals $R_{28-30}$ are as previously defined for the said $R_4$ members), as described below.

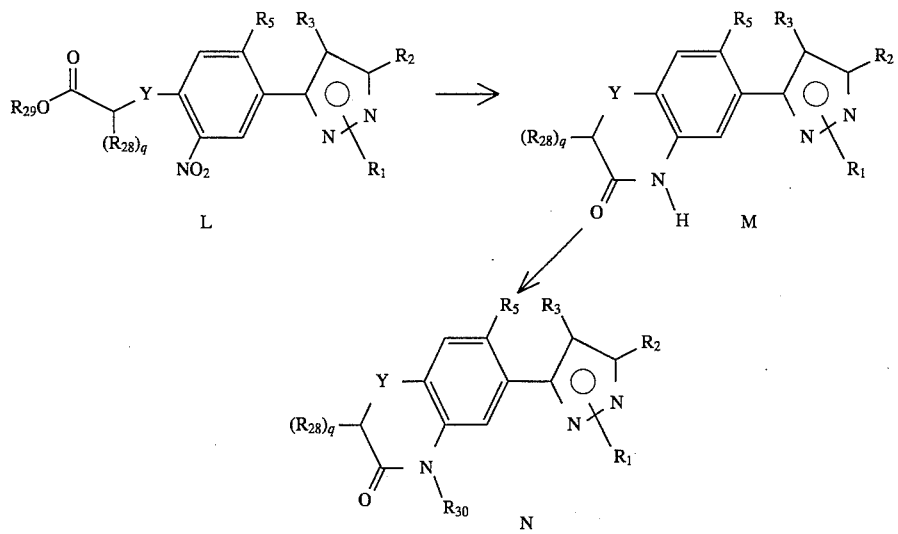

A. In the first step of this two step process, compounds according to Formula L are converted to compounds of Formula M by reduction of the nitro radical to an amine radical and subsequent cyclization. By choice of the reaction conditions, one can obtain either the uncyclized amine (Formula L compounds wherein the nitro radical is substituted by an amine radical) or the cyclized product. Typically, reaction conditions are chosen such that the cyclized product is obtained directly. Alternatively, the uncyclized amine can be isolated by standard methods and cyclized to give compounds of Formula M in a separate step using standard conditions. Reducing agents suitable in an acidic medium include, but are not limited to, metals such as iron, zinc or tin. The reaction solvent can include either organic or inorganic acids, such as acetic acid or hydrochloric acid, and may be used as concentrated acid solutions or dilute aqueous solutions. Reaction temperature is in the range of 0° C. to 200° C., preferably 10° C. to 120° C. The reaction period may be chosen from the range of a few minutes to several weeks depending on the amounts of reagents, reaction temperature, etc.

After completion of the reaction the product is separated by diluting the reaction mixture with water and isolated by a method such as crystallization or solvent extraction. If necessary, the product is purified by standard methods.

Alternatively, compounds of Formula L may be reduced by catalytic hydrogenation. For catalytic hydrogenation, which may be carried out at normal or elevated pressures, suitable catalysts include Raney nickel, palladium-carbon, palladium black, palladium on any suitable support, palladium oxide, platinum, platinum black, etc. Solvents include any inert solvent which does not markedly hinder the reaction including alcohols, ethers, etc. By choice of the reaction conditions, one can obtain either the uncyclized amine (Formula L compounds wherein the nitro radical is substituted by an amine radical) or the cyclized product. Typically, reaction conditions are chosen such that the cyclized product is obtained directly. Alternatively, the uncyclized amine can be isolated by standard methods and cyclized to give compounds of Formula M in a separate step using standard conditions. The product is isolated after completion of the reaction by filtration and concentration of the reaction mixture. If necessary, the product is purified by standard methods such as extraction, crystallization, column chromatography, etc.

B. In this step the product of step A is converted to compounds of Formula N. Formation of products defined above can be carried out by treatment of compounds of Formula M with an alkylating agent such as an alkyl halide or alkyl sulfonate, e.g., methyl iodide, allyl bromide, propargyl bromide, methyl phenylsulfonate, etc., or an acylating agent. The reaction may be carried out in any suitable solvent or mixture of solvents, with or without a catalyst, in the presence or absence of a base. The preferred solvents are dimethylsulfoxide, acetone, dimethylformamide, dioxane, etc., or mixtures of solvents including two phase mixtures (such as water and methylene chloride or other organic solvent). In the case of two immiscible liquid phases, it may be advantageous to add a phase transfer catalyst such as a benzyltrialkylammonium halide or other ammonium salt. The base may be an organic base (such as a trialkylamine or another organic amine) or an inorganic base such as potassium or sodium carbonate or hydroxide. Reaction temperature is in the range of 0° C. to 200° C., preferably 10° C. to 120° C. The reaction period may be chosen from the range of a few minutes to several weeks depending on the amounts of reagents, reaction temperature, etc. The product is isolated after completion of the reaction by filtration and/or concentration of the reaction mixture. If necessary, the product is purified by standard methods such as extraction, crystallization, column chromatography, etc.

Process X

In this process description, compounds according to Formula Q wherein $R_{33}$ is not hydrogen are prepared from compounds according to Formula O (Formula II compounds wherein $R_6$ is a nitro radical, $R_7$ is $YCH_{2-r}(R_{31})_r COOR_{32}$, Y is as previously defined, r is an integer from 0 to 2 and radicals $R_{31-33}$ are as previously defined for the said $R_4$ members.

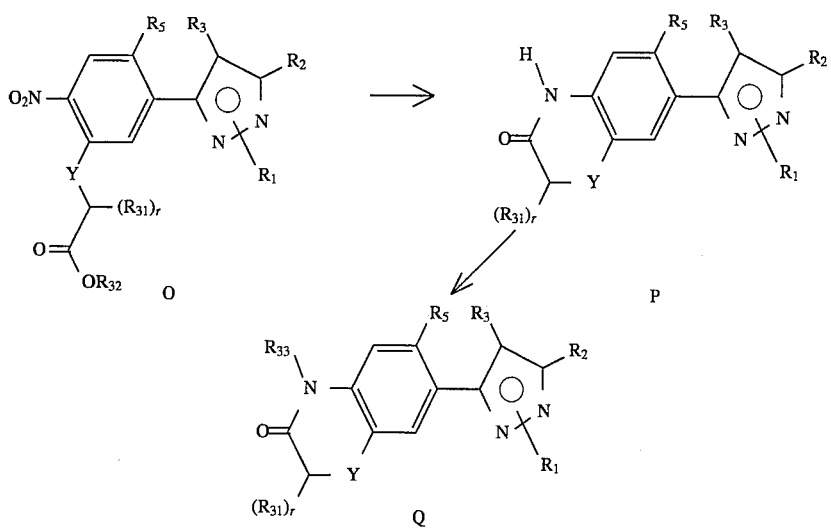

A. In the first step of this two step process, compounds according to Formula O are converted to compounds of Formula P by reduction of the nitro radical to an amine radical and subsequent cyclization. By choice of the reaction conditions, one can obtain either the uncyclized amine (Formula O compounds wherein the nitro radical is substituted by an amine radical) or the cyclized product. Typically, reaction conditions are chosen such that the cyclized product is obtained directly. Alternatively, the uncyclized amine can be isolated by standard methods and cyclized to give compounds of Formula P in a separate step using standard conditions. Reducing agents suitable in an acidic medium include, but are not limited to, metals such as iron, zinc or tin. The reaction solvent can include either organic or inorganic acids, such as acetic acid or hydrochloric acid, and may be used as concentrated acid solutions or dilute aqueous solutions. Reaction temperature is in the range of 0° C. to 200° C., preferably 10° C. to 120° C. The reaction period may be chosen from the range of a few minutes to several weeks depending on the amounts of reagents, reaction temperature, etc.

After completion of the reaction the product is separated by diluting the reaction mixture with water and isolated by a method such as crystallization or solvent extraction. If necessary, the product is purified by standard methods.

Alternatively, compounds of Formula O may be reduced by catalytic hydrogenation. For catalytic hydrogenation, which may be carried out at normal or elevated pressures, suitable catalysts include Raney nickel, palladium-carbon, palladium black, palladium on any suitable support, palladium oxide, platinum, platinum black, etc. Solvents include any inert solvent which does not markedly hinder the reaction including alcohols, ethers, etc. By choice of the reaction conditions, one can obtain either the uncyclized amine (Formula O compounds wherein the nitro radical is substituted by an amine radical) or the cyclized product. Typically, reaction conditions are chosen such that the cyclized product is obtained directly. Alternatively, the uncyclized amine can be isolated by standard methods and cyclized to give compounds of Formula P in a separate step using standard conditions. The product is isolated after completion of the reaction by filtration and concentration of the reaction mixture. If necessary, the product is purified by standard methods such as extraction, crystallization, column chromatography, etc.

B. In this step the product of step A is converted to compounds of Formula Q wherein $R_{33}$ is not hydrogen. Formation of products defined above can be carried out by treatment of compounds of Formula P with an alkylating agent such as an alkyl halide or alkyl sulfonate, e.g., methyl iodide, allyl bromide, propargyl bromide, methyl phenylsulfonate, etc., or an acylating agent. The reaction may be carried out in any suitable solvent or mixture of solvents, with or without a catalyst, in the presence or absence of a base. The preferred solvents are dimethylsulfoxide, acetone, dimethylformamide, dioxane, etc. The base may be an organic base (such as a trialkylamine or another organic amine) or an inorganic base such as potassium or sodium carbonate or hydroxide. Reaction temperature is in the range of 0° C. to 200° C., preferably 10° C. to 120° C. The reaction period may be chosen from the range of a few minutes to several weeks depending on the amounts of reagents, reaction temperature, etc. The product is isolated after completion of the reaction by filtration and/or concentration of the reaction mixture. If necessary, the product is purified by standard methods such as extraction, crystallization, column chromatography, etc.

Process XI

This section describes a process for the preparation of compounds according to Formula S from compounds of Formula R (Formula II compounds wherein $R_6$ is an amino radical, $R_7$ is $YC(R_{34})_sCCR_{35}$, Y is as previously defined, s is an integer from 0 to 2 and the radicals $R_{34-36}$ are any of the previously defined $R_4$ members).

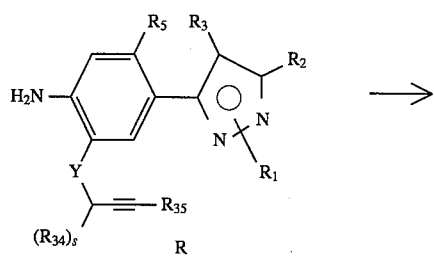

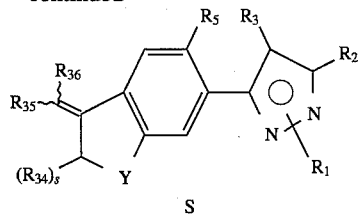

The process for the preparation of compounds of Formula S suitably proceeds from compounds of Formula R. In this reaction any suitable solvent may be employed, although anhydrous solvents such as anhydrous acetonitrile are preferred. A solution or slurry of a compound of Formula R is treated with copper salts including cupric halides, cuprous halides, mixtures of cupric and cuprous halides or other copper salts and their mixtures and with an alkyl nitrite or organic nitrite such as t-butylnitrite. Reaction temperature is in the range of 0° C. to 200° C., preferably 10° C. to 100° C. The reaction period may be chosen from the range of a few minutes to several weeks depending on the amounts of reagents, reaction temperature, etc. The product is isolated after completion of the reaction by filtration and/or concentration of the reaction mixture. If necessary, the product is purified by standard methods such as extraction, crystallization, column chromatography, etc.

Process XII

This process describes the preparation of compounds of Formulae U, V, W, X, Y or Z (Formula II compounds in which the $R_7$ substituent is alkyl, substituted alkyl, haloalkyl, carboxaldehyde, carboxylic acid or a carboxylic acid derivative such as the previously defined $CXYR_8$ or $CXR_9$) from compounds of Formula T. The radicals $R_{37}$ and $R_{38}$ are as previously defined for the $R_4$ members and $X_1$ and $X_2$ are halogens. Process schematics are shown below.

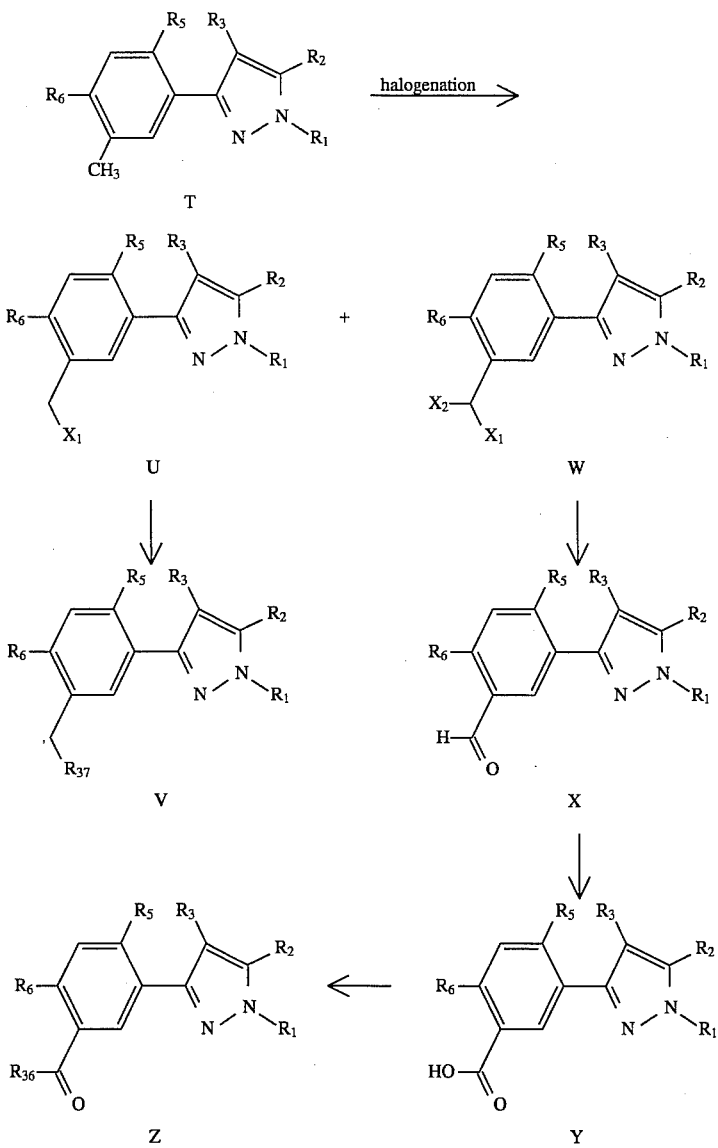

In the first step of this process, compounds of Formula T are converted to either compounds of Formula U or W or a mixture of these products. Any inert solvent may be used in this reaction that does not markedly hinder the reaction from proceeding. Such solvents include, but are not limited to, organic acids, inorganic acids, hydrocarbons, halogenated hydrocarbons, aromatic hydrocarbons, ethers, sulfoxides or sulfones. Halogenating agents suitable for the above reaction include bromine, chlorine, N-bromosuccinimide, N-chlorosuccinimide, sulfuryl chloride, etc. With some halogenating agents it is preferable to use an organic peroxide or light as a catalyst. The amount of halogenating agent can range from less than one molar amount to an excess. Reaction temperature is in the range of $-78°$ C. to $200°$ C., preferably $10°$ C. to $120°$ C. The reaction period may be chosen from the range of a few minutes to several weeks depending on the amounts of reagents, reaction temperature, etc. After completion of the reaction the product or products are isolated by diluting the reaction mixture with water and the product(s) are isolated by a method such as crystallization or solvent extraction. If necessary, the product(s) are purified by standard methods.

Compounds of Formula U can be converted to compounds of Formula V by displacement of the halogen radical $X_1$ by a suitable nucleophile. Formation of products of Formula V can be carried out by treatment of compounds of Formula U with an alkoxide, thioalkoxide, cyanide, amine, alkyl or aryl anion, etc., or an alcohol, mercaptan, amine, etc., in the presence of a base in any suitable solvent or mixture of solvents. The preferred solvents are dimethylsulfoxide, acetone, dimethylformamide, dioxane, water, etc., or mixture of solvents including two-phase mixtures (such as water and methylene chloride or other organic solvent). The base may be an organic base (such as a trialkylamine or another organic amine) or an inorganic base (an alkali carbonate such as potassium carbonate or sodium carbonate or an alkali metal hydroxide such as sodium hydroxide). In the case of two immiscible liquid phases, it may be advantageous to add a phase transfer catalyst such as a benzyltrialkylammonium halide or other ammonium salt. Reaction temperature is in the range of $-78°$ C. to $200°$ C., preferably $10°$ C. to $120°$ C. The reaction period may be chosen from the range of a few minutes to several weeks depending on the amounts of reagents, reaction temperature, etc. The product is isolated after completion of the reaction by filtration and/or concentration of the reaction mixture. If necessary, the product is purified by standard methods such as extraction, crystallization, column chromatography, etc.

Formation of products of Formula X can be carried out by acid hydrolysis of compounds of Formula W. To effect acid hydrolysis, compounds of Formula W are subjected to an excess of a mineral acid such as hydrochloric acid or sulfuric acid, with excess of sulfuric acid being preferred. Reaction temperature is in the range of $0°$ C. to the boiling point of the inert solvent, preferably $10°$ C. to $100°$ C. The reaction period may be chosen from the range of a few minutes to several weeks depending on the amounts of reagents, reaction temperature, etc. After completion of the reaction the product or products are separated by diluting the reaction mixture with water and are isolated by a method such as crystallization or solvent extraction. If necessary, the product(s) are purified by standard methods.

Compounds of Formula Y are obtained by oxidation of Formula X compounds. Any suitable inert solvent may be employed in this reaction including hydrocarbons, aromatic hydrocarbons, pyridine and its derivatives, water, etc. Oxidizing agents employed include, but are not limited to, potassium permanganate or potassium dichromate. Reaction temperature is in the range of $-50°$ C. to the boiling point of the inert solvent, preferably $10°$ C. to $100°$ C. The reaction period may be chosen from the range of a few minutes to several weeks depending on the amounts of reagents, reaction temperature, etc. After completion of the reaction the product or products are separated by diluting the reaction mixture with water and isolated by a method such as crystallization or solvent extraction. If necessary, the product(s) are purified by standard methods.

The last step of this process is meant to include the transformation of compounds of Formula Y to compounds of Formula Z by any of the variety of standard techniques for preparation of derivatives of carboxylic acids. This process step is an esterification or an amide-forming reaction. This may be accomplished directly from compound of Formula Y or via an alkali metal salt of compound of Formula Y. The esterification can be carried out by using an excess of the alcohol corresponding to the objective ester in the presence of a mineral acid (e.g., sulfuric acid). The amide derivatives can be prepared by treating compound of Formula Y with the desired amine either neat or in a suitable solvent. The esterification or amide-forming reactions can also be carried out in the presence of an inert solvent and a dehydrating agent.

Alternatively, compounds of Formula Y can be converted to an acid halide or anhydride and treated with an alcohol or amine. Preparation of the acid halide is carried out in the presence of a halogenating agent such as, but not limited to, thionyl chloride, phosphorus pentachloride, oxalyl chloride, etc., with or without an inert solvent. Any inert solvent which does not interfere with the reaction may be employed. A catalytic amount of an amine base such as triethylamine, pyridine or dimethylformamide or the like may be added for the purpose of promoting this reaction. The reaction temperature is in the range of $-20°$ C. to the boiling point of the solvent used. The reaction period ranges from several minutes to 48 hours depending upon the amounts of reactants used and the reaction temperature. After completion of the reaction, the excess halogenating reagent and solvent(s) are removed from the reaction product by evaporation or distillation. The acid halide is treated with an alcohol or amine to give a compound of Formula Z. The reaction can be carried out in the absence of a solvent, in the presence of an inert solvent or with a mixture of solvents including two phase mixtures (such as water and methylene chloride or other organic solvent). A base such as triethylamine, pyridine, alkali metal and/or a catalytic amount of a phase transfer catalyst such as a benzyltrialkylammonium halide or other ammonium salt may be added for the purpose of promoting this reaction. The reaction temperature is in the range of $-20°$ C. to the boiling point of the solvent used. The reaction period ranges from several minutes to 48 hours depending upon the amounts of reactants used and the reaction temperature. The product is isolated after completion of the reaction by filtration and/or concentration of the reaction mixture. If necessary, the product is purified by standard methods such as extraction, crystallization, column chromatography, etc.

Process XIII

This section describes a process for the preparation of compounds according to Formula I in which one of the $R_4$ residues is a thiol group (Formula AA) starting with compounds according to Formula I.

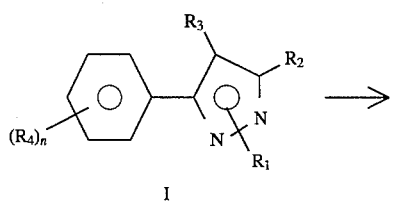

I

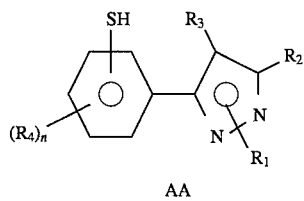

AA

In this process, the desired compounds are obtained by preparation of a halosulfonyl intermediate followed by reduction to give compounds of Formula AA. Any solvent may be employed that does not hinder the progress of the reaction such as halogenated hydrocarbons, ethers, alkylnitriles, mineral acids, etc. An excess of chlorosulfonic acid is preferred as both the reagent and solvent for the formation of chlorosulfonyl intermediates. The reaction temperature is in the range of 25° C. to the boiling point of the solvent employed. The reaction period may be chosen from the range of a few minutes to several weeks depending on the amounts of reagents, reaction temperature, etc. After completion of the reaction the product or products are isolated by diluting the reaction mixture with water and the product(s) are isolated by a method such as crystallization or solvent extraction. If necessary, the product(s) are purified by standard methods.

Reduction of the halosulfonyl intermediate can be carried out in organic or inorganic acids, such as acetic acid or hydrochloric acid, or mixtures of these acids in inert solvents. Reducing agents suitable in an acidic medium include, but are not limited to, metals such as iron, zinc or tin. Reaction temperature is in the range of 0° C. to 150° C., preferably 10° C. to 120° C. The reaction period may be chosen from the range of a few minutes to several weeks depending on the amounts of reagents, reaction temperature, etc.

After completion of the reaction the product is isolated by diluting the reaction mixture with water and the product is isolated by a method such as crystallization or solvent extraction. If necessary, the product is purified by standard methods.

Process XIV

This section describes a process for the preparation of compounds according to Formula I in which one of the $R_4$ residues is a cyclic (thio)ketal or (thio)acetal radical (Formula CC) starting with compounds according to Formula BB.

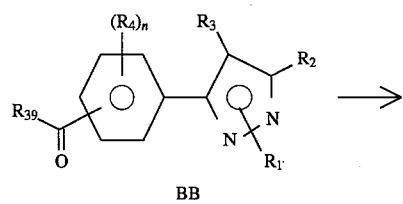

BB

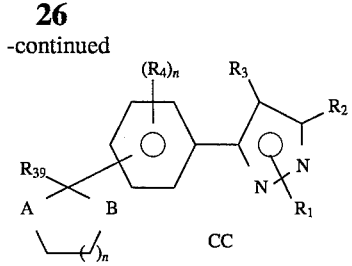

CC $R_{39}$ is hydrogen or a previously-defined $R_4$ member; A and B are independently O or S and n is an integer from 0 to 2. In this process, the desired compounds of Formula CC are prepared from compounds of Formula BB by conversion of the carbonyl group to a cyclic (thio)acetal or (thio)ketal group. The aldehyde or ketone group of a compound of Formula BB is treated with a diol, dithiol or hydroxythiol. Any solvent may be employed that does not hinder the progress of the reaction such as halogenated hydrocarbons, aromatic hydrocarbons, ethers, alkyl-nitriles, mineral acids, etc. Alternatively, the reaction may be carried out in the absence of a solvent. Typically, the reaction is carried out in the presence of an acid such as mineral acids, organic acids, etc. The reaction temperature is in the range of 25° C. to the boiling point of the solvent employed. The reaction period may be chosen from the range of a few minutes to several weeks depending on the amounts of reagents, reaction temperature, etc. After completion of the reaction the product or products are isolated by concentration of the reaction mixture and purified by a method such as crystallization or solvent extraction. If necessary, the product(s) are further purified by standard methods.

Process XV

This section describes a process for the preparation of compounds according to Formula DD starting with compounds according to Formula BB.

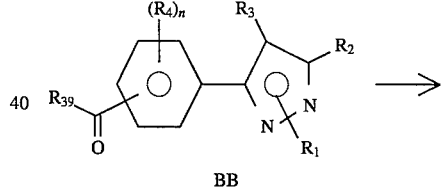

BB

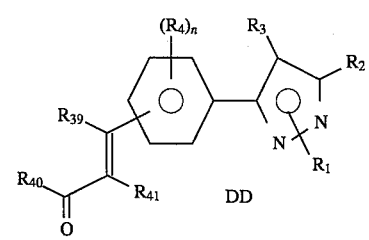

DD $R_{39}$–$R_{41}$ are hydrogen or previously-defined $R_4$ members. Compounds of Formula DD are prepared by conversion of the ketone or aldehyde group of compounds of Formula BB to an alkene group. This transformation can be carried out by treatment of a compound of Formula BB with a Wittig type reagent such as an alkylidenephosphorane, ylides derived from phosphonium salts or phosphonate esters, alkylidenesulfuranes, etc. Suitable solvents include, but are not limited to, aromatic hydrocarbons, alcohols, alkanes, ethers, halogenated hydrocarbons, etc. The reaction temperature is in the range of −50° C. to the boiling point of the solvent employed. The reaction period may be chosen from the range of a few minutes to several weeks depending on the amounts of reagents, reaction temperature, etc. After completion of the reaction the product or products are isolated by concentration of the reaction mixture and the product(s) are purified by a method such as crystallization or solvent extraction. If necessary, the product(s) are further purified by standard methods.

Process XVI

This section describes a process for the preparation of compounds according to Formula EE starting with compounds according to Formula BB.

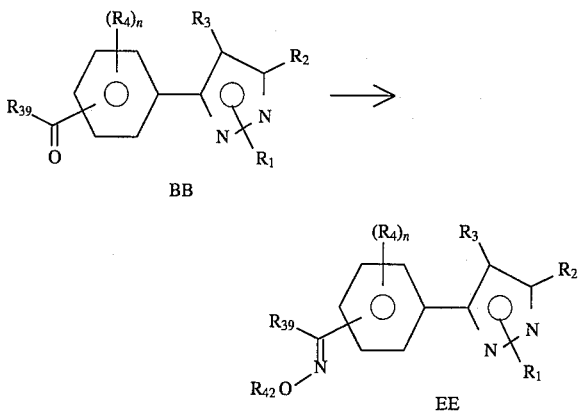

$R_{39}$ and $R_{42}$ are as previously defined for the $R_4$ members. In this process step, compounds of Formula EE which have an oxime substituent as one of the phenyl radicals are prepared from compounds of Formula BB. The ketone or aldehyde substituent of a compound of Formula BB can be converted to an oxime by either of two methods. The starting aldehyde or ketone of Formula BB can be treated with an O-substituted oxime to afford an oxime of Formula EE. This compound may be further derivatized by standard methods known by those skilled in the art. Examples of this approach include, but are not limited to, treatment of the aldehyde or ketone with (aminooxy)acetic acid or other 2-(aminooxy)carboxylic acids and conversion of the resultant carboxylic acid to any of a number of carboxylic acid derivatives such as amides, esters, thioesters, etc. Alternatively, the oxime can be prepared by treatment of compounds of Formula BB with hydroxylamine or hydroxylamine salts. The resultant oxime can be alkylated to afford derivatives by treatment with an alkylating agent such as alkyl halides, alkyl sulfonates, etc. Suitable solvents for the above reactions include, but are not limited to, aromatic hydrocarbons, alkanes, ethers, alcohols, halogenated hydrocarbons, etc. The reaction temperature is in the range of −50° C. to the boiling point of the solvent employed. The reaction may be carried out with or without a base. In cases in which a base is employed, sodium acetate, alkali metal carbonates such as sodium carbonate or alkali metal hydroxides such as sodium hydroxide may be used. The reaction period may be chosen from the range of a few minutes to several weeks depending on the amounts of reagents, reaction temperature, etc. After completion of the reaction the product or products are isolated by concentration of the reaction mixture and the product(s) are purified by a method such as crystallization or solvent extraction. If necessary, the product(s) are further purified by standard methods.

The following Examples 1–42 describe specific working embodiments for the preparation of representative compounds according to this invention.

Examples 1 through 4 describe specific working embodiments of Process I.

EXAMPLE 1

This example describes the preparation of 3-(2,5-difluorophenyl)-1-methyl-5-(trifluoromethyl)-1H-pyrazole (Compound No. 40) and of 5-(2,5-difluorophenyl)-1-methyl-3-(trifluoromethyl)-1H-pyrazole (Compound No. 20).

A. 28.5 g of 2,5-difluoroacetophenone and 26 g of ethyl trifluoroacetate were stirred in 400 ml of anhydrous ether and cooled in an ice bath. 42 ml of 25 wt % sodium methoxide in methanol was then added over 5 minutes. After stirring 1 hour at room temperature, the reaction mixture was extracted with water, the water acidified and extracted with methylene chloride to give 42 g of 1-(2,5-difluorophenyl)-3-(trifluoromethyl)-propane-1,3-dione.

B. 34.5 g of 1-(2,5-difluorophenyl)-3-(trifluoromethyl)-propane-1,3-dione was dissolved in 250 ml of acetic acid and 9.5 mL of methylhydrazine slowly added. The mixture was heated at 100° C. for 5 minutes then cooled and diluted with ether. The ether solution was washed with water and potassium carbonate solution, then dried with magnesium sulfate, filtered and concentrated. The residue was chromatographed to give 9.5 g of 3-(2,5-difluorophenyl)-1-methyl-5(trifluoro-methyl)-1H-pyrazole.

Anal. Calc. for $C_{11}H_7N_2F_5$: C,50.39%; H,2.69%; N,10.68%. Found: C,50.48%; H,2.72%; N,10.64%.
and 21.11 g of 5-(2,5-difluorophenyl)-1-methyl-3-(trifluoromethyl)-1H-pyrazole (mp 38°–39° C.).
Anal. Calc. for $C_{11}H_7N_2F_5$: C,50.39%; H,2.69%; N,10.68%. Found: C,50.63%; H,2.65%; N,10.40%.

EXAMPLE 2

This example describes the preparation of 5-(2,4-difluorophenyl)-3-(trifluoromethyl)-1H-pyrazole (Compound No. 6).

A. To a solution of 40.0 g (0.256 moles) 2',4'-difluoroacetophenone (commercially available) in 400 mL diethyl ether at 0° C. was added 40 mL (0.405 moles) ethyl trifluoroacetate. At 5° C., 80 mL of a 25% wt. sodium methoxide in methanol (0.37 moles) were added over 15 minutes. The reaction mixture was stirred overnight at 25° C. The mixture was poured over 300 mL ice water and 21.3 mL (0.37 moles) acetic acid were added. The organic layer was washed two times with water, dried over anhydrous $MgSO_4$, and concentrated in vacuo to give 62.85 g (97%) 4-(2,4-difluorophenyl)-1,1,1-trifluoro-4-hydroxy-3-buten-2-one as a yellow oil; $^1HNMR$ ($CDCl_3$) ppm: 6.61 (s,1H), 6.87 (m, 1H)., 6.97 (m, 1H), 7.97 (m, 1H).

Anal. Calc. for $C_{10}H_5F_5O_2$; C,47.64; H,2.00. Found: C,47.70; H,1.96.

B. At 24° C., 15.0 g (0.06 mole) of the product of step A was dissolved in 50 mL glacial acetic acid and treated with 2 mL (0.064 mole) anhydrous hydrazine, added over a period of 5 minutes. The reaction was heated to 95° C. for 30 minutes. The reaction was cooled and poured into 300 mL ice water. The slurry was filtered and the cake washed with water and air dried to give 13.86 g (94%) of 5-(2,4-difluorophenyl)-3-(trifluoromethyl)-1H-pyrazole as a white solid, mp 157°–158° C.

Anal. Calc. for $C_{10}H_5F_5N_2$: C,48.40; H,2.03; N,11.29. Found: C,48.38; H,2.03; N,11.32.

EXAMPLE 3

This example describes the preparation of 3-(2,4-difluorophenyl)-1-methyl-5-(trifluoromethyl)-1H-pyrazole (Compound No. 42) and of 5-(2,4-difluorophenyl)-1-methyl-3-

(trifluoromethyl)-1H-pyrazole (Compound No. 21).

A slurry of 13.6 g (0.055 mole) of the product of step B, 7.7 g (0.056 mole) $K_2CO_3$, and 3.7 mL (0.06 mole) methyl iodide in 150 mL acetone was stirred overnight at 25° C. The solution was diluted with 300 mL cold water and extracted three times with ethyl acetate. The ethyl acetate extracts were washed with brine, dried over anhydrous $MgSO_4$, and concentrated in vacuo. The residue was purified chromatographically using 5% ethyl acetate in hexane as the eluent to give 8.3 g (58%) of 3-(2,4-difluorophenyl)-1-methyl-5-(trifluoromethyl)-1H-pyrazole as a white solid, mp 51° C.

Anal. Calc. for $C_{11}H_7F_5N_2$: C,50.39; H,2.69; N,10.68. Found: C,50.36; H,2.70; N,10.70.

The chromatography described in the above preparation gave a second fraction which was collected, concentrated and the residue crystallized to give 4.0 g (28% yield) 5-(2,4-difluorophenyl)-1-methyl-3-(trifluoromethyl)-1H-pyrazole as a white solid, mp 37°–38° C.

Anal. Calc. for $C_{11}H_7F_5N_2$: C,50.39; H,2.69; N,10.68. Found: C,50.40; H,2.67; N,10.67.

EXAMPLE 4

This example describes the preparation of 3-(2,5-difluorophenyl)-1-methyl-5-(trifluoromethyl)-1H-pyrazole (Compound No. 40).

A solution of 8.5 g (34 mmole) of dry 5-(2,5-difluorophenyl)-1H-3-(trifluoromethyl)-1H-pyrazole in 100 mL of anhydrous toluene was heated to reflux in an apparatus equipped with a Dean-Stark trap and treated with 3.25 mL of dimethylsulfate. The mixture was refluxed for 5 hours, allowed to cool and washed with 10% w/v aqueous NaOH. The organic phase was dried with $MgSO_4$ and concentrated to afford 7.74 g (86.2%) of a clear, almost colorless oil nD 1.4925 (25° C.).

Anal. Calc. for $C_{11}H_7N_2F_5$: C,50.39%; H,2.69%; N,10.68%. Found: C,50.48%; H,2.72%; N,10.64%.

Examples 5 through 7 describe specific working embodiments of Process II.

EXAMPLE 5

This example describes the preparation of 4-chloro-5-(2,5-difluorophenyl)-1-methyl-5-(trifluoromethyl)-1H-pyrazole (Compound No. 361).

At 25° C., 5.24 g (0.02 mole) 3-(2,5-difluorophenyl)-1-methyl-5-(trifluoromethyl)-1H-pyrazole was dissolved in 40 mL glacial acetic acid and 2.1 g (0.03 mole) chlorine gas was bubbled in over a period of 1 hour. The reaction mixture was allowed to stir for 2 hours. The reaction solution was poured into 200 mL ice water and extracted with ethyl acetate. The organic layer was washed with water, a saturated $NaHCO_3$ solution, brine and dried over anhydrous $MgSO_4$, and stripped in vacuo. The residue was purified chromatographically using 3% ethyl acetate in hexane as the eluent to give 5.87 g (99%) of 4-chloro-5-(2,5-difluorophenyl)-1-methyl-5-(trifluoro-methyl)-1H-pyrazole as a light yellow oil $n_D^{25}$ 1.4977.

Anal. Calc. for $C_{11}H_6Cl_1F_5N_2$: C,44.54; H,2.04; N,9.44; Cl, 11.95. Found: C,44.53; H,2.00; N,9.44; Cl, 11.94.

EXAMPLE 6

This example describes the preparation of 4-chloro-3-(2,5-difluoro-4-nitrophenyl)-1-methyl-5-(trifluoromethyl)-1H-pyrazole (Compound No. 389).

To 5.00 g of 3-(2,5-difluoro-4-nitrophenyl)-1-methyl-5-(trifluoromethyl)-1H-pyrazole dissolved in 50 ml of acetic acid was added 15 ml of sulfuryl chloride. The mixture was mildly refluxed with 2 ml portions of sulfuryl chloride added every 15 minutes. After 6 hours, the mixture was cooled, then diluted with water and extracted with ether. The ether was washed 3 times with water, dried with anhydrous magnesium sulfate, filtered and concentrated. The residue was chromatographed to give a quantitative yield of 4-chloro-3-(2,5-difluoro-4-nitrophenyl)-1-methyl-5-(trifluoromethyl)-1H-pyrazole.

Anal. Calc. for $C_{11}H_5N_3O_2Cl_1F_5$: C,38.67%; H,1.48%; N,12.30%. Found: C,38.73%; H,1.48%; N,12.34%.

EXAMPLE 7

This example describes the preparation of 4-chloro-3-(4-chloro-2-fluoro-5-methoxyphenyl)-1-(1-methylethyl)-5-(trifluoromethyl)-1H-pyrazole (Compound No. 489).

To a solution of 1.6 g of 3-(4-chloro-2-fluoro-5-methoxyphenyl)-1-(1-methylethyl)-5-(trifluoromethyl)-1H-pyrazole in 20 mL of dimethylformamide was added 2.0 g of N-chlorosuccinimide. The solution was heated to 80° C. for 2 hours, allowed to cool and poured into ice water. The aqueous mixture was extracted three times with methylene chloride, the combined organic extracts washed with water, dried with $MgSO_4$ and concentrated to give a crude oil. The oil was purified by chromatography and distilled bulb-to-bulb to afford 1.54 g of 4-chloro-3-(4-chloro-2-fluoro-5-methoxyphenyl)-1-(1-methylethyl)-5-(trifluoromethyl)-1H-pyrazole as a yellow oil, nD 1.5192 (24° C.).

Anal. Calc. for $C_{14}H_{12}N_2O_1F_4Cl_1$: C,45.31%; H,3.26%; N,7.55%. Found: C,45.19%; H,3.27%; N,7.49%.

Examples 8 through 10 describe specific working embodiments of Process III.

EXAMPLE 8

This example describes the preparation of 3-(2,5-difluoro-4-nitrophenyl)-1-methyl-5-(trifluoromethyl)-1H-pyrazole (Compound No. 388).

To an ice cooled solution of 50 ml of fuming nitric acid (90%) was added slowly 8.29 g of 3-(2,5-difluorophenyl)-1-methyl-5-(trifluoromethyl)-1H-pyrazole. After addition, the mixture was allowed to warm to room temperature and then gently heated to 52° C. Heated for 2.5 hours, then cooled and poured onto ice. The resulting mixture was extracted with ether and the ether then washed twice with water, dried with anhydrous magnesium sulfate, filtered and the solvent removed by concentration in vacuo. The residue was purified utilizing a combination of chromatography and crystallization to give 5.62 g of 3-(2,5-difluoro-4-nitrophenyl)-1-methyl-5-(trifluoromethyl)-1H-pyrazole, mp 80°–81° C.

Anal. Calc. for $C_{11}H_6N_3O_2F_5$: C,43.01%; H,1.97%; N,13.68%. Found: C,42.99%; H,1.97%; N,13.68%.

EXAMPLE 9

This example describes the preparation of 4-bromo-3-(2,5-difluoro-4-nitrophenyl)-1-methyl-5-(trifluoromethyl)-1H-pyrazole (Compound No. 396).

At 15° C., 9.5 g (0.03 mole) 4-bromo-3-(2,5-difluorophenyl)-1-methyl-5-(trifluoromethyl)-1H-pyrazole was slowly added to 100 mL of fuming nitric acid. The reaction warmed to 28° C. over a period of 20 minutes. The reaction mixture was stirred at 30° C. for 4 hours. The mixture was poured into 500 mL of ice. After stirring for 1 hour, the slurry was extracted 3 times with methylene chloride. The methylene chloride extracts were washed with water, dried over anhydrous $MgSO_4$, and concentrated in vacuo. The residue was purified chromatographically using 10% ethyl acetate in hexane as the eluent to give 5.84 g (55%) of 4-bromo-3-(2, 5-difluoro-4-nitrophenyl)-1-methyl-5-(trifluoromethyl)-1H-pyrazole as a white solid, mp 45.5° C.

Anal. Calc. for $C_{11}H_5Br_1F_5N_3O_2$: C,34.22; H,1.31; N,10.88. Found: C,34.25; H,1.38; N,10.76.

EXAMPLE 10

This example describes the preparation of 4-chloro-3-(2, 5-difluoro-4-nitrophenyl)-1-methyl-5-(trifluoromethyl)-1H-pyrazole (Compound No. 389).

A solution of 5.9 g of 4-chloro-5-(2,5-difluorophenyl)-1-methyl-5-(trifluoromethyl)-1H-pyrazole in 6 mL of concentrated $H_2SO4$ was cooled to 15° C. and treated dropwise with a solution of 1.8 g of 70% $HNO_3$ in 2 mL of concentrated $H_2SO_4$. The reaction mixture was allowed to stir at 30° C. for 5 hours and subsequently treated with an additional 1.8 g of 70% $HNO_3$. After stirring overnight at room temperature, the mixture was poured into 250 mL of ice water and extracted with methylene chloride. The methylene chloride extract was washed three times with saturated aqueous $NaHCO_3$, twice with water, dried with $MgSO_4$ and concentrated in vacuo. The resultant material was chromatographed through silica using 10% ethyl acetate in hexane as the eluent to afford 3.93 g (58%) of 4-chloro-3-(2,5-difluoro-4-nitrophenyl)-1-methyl-5-(trifluoromethyl)-1H-pyrazole.

Anal. Calc. for $C_{11}H_5N_3O_2Cl_1F_5$: C,38.67%, H,1.48%; N,12.30%. Found: C,38.73%; H,1.48%; N,12.34.

Examples 11 through 15 describe specific working embodiments of Process IV.

EXAMPLE 11

This example describes the preparation of 4-chloro-3-(2-fluoro-5-methoxy-4-nitrophenyl)-1-methyl-5-(trifluoromethyl)-1-pyrazole (Compound No. 390).

5.04 g of 4-chloro-3-(2,5-difluoro-4-nitrophenyl)-1-methyl-5-(trifluoromethyl)-1H-pyrazole was dissolved in anhydrous ether and the solution cooled with an ice bath, then 3.7 ml of a 25 wt. % sodium methoxide in methanol was added. After addition, the ice bath was removed and the mixture stirred for 30 minutes at room temperature. The solution was then extracted 4 times with water, dried with anhydrous magnesium sulfate, filtered and concentrated. The residue was chromatographed to give 4.63 g of 4-chloro-3-(2-fluoro-5-methoxy-4-nitrophenyl)-1-methyl-5-(trifluoromethyl)-1H-pyrazole, mp 115°–116° C.

Anal. Calc. for $C_{12}H_8N_3O_3Cl_1F_4$: C,40.75%; H,2.28%; N,11.88%. Found: C,40.84%; H,2.24%; N,11.83%.

EXAMPLE 12

This example describes the preparation of 4-chloro-3-(2-fluoro-4-methoxy-5-nitrophenyl)-1-methyl-5-(trifluoromethyl)-1H-pyrazole (Compound No. 387).

At 35° C., 13.7 g (0.04 mole) 4-chloro-3-(2,4-difluoro-5-nitrophenyl)-1-methyl-5-(trifluoromethyl)-1H-pyrazole, 5.5 g (0.04 mole) $K_2CO_3$, and 100 mL methanol were stirred for 1 hour. The reaction was cooled, diluted with 100 mL cold water, and extracted four times with ethyl acetate. The ethyl acetate extracts were washed with brine, dried over anhydrous $MgSO_4$, and stripped in vacuo. The residue was purified chromatographically using 25% ethyl acetate in hexane as the eluent to give 13.0 g (90%) of 4-chloro-3-(2-fluoro-4-methoxy-5-nitrophenyl) -t-methyl-5-(trifluoromethyl) -1H-pyrazole as a white solid, mp 116° C.

Anal. Calc. for $C_{12}H_8Cl_1F_4N_3O_3$: C,40.75; H,2.28; N,11.88. Found: C,40.74; H,2.34; N, 11.90.

EXAMPLE 13

This example describes the preparation of (5-(4-chloro-1-methyl-5-(trifluoromethyl)-1H-pyrazol-3-yl)-4-fluoro-2-nitrophenyl)thio-acetic acid, ethyl ester (Compound No. 393).

At 25° C., 1.5 g (4.5 mmole) 4-chloro-3-(2,5-difluoro-4-nitrophenyl)-1-methyl-5-(trifluoromethyl)-1H-pyrazole, 0.69 g (5.0 mmole) $K_2CO_3$, 0.55 mL (5.0 mmole) ethyl mercaptoacetate, and 0.05 g (0.5 mmole) $CuF_2$ were slurried in 15 mL 1-methyl-2-pyrrolidinone. The reaction mixture was stirred 28° C. for 24 hours. The mixture was cooled, diluted with 100 mL cold water, and extracted four times with ethyl acetate. The ethyl acetate extracts were washed with brine, dried over anhydrous $MgSO_4$, and stripped in vacuo. The residue was purified chromatographically using 10% diethyl ether and 15% methylene chloride in hexane as the eluent to give 0.86 g (43%) of (5-(4-chloro-1-methyl-5-(trifluoromethyl)-1H-pyrazol-3-yl)-4-fluoro-2-nitrophenyl)thio-acetic acid, ethyl ester as a yellow solid, mp 79° C.

Anal. Calc. for $C_{15}H_{12}Cl_1F_4N_3O_4S_1$: C,40.78; H,2.74; N,9.51; S,7.26. Found: C,40.89; H,2.69; N,9.61; S,7.31.

EXAMPLE 14

This example describes the preparation of 5-(4-chloro-1-methyl-5-(trifluoromethyl)-1H-pyrazol-3-yl)-4-fluoro-N-methyl-2-nitro-N-propylbenzeneamine (Compound No. 402).

At 25° C., 6.83 g (0.02 mole) 4-chloro-3-(2,5-difluoro-4-nitrophenyl)-1-methyl-5-(trifluoromethyl)-1H-pyrazole, 4.1 g (0.03 mole) $K_2CO_3$, 3.1 mL (0.03 mole) N-methyl-N-propylamine and a catalytic amount of $CuF_2$ were slurried in 50 mL 1-methyl-2-pyrrolidinone. The reaction mixture was stirred at 35° C. for 2 hours. The mixture was cooled, diluted with 100 mL cold water, and extracted four times with ethyl acetate. The ethyl acetate extracts were washed with brine, dried over anhydrous $MgSO_4$, and stripped in vacuo. The residue was purified chromatographically using 15% ethyl acetate in hexane as the eluent to give 6.8 g (86%) of 5-(4-chloro-1-methyl-5-(trifluoromethyl)-1H-pyrazol-3-yl)-4-fluoro-N-methyl-2-nitro-N-propylbenzeneamine as an orange oil, $n_D^{25} 1.5534$.

Anal. Calc. for $C_{15}H_{15}Cl_1F_4N_4O_2$: C,45.64; H,3.83; N,14.19. Found: C,45.52; H,3.87; N,14.32.

EXAMPLE 15

This example describes the preparation of (4-(4-chloro-1-methyl-5-(trifluoromethyl)-1H-pyrazol-3-yl)-5-fluoro-2-nitrophenoxy)acetic acid, butyl ester (Compound No. 498).

A solution of 3.4 g (0.01 mole) 4-chloro-3-(2,4-difluoro-5-nitrophenyl)-1-methyl-5-(trifluoromethyl)-1H-pyrazole and 1.4 mL (0.011 mole) butyl glycolate in 25 mL anhydrous THF was chilled to 0° C. Maintaining the temperature below 5° C., 0.33 g (0.011 mole) NaH was added in portions. Once the addition was completed, the reaction mixture was allowed to warm to 25° C. After 3 hours the mixture was carefully quenched with water and extracted with ethyl acetate. The ethyl acetate extracts were washed with brine, dried over anhydrous MgSO₄, and concentrated in vacuo. The residue was purified chromatographically with 20% ethyl acetate/hexanes to yield 3.25 g (72%) (4-(4-chloro-1-methyl-5-(trifluoromethyl)-1H-pyrazol-3-yl)-5-fluoro-2-nitrophenoxy)acetic acid, butyl ester as a light yellow solid; mp 65° C.

Anal. Calc. for $C_{17}H_{16}Cl_1F_4N_3O_5$: C,45.00; H,3.55; N,9.26.

Found: C,44.97; H,3.56; N,9.29.

Examples 16 through 19 describe specific working embodiments of Process V.

EXAMPLE 16

This example describes the preparation of 4-chloro-3-(4-chloro-2-fluoro-5-methoxyphenyl)-1-methyl-5-(trifluoromethyl)-1H-pyrazole (Compound No. 312).

A. To a solution of 4.05 g of 4-chloro-3-(2-fluoro-5-methoxy-4-nitrophenyl)-1-methyl-5-(trifluoromethyl)-1H-pyrazole in 50 ml of acetic acid was added 1.39 g (0.0249 mol) of iron powder. The reaction mixture was heated near reflux for 2 hours, treated with 1.39 g of iron powder, and heated at near reflux for another hour. After cooling, concentrating and chromatography, 3.54 g of 4-chloro-3-(4-amino-2-fluoro-5-methoxyphenyl)-1-methyl-5-(trifluoromethyl)-1H-pyrazole was isolated.

B. 3.064 g of 4-chloro-3-(4-amino-2-fluoro-5-methoxyphenyl)-1-methyl-5-(trifluoromethyl)-1H-pyrazole was dissolved in 50 ml of anhydrous acetonitrile and 1.90 g of anhydrous cupric chloride added. 1.93 ml of t-butyl nitrite (tech., 90%) dissolved in 10 ml of anhydrous acetonitrile was then added dropwise over 10 minutes, stirred an additional 20 minutes and then concentrated. The residue was taken up in ethyl acetate, extracted 3 times with 10% aqueous HCl, dried with anhydrous magnesium sulfate, filtered, concentrated and chromatographed to give 2.10 g of 4-chloro-3-(4-chloro-2-fluoro-5-methoxyphenyl)-1-methyl-5-(trifluoromethyl)-1H-pyrazole, mp. 70°–71° C.

Anal. Calc. for $C_{12}H_8N_2O_1Cl_1F_4$: C,42.01%; H,2.35%; N,8.16%. Found: C,42.15%; H,2.34%; N,8.18%.

EXAMPLE 17

This example describes the preparation of 2-chloro-5-(4-chloro-1-methyl-5-(trifluoromethyl)-1H-pyrazol-3-yl)-4-fluoro-N-methyl-N-propylbenzenamine (Compound No. 166).

A. A solution of 5.2 g (0.013 mole) 5-(4-chloro-1-methyl-5-(trifluoromethyl)-1H-pyrazol-3-yl)-4-fluoro-N-methyl-2-nitro-N-propylbenzenamine in 100 mL acetic acid was heated to 80° C. under a nitrogen atmosphere. The heat and nitrogen were removed and 2.2 g (0.039) mole iron powder was added in 3 portions over 5 min. The solution was stirred at 80° C. for an additional 30 min. The solution was cooled and filtered through Celite®. The filtrate was diluted with 100 mL water and extracted three times with ethyl acetate. The ethyl acetate extracts were washed with a saturated NaHCO₃ solution, dried over anhydrous MgSO₄, and concentrated in vacuo. The residue was purified chromatographically using 30% ethyl acetate in hexane as the eluent to give 3.85 g (80%) of 5-(4-chloro-1-methyl-5-(trifluoromethyl)-1H-pyrazol-3-yl)-4-fluoro-N-methyl-N-propyl-1,2-benzenediamine as a light yellow oil, $n_D^{25}$1.5352.

Anal. Calc. for $C_{15}H_{17}Cl_1F_4N_4$: C,49.39; H,4.70; N,15.36. Found: C,49.40; H,4.64; N,15.16.

B. All equipment was flame dried under nitrogen. A solution of 3.35 g (9.2 mmole) of the product of step A in 60 mL acetonitrile at 25° C. was treated with 0.9 g (9.2 mole) CuCl and 1.8 g (13.3 mmole) CuCl₂. A solution of 2.2 mL (18.4 mmole) 90% t-butyl nitrite was added over 5 minutes. After 2 hours at 28° C. the reaction mixture was stripped in vacuo. The reaction residue was taken up in ethyl acetate and washed three times with a 10% HCl solution, two times with brine and dried over anhydrous MgSO₄, and concentrated in vacuo. The residue was purified chromatographically using 20% ethyl acetate in hexane as the eluent to give 2.45 g (70%) of 2-chloro-5-(4-chloro-1-methyl-5-(trifluoromethyl)-1H-pyrazol-3-yl)-4-fluoro-N-methyl-N-propylbenzenamine as a clear colorless oil, $n_D^{25}$1.5030.

Anal. Calc. for $C_{15}H_{15}Cl_2F_4N_3$: C,46.89; H,3.94; N,10.94. Found: C,46.84; H,3.83; N,10.93.

EXAMPLE 18

This example describes the preparation of 4-bromo-3-(4-chloro-2-fluoro-5-methoxyphenyl)-1-methyl-5-(trifluoromethyl)-1H-pyrazole (Compound No. 313).

A. A solution of 3.16 g (7.9 mmole) 4-bromo-3-(2-fluoro-5-methoxy-4-nitrophenyl)-1-methyl-5-(trifluoromethyl)-1H-pyrazole in 59 mL acetic acid was heated to 80° C. under a nitrogen atmosphere. The heat and nitrogen were removed and 1.76 g (31.6 mmole) iron powder was added in 3 portions over 5 min. The solution was stirred at 80° C. for an additional 30 min. The solution was cooled and filtered through Celite®. The filtrate was diluted with 100 mL water and extracted three times with diethyl ether. The ether extracts were washed with brine, dried over anhydrous MgSO₄, and concentrated in vacuo. The residue was purified chromatographically using 40% ethyl acetate in hexane as the eluent to give 2.4 g (83%) of 4-(4-bromo-1-methyl-5-(trifluoromethyl)-1H-pyrazol-3-yl)-5-fluoro-2-methoxybenzeneamine as a white solid, mp 85°–86° C.

Anal. Calc. for $C_{12}H_{10}Br_1F_4N_3O_1$: C,39.15; H,2.74; N,11.41. Found: C,39.13; H,2.74; N,11.40.

B. All equipment was flame dried under nitrogen. A solution of 6.6 g (0.0179 mole) of the product of step A in 100 mL acetonitrile was cooled to 5° C. 1.8 g (0.018 mole) CuCl and 3.7 g (0.027 mole) CuCl₂ were added at 5° C. A solution of 4.8 mL (0.036 mole) 90% t-butyl nitrite in 15 mL acetonitrile was added over 15 minutes. The reaction mixture was stirred at 5° C. for 15 minutes and then allowed to warm to 28° C. After 2 hours at 28° C. the reaction mixture was stripped in vacuo. The reaction residue was taken up in diethyl ether and washed three times with a 10% HCl solution, two times with brine and dried over anhydrous MgSO₄, and concentrated in vacuo. The residue was purified chromatographically using 20% ethyl acetate in hexane as the eluent to give 6.3 g (91%) of 4-bromo-3-(4-chloro-2-fluoro-5-methoxyphenyl)-1-methyl-5-(trifluoromethyl)-1H-pyrazole as a white solid, mp 85°–86° C.

Anal. Calc. for $C_{12}H_8Br_1Cl_1F_4N_2O_1$: C,37.19; H,2.08; N,7.23. Found: C,37.23; H,2.08; N,7.24.

EXAMPLE 19

This example describes the preparation of 4-chloro-3-(5-chloro-2,4-difluorophenyl)-1-methyl-5-(trifluoromethyl)-1H-pyrazole (Compound No. 354).

A. A solution of 3.4 g (0.01 mole) 4-chloro-3-(2,4-difluoro-5-nitrophenyl)-1-methyl-5-(trifluoromethyl)-1H-pyrazole in 50 mL acetic acid was heated to 80° C. under a nitrogen atmosphere. The heat and nitrogen were removed and 1.7 g (0.03 mole) iron powder was added in 3 portions over 5 min. The solution was stirred at 80° C. for an additional 30 min. The solution was cooled and filtered through Celite®. The filtrate was diluted with 100 mL water and extracted three times with ethyl acetate. The ethyl acetate extracts were washed with a saturated NaHCO$_3$ solution, dried over anhydrous MgSO$_4$, and concentrated in vacuo. The residue was purified chromatographically using 35% ethyl acetate in hexane as the eluent to give 2.46 g (79%) of 5-(4-chloro-1-methyl-5-(trifluoromethyl)-1H-pyrazol-3-yl)-2,4-difluorobenzenamine as a white solid, mp 82° C.

Anal. Calc. for $C_{11}H_7Cl_1F_5N_3$: C,42.40; H,2.26; N,13.48. Found: C,42.40; H,2.26; N,13.49.

B. All equipment was flame dried under nitrogen. A solution of 2.0 g (6.4 mmole) of the product of step A in 50 mL acetonitrile at 25° C. was treated with 0.63 g (6.4 mmole) CuCl and 1.2 g (9.4 mmole) of CuCl$_2$. A solution of 1.74 mL (5.0 mmole) 90% t-butyl nitrite was added over 5 minutes. After 4 hours at 28° C. the reaction mixture was stripped in vacuo. The reaction residue was taken up in ethyl acetate and washed three times with a 10% HCl solution, two times with brine and dried over anhydrous MgSO$_4$, and concentrated in vacuo. The residue was purified chromatographically using 10% ethyl acetate in hexane as the eluent to give 1.63 g (78%) of 4-chloro-3-(5-chloro-2,4-difluorophenyl)-1-methyl-5-(trifluoromethyl)-1H-pyrazole as a white solid, mp 50°–51° C.

Anal. Calc. for $C_{11}H_5Cl_2F_5N_2$: C,39.91; H,1.52; N,8.46. Found: C,39.89; H,1.52; N,8.39.

Examples 20 and 21 describe working embodiments of Process VI.

EXAMPLE 20

This example describes the preparation of 4-chloro-3-(4-chloro-2-fluoro-5-hydroxyphenyl)-1-methyl-5-(hydroxyphenyl)-1-methyl-5-(trifluoromethyl)-1H-pyrazole (Compound No. 325).

1.39 g of 4-chloro-3-(4-chloro-2-fluoro-5-methoxyphenyl)-1-methyl-5-(trifluoromethyl)-1H-pyrazole was dissolved in 80 ml of anhydrous methylene chloride and then cooled with a dry ice/acetone bath and 0.14 ml of boron tribromide added. After allowing to warm to room temperature, the mixture was treated with an additional 0.28 ml of boron tribromide. Added was an additional 1.0 ml of boron tribromide and stirred at room temperature for 6 hours. After stirring, 30–50 ml of ice cooled water was added and the mixture stirred for 10 minutes. The organic phase was extracted with water, dried with anhydrous magnesium sulfate, filtered and concentrated to give 1.28 g of 4-chloro-3-(4-chloro-2-fluoro-5-hydroxyphenyl)-1-methyl-5-(trifluoromethyl)-1H-pyrazole, m.p. 123.0°–126.0° C.

Anal. Calc. for $C_{11}H_6N_2O_1Cl_2F_4$: C,40.15; H,1.84; N,8.51. Found: C,40.08; H,1.87; N,8.48.

EXAMPLE 21

This example describes the preparation of 4-(4-chloro-1-methyl-5-(trifluoromethyl)-1H-pyrazol-3-yl)-5-fluoro-2-nitrophenol (Compound No. 429).

A solution of 1.4 g (4 mmole) 4-chloro-3-(2-fluoro-4-methoxy-5-nitrophenyl)-1-methyl-5-(trifluoromethyl)-1H-pyrazole in 20 mL methylene chloride was chilled to 0° C. Next 5.0 mL of a 1M methylene chloride solution of BBr$_3$ (4.9 mmole) was added slowly over 10 minutes. The solution was allowed to stir overnight at room temperature. The solution was washed two times with water, dried over anhydrous MgSO$_4$, and concentrated in vacuo. The residue was recrystallized from hexane to give 0.7 g (54%) of 4-(4-chloro-1-methyl-5-(trifluoromethyl)-1H-pyrazol-3-yl)-5-fluoro-2-nitrophenol as a beige solid, mp 89°–90° C.

Anal. Calc. for $C_{11}H_6Cl_1F_4N_3O_3$: C,38.90; H,1.78; N,12.37. Found: C,38.93; H,1.78; N,12.16.

Examples 22 through 24 describe specific working embodiments of Process VII.

EXAMPLE 22

This example describes the preparation of 4-chloro-3-(4-chloro-2-fluoro-5-progargyloxyphenyl)-1-methyl-5-(trifluoromethyl)-1H-pyrazole (Compound No. 261).

1.01 g of 4-chloro-3-(4-chloro-2-fluoro-5-hydroxyphenyl)-1-methyl-5-(trifluoromethyl)-1H-pyrazole, 0.44 g of anhydrous potassium carbonate and 0.5 mL of propargyl bromide (80% by wt. in toluene) were dissolved in 20–30 mL of anhydrous DMF. The mixture was heated at 65° C. for 90 minutes. After cooling, the mixture was diluted with water and then extracted three times with ether. The combined ether extracts were extracted twice with water, dried with anhydrous magnesium sulfate, filtered, concentrated and chromatographed to give 1.05 g of 4-chloro-3-(4-chloro-2-fluoro-5-progargyloxyphenyl)-1-methyl-5-(trifluoromethyl)-1H-pyrazole, mp. 89.5°–91.0° C.

Anal. Calc. for $C_{14}H_8N_2O_1Cl_2F_4$: C,45.80%; H,2.20%; N,7.63%. Found: C,45.93%; H,2.21%; N,7.61%.

EXAMPLE 23

This example describes the preparation of (4-(4-chloro-1-methyl-5-(trifluoromethyl)-1H-pyrazol-3-yl)-5-fluoro-2-nitrophenoxy)acetic acid, ethyl ester (Compound No. 386).

At 25° C., 6.11 g (0.018 mole) 4-(4-chloro-1-methyl-5-(trifluoromethyl)-1H-pyrazol-3-yl)-5-fluoro-2-nitrophenol, 2.5 g (0.019 mole) K$_2$CO$_3$, and 2.0 mL (0.019 mole) ethyl bromoacetate were slurried in 100 mL acetone. The reaction mixture was stirred at 40° C. for 4 hours. The mixture was cooled, diluted with 100 mL cold water, and extracted four times with ethyl acetate. The ethyl acetate extracts were washed with brine, dried over anhydrous MgSO$_4$, and stripped in vacuo. The residue was recrystallized from methylcyclohexane to give 7.5 g (99%) of (4-(4-chloro-1-methyl-5-(trifluoromethyl)-1H-pyrazol-3-yl)-5-fluoro-2-nitrophenoxy)acetic acid, ethyl ester as a light yellow solid, mp 95°–96° C.

Anal. Calc. for $C_{15}H_{12}Cl_1F_4N_3O_5$: C,42.32; H,2.84; N,9.87. Found: C,42.30; H,2.83; N,9.85.

EXAMPLE 24

This example describes the preparation of (2-chloro-5-(4-chloro-1-methyl-5-(trifluoromethyl)-1H-pyrazol-3-yl)-4-fluorophenoxy)acetic acid, ethyl ester (Compound No. 290).

At 25° C., 13.16 g (0.04 mole) 4-chloro-3-(4-chloro-2-fluoro-5-hydroxyphenyl)-1-methyl-5-(trifluoromethyl)-1H-pyrazole, 6.1 g (0.044 mole) K$_2$CO$_3$, and 4.8 mL (0.044 mole) ethyl bromoacetate were slurried in 25 mL acetone. The reaction mixture was stirred at 25° C. for 16 hours. The reaction solution was poured into 150 mL ice water, filtered, washed with water and air dried. The residue was recrystallized from hexane to give 16.6 g (100%) of (2-chloro-5-(4-chloro-1-methyl-5-(trifluoromethyl)-1H-pyrazol-3-yl)-4- fluorophenoxy)acetic acid, ethyl ester as a white solid, mp 130°–131° C.

Anal. Calc. for $C_{15}H_{12}Cl_2F_4N_2O_3$: C,43.40; H,2.91; N,6.75. Found: C,43.54; H,2.91; N,6.77.

Examples 25 and 26 describe specific working embodiments of Process VIII.

EXAMPLE 25

This example describes the preparation of 2-(2-chloro-5-(4-chloro-1-methyl-5-(trifluoromethyl)-1H-pyrazol-3-yl)-4-fluorophenoxy)-N-methyl-propanamide (Compound No. 237).

A. To a slurry of 1.4 g (3.3 mmole) 2-(2-chloro-5-(4-chloro-1-methyl-5-(trifluoromethyl)-1H-pyrazol-3-yl)-4-fluorophenoxy)-propanoic acid, ethyl ester in 50 mL water and 30 mL 1,4-dioxane was added 1.3 mL (3.3 mmole) of a 10% NaOH solution. After 30 minutes, the solution was cooled and the pH adjusted to 3 with concentrated HCl. The reaction mixture was extracted with diethyl ether. The ether solution was washed with water, dried over anhydrous $MgSO_4$, and concentrated in vacuo. The residue was recrystallized from methylcyclohexane to give 1.3 g (100%) of 2-(2-chloro-5-(4-chloro-1-methyl-5-(tri-fluoromethyl)-1H-pyrazol-3-yl)-4-fluorophenoxy)propanoic acid as a white solid, mp 150°–151° C.

Anal. Calc. for $C_{14}H_{10}Cl_2F_4N_2O_3$: C,41.92; H,2.51; N,6.98. Found: C,41.96; H,2.48; N,7.00.

B. To a solution of 0.8 g (2.0 mmole) of the product of step A in 100 mL methylene chloride was added 0.5 mL (6.0 mmole) oxalyl chloride over 5 minutes, causing the evolution of gas. When this evolution ceased, one drop of DMF was added and the solution stirred until the gas evolution ceased. The solution was stripped to dryness in vacuo. The residue was dissolved in 10 mL THF and added to a solution of 5 mL 40% aqueous methyl amine and 10 mL THF at 0° C. over 5 minutes. The reaction mixture was allowed to stir for 30 minutes at room temperature. The solution was diluted with 100 mL cold water and extracted with ethyl acetate. The ethyl acetate was washed with brine, dried over anhydrous $MgSO_4$ and concentrated in vacuo. The solid was recrystallized from methylcyclohexane to give 0.83 g (99%) of 2-(2-chloro-5-(4-chloro-1-methyl-5-(trifluoromethyl)-1H-pyrazol-3-yl)-4-fluorophenoxy)-N-methylpropanamide as a white solid, mp 134.5°–135.5° C.

Anal. Calc. for $C_{15}H_{13}Cl_2F_4N_3O_2$: C,43.50; H,3.16; N,10.16. Found: C,43.70; H,3.16; N,10.20.

EXAMPLE 26

This example describes the preparation of 2-(2-chloro-5-(4-chloro-1-methyl-5-(trifluoromethyl)-1H-pyrazol-3-yl)-4-fluorophenoxy)propanoic acid, 3-methylbutyl ester (Compound No. 288).

To a solution of 1.9 g (5.0 mmole) of 2-(2-chloro-5-(4-chloro-1-methyl-5-(trifluoromethyl)-1H-pyrazol-3-yl)-4-fluorophenoxy)-propanoic acid in 50 mL methylene chloride was added 1.3 mL (15.0 mmole) oxalyl chloride over 5 minutes, causing the evolution of gas. When this evolution ceased, one drop of DMF was added and the solution stirred until the gas evolution ceased. The solution was stripped to dryness in vacuo. The acid chloride was dissolved in 40 mL of 3-methyl-1-butanol and heated to reflux for one hour. The reaction mixture was cooled, diluted with 100 mL cold water and extracted with ethyl acetate. The ethyl acetate was washed with brine, dried over anhydrous $MgSO_4$ and concentrated in vacuo. The residue was purified chromatographically using 25% ethyl acetate in hexane as the eluent to give 2.17 g (95%) of 2-(2-chloro-5-(4-chloro-1-methyl-5-(trifluoromethyl)-1H-pyrazol-3-yl)-4-fluorophenoxy)-propanoic acid, 3-methylbutyl ester as a white solid; mp 128° C.

Anal. Calc. for $C_{18}H_{18}Cl_2F_4N_2O_3$: C,47.28; H,3.97; N,6.13. Found: C,47.32; H,3.95; N,6.17.

EXAMPLE 27

This example describes the preparation of 2H-1,4-benzoxazin-3(4H)-one, 6-(4-chloro-1-methyl-5-(trifluoromethyl)-1H-pyrazol-3-yl)-7-fluoro-4-(2-propynyl)-2H-1,4-benzoxazin-3(4H)-one (Compound No. 446) and is a specific embodiment of Process IX.

A. A solution of 4.5 g (0.0106 mole) (4-(4-chloro-1-methyl-5-(trifluoromethyl)-1H-pyrazol-3-yl)-5-fluoro-2-nitrophenoxy)-acetic acid, ethyl ester in 75 mL acetic acid was heated to 80° C. under a nitrogen atmosphere. The heat and nitrogen were removed and 1.8 g (0.033 mole) iron powder was added in 3 portions over 5 min. The solution was stirred at 80° C. for an additional 3 hours. The solution was cooled and filtered through Celite®. The filtrate was diluted with 100 mL water and extracted three times with ethyl acetate. The ethyl acetate extracts were washed with a saturated $NaHCO_3$ solution, dried over anhydrous $MgSO_4$, and concentrated in vacuo. The residue was recrystallized from methylcyclohexane/ethyl acetate to give 2.95 g (80%) of 6-(4-chloro-1-methyl-5-(trifluoromethyl)-1H-pyrazol-3-yl)-7-fluoro-2H-1,4-benzoxazin-3(4H)-one as a white solid, mp 207° C.

Anal. Calc. for $C_{13}H_8Cl_1F_4N_3O_2$: C,44.65; H,2.31; N,12.02. Found: C,44.66; H,2.31; N,11.97.

B. At 25° C., 3.0 g (8.6 mmole) of the product of step A, 1.22 g (6.0 mmole) $K_2CO_3$ and 0.79 mL (8.8 mmole) 80% propargyl bromide were slurried in 50 mL acetone. The reaction was stirred at 40° C. for 6 hours. The reaction was cooled, diluted with 100 mL cold water, and extracted four times with ethyl acetate. The ethyl acetate extracts were washed with brine, dried over anhydrous $MgSO_4$, and stripped in vacuo. The residue was recrystallized from methylcyclohexane to give 2.97 g (89%) of 2H-1,4-benzoxazin-3(4H)-one, 6-(4-chloro-1-methyl-5-(trifluoromethyl)-1H-pyrazol-3-yl)-7-fluoro-4-(2-propynyl)-2H-1,4-benzoxazin-3(4H)-one as a beige solid, mp 142°–143° C.

Anal. Calc. for $C_{16}H_{10}Cl_1F_4N_3O_2$: C,49.57; H,2.60; N,10.84. Found: C,49.58; H,2.62; N,10.85.

EXAMPLE 28

This example describes the preparation of 7-(4-chloro-1-methyl-5-(trifluoromethyl)-1H-pyrazol-3-yl)-6-fluoro-4-(2-propynyl)-2H-1,4-benzoxazin-3(4H)-one (Compound No. 479) and is a specific embodiment of Process X.

A. A solution of 2.3 g (5.4 mmole) (5-(4-chloro-1-methyl-5-(trifluoromethyl)-1H-pyrazol-3-yl)-4-fluoro-2-nitrophenoxy)acetic acid, ethyl ester in 50 mL acetic acid was heated to 80° C. under a nitrogen atmosphere. The heat and nitrogen were removed and 0.9 g (16.2 mmole) iron powder was added in 3 portions over 5 minutes. The solution was stirred at 80° C. for an additional 50 minutes. The solution was cooled and filtered through Celite®. The filtrate was diluted with 100 mL water and extracted three times with ethyl acetate. The ethyl acetate extracts were washed with a saturated $NaHCO_3$ solution, dried over anhydrous $MgSO_4$ and concentrated in vacuo. The residue was recrystallized from methylcyclohexane/ethyl acetate to give 0.96 g (50%) of 7-(4-chloro-1-methyl-5-(trifluoromethyl)-1H-pyrazol-3-yl)-6-fluoro-2H-1,4-benzoxazin-3(4H)-one as a white solid, mp 242° C.

Anal. Calc. for $C_{13}H_8Cl_1F_4N_3O_2$: C,44.65; H,2.31; N,12.02. Found: C,44.61; H,2.27; N,11.99.

B. At 25° C., 2.7 g (7.7 mmole) the product of step A, 1.1 g (8.0 mmole) $K_2CO_3$ and 0.9 mL (8.0 mmole) 80% propargyl bromide were slurried in 25 mL DMSO. The mixture was stirred at 45° C. for 16 hours. The mixture was cooled, diluted with 100 mL cold water and extracted four times with ethyl acetate. The ethyl acetate extracts were washed with brine, dried over anhydrous $MgSO_4$ and stripped in vacuo. The residue was purified chromatographically using methylene chloride as the eluent to give 2.7 g (90%) of 7-(4-chloro-1-methyl-5-(trifluoromethyl)-1H-pyrazol-3-yl)-6-fluoro-4-(2-propynyl)-2H-1,4-benzoxazin-3(4H)-one as a white solid, mp 184° C.

Anal. Calc. for $C_{16}H_{10}Cl_1F_4N_3O_2$: C,49.57; H,2.60; N,10.84. Found: C,49.48; H,2.56; N,10.95.

EXAMPLE 29

This example describes the preparation of cis- and trans-4-chloro-3-(3-(chloromethylene) -5-fluoro-2,3-dihydro-6-benzofuranyl)-1-methyl-5-(trifluoromethyl)-1H-pyrazole (Compound Nos. 481 and 482) and is a specific embodiment of Process XI.

All equipment was flame dried under nitrogen. A solution of 2.0 g (5.75 mmole) 4-(4-chloro-1-methyl-5(trifluoromethyl)-1H-pyrazol-3-yl)-5-fluoro-2-(2-propynloxy)-benzeneamine in 100 mL acetonitrile at 25° C. was treated with 0.6 g (5.75 mmole) CuCl and 0.8 g (5.75 mmole) $CuCl_2$. A solution of 1.1 mL (8.6 mmole) 90% t-butyl nitrite was added over 5 minutes. After 6 hours at 28° C. the reaction mixture was stripped in vacuo. The reaction residue was taken up in ethyl acetate and washed three times with a 10% HCl solution, two times with brine and dried over anhydrous $MgSO_4$ and concentrated in vacuo. The residue was purified chromatographically using 20% ethyl acetate in hexane as the element to give 0.73 g (35%) of cis-4-chloro-3-(3-(chloromethylene)-5-fluoro-2,3-dihydro-6-benzofuranyl)-1-methyl-5-(trifluoromethyl)-1H-pyrazole as a white solid, mp 140.5°–142.5° C.

Anal. Calc. for $C_{14}H_8Cl_2F_4N_2O_1$: C,45.80; H,2.20; N,7.63; $C_{1,19.31}$. Found: C,45.64; H,2.22; N,7.60; Cl,19.29.

The chromatography described above gave a second fraction following the main component. This fraction was collected, stripped and the residue crystallized from hexanes to give 0.68 g (32% yield) of trans-4-chloro-3-(3-(chloromethylene)-5-fluoro-2,3-dihydro-6-benzo-furanyl)-1-methyl-5-(trifluoromethyl)-1H-pyrazole as a beige solid, mp 132°–135° C.

Anal. Calc. for $C_{14}H_8Cl_2F_4N_2O_1$: C,45.80; H,2.20; N,7.63; Cl,19.31. Found: C,45.71; H,2.23; N,7.63; Cl,19.28.

Examples 30 through 37 describe working embodiments of Process XII.

EXAMPLE 30

This example describes the preparation of 3-[5-(bromomethyl)-4-chloro-2-fluorophenyl]-4-chloro-1-methyl-5-(trifluoromethyl)-1H-pyrazole (Compound No. 108).

A slurry of 3-[5-methyl-4-chloro-2-fluorophenyl]-4-chloro-1-methyl-5-(trifluoromethyl)-1H-pyrazole (25 g, 76.4 mmole) and N-bromosuccinimide (13.6 g, 76.4 mmole) in 100 ml of carbon tetrachloride in a 500 ml round bottomed flask equipped with a magnetic stirrer was treated with a catalytic amount of benzoyl peroxide. The temperature was raised to reflux for one hour. The reaction mixture was cooled to room temperature, filtered and concentrated to give 31.5 g of white solid. The material was recrystallized twice from hexanes to afford 15.3 g (49%) of 3-[5-(bromomethyl)-4-chloro-2fluorophenyl]-4-chloro-1-methyl-5-(trifluoromethyl)-1H-pyrazole as a white solid; mp 112°–114° C.

Anal. Calc. for $C_{12}H_7N_2F_4Cl_2Br_1$: C,35.50; H,1.74; N,6.90. Found: C,35.57; H,1.76; N,6.88.

EXAMPLE 31

This example describes the preparation of (((2-chloro-5-(4-chloro-1-methyl-5-(trifluoromethyl)-1H-pyrazol-3-yl)-4-fluorophenyl)methyl)thio)acetic acid, ethyl ester (Compound No. 123).

A mixture of 1.62 g (4.0 mmole) 3-[5-(bromomethyl)-4-chloro-2-fluorophenyl]-4-chloro-1-methyl-5-(trifluoromethyl)-1H-pyrazole, 0.44 mL ethyl mercaptoacetate and 0.55 g $K_2CO_3$ was slurried in 25 mL of acetone. The reaction mixture was allowed to stir at room temperature overnight. After dilution with 100 mL of cold water, the mixture was extracted with ethyl acetate, the organic extracts washed with water, dried with $MgSO_4$ and concentrated in vacuo. The residue was purified by chromatography to afford 1.7 g (96%) of (((2-chloro-5-(4-chloro-1-methyl-5-(trifluoromethyl) -1H-pyrazol-3-yl) -4-fluorophenyl)methyl)thio)acetic acid, ethyl ester as a white solid; mp 63° C.

Anal. Calc. for $C_{16}H_{14}Cl_2F_4N_2O_2S_1$: C,43.16; H,3.17; N,6.29. Found: C,43.16; H,3.16; N,6.27.

EXAMPLE 32

This example describes the preparation of 2-chloro-5-[4-chloro-1-methyl-5-(trifluoromethyl)-1H-pyrazol-3-yl]-4-fluorobenzenemethanol (Compound No. 122).

To a solution of 7.1 g (0.0175 mole) 3-[5-(bromomethyl)-4-chloro-2-fluorophenyl]-4-chloro-1-methyl-5-(trifluoromethyl)-1H-pyrazole in 20 mL DMF was added 1.5 g (0.018 mole) sodium acetate. The mixture was stirred for 12 hours at 25° C. The mixture was poured into 100 mL cold water and the solid filtered and dried. The product was recrystallized from ethanol/-water to give 6.0 g (90%) of 2-chloro-5-(4-chloro-1-methyl-5-(trifluoromethyl)-1H-pyrazol-3-yl)-4-fluorobenzenemethanol, acetate (ester), mp 90° C. The acetate was dissolved in 10 mL 1,4-dioxane and 10 mL water and 6.3 mL (0.0158 mole) 10% NaOH solution was added. After 30 minutes the solution was neutralized with concentrated HCl, filtered and the solid dried. The solid was recrystallized from ethanol/water to give 5.4 g (99%) of 2-chloro-5-[4-chloro-1-methyl-5-(trifluoromethyl)-1H-pyrazol-3-yl]-4-fluorobenzenemethanol as a white solid; mp 103° C.

Anal. Calc. for $C_{12}H_8N_2O_1F_4Cl_2$: C,42.01; H,2.35; N,8.16. Found: C,41.88; H,2.34; N,8.09.

EXAMPLE 33

This example describes the preparation of ((2-chloro-5-(4-chloro-1-methyl-5-(trifluoromethyl)-1H-pyrazol-3-yl)-4-fluorophenyl)methoxy)acetic acid, 1-methylethylester (Compound No. 119).

At 25° C., 1.7 g (5.0 mmole) 2-chloro-5-[4-chloro-1-methyl-5-(trifluoromethyl)-1H-pyrazol-3-yl]-4-fluorobenzenemethanol, 0.8 g (5.5 mmole) $K_2CO_3$ and 0.7 mL (5.5 mmole) isopropyl bromoacetate were slurried in 15 mL DMSO. The mixture was stirred overnight at 45° C. The mixture was cooled, diluted with 100 mL cold water and extracted four times with ethyl acetate. The ethyl acetate extracts were washed with brine, dried over anhydrous $MgSO_4$ and stripped in vacuo. The residue was purified chromatographically using 10% ethyl acetate in hexane as the eluent to give 0.9 g (41%) of ((2-chloro-5-(4-chloro-1-methyl-5-(trifluoromethyl)-1H-pyrazol-3-yl)-4-fluorophenyl)methoxy)acetic acid, 1-methylethyl ester as a white solid; mp 55° C.

Anal. Calc. for $C_{17}H_{16}Cl_2F_4N_2O_3$: C,46.07; H,3.64; N,6.32. Found: C,46.21; H,3.69; N,6.11.

EXAMPLE 34

This example describes the preparation of 4-chloro-3-[4-chloro-5-(dibromomethyl)-2-fluorophenyl]-1-methyl-5-(trifluoromethyl)-1H-pyrazole (Compound No. 132).

In a 250 ml round bottomed flask equipped with a magnetic stirrer, a slurry of 3-[5-methyl-4-chloro-2fluorophenyl]-4-chloro-1-methyl-5-(trifluoromethyl)-1H-pyrazole (8.18 g, 25mmole) and N-bromosuccinimide (8.9 g, 50.0 mmole) was prepared in 50 ml of carbon tetrachloride. A catalytic amount of benzoyl peroxide was added and the temperature was raised to reflux and held for 3.5 hours. The reaction mixture was cooled to room temperature, filtered and concentrated. The residue was purified by chromatography to afford 10.36 g (85%) of 4-chloro-3-[4-chloro-5-(dibromomethyl)-2-fluorophenyl]-1-methyl-5-(tri-fluoromethyl)-1H-pyrazole as a white solid; mp 89°–92° C.

Anal. Calc. for $C_{12}H_6N_2F_4Cl_2Br_2$: C,29.72; H,1.25; N,5.78. Found: C,29.72; H,1.25; N,5.78.

EXAMPLE 35

This example describes the preparation of 2-chloro-5-[4-chloro-1-methyl-5-(trifluoromethyl)-1H-pyrazol-3-yl]-4-fluorobenzaldehyde (Compound No. 133).

In a 100 ml round bottomed flask equipped with a magnetic stirrer, 4-chloro-3-[4-chloro-5-(dibromomethyl)-2-fluorophenyl]-1-methyl-5-(trifluoromethyl)-1H-pyrazole (5.0 g, 10.3 mmole) was stirred for 30 minutes in 20 ml of sulfuric acid. The resulting clear yellow solution was allowed to stand at room temperature for 10 days, stirred briefly to remove color, and poured onto 200 ml of ice/water. The aqueous mixture was extracted with ether and the organic layer was dried with $MgSO_4$, filtered and concentrated to give 3.15 g of white solid which was recrystallized from cold hexanes to afford 2.5 g (71%) of 2-chloro-5-[4-chloro-1-methyl-5-(trifluoromethyl)-1H-pyrazol-3-yl]-4-fluorobenzaldehyde as a white solid; mp 70°–72° C.

Anal. Calc. for $C_{12}H_6N_2O_1F_4Cl_2$: C,42.26; H,1.77; N,8.21. Found: C,42.22; H,1.78; N,8.24.

EXAMPLE 36

This example describes the preparation of 2-chloro-5-[4-chloro-1-methyl-5-(trifluoromethyl)-1H-pyrazol-3-yl]-4-fluorobenzoic acid (Compound No. 149).

To a solution of 2-chloro-5-[4-chloro-1-methyl-5-(trifluoromethyl)-1H-pyrazol-3-yl]-4-fluorobenzaldehyde (4.5 g, 13.2 mmole) in 40 ml of acetone was added 13 ml (26 mmole) of Jones' reagent. The solution was stirred at ambient temperature for 2 hours and poured into 400 ml of water. The resulting solid was filtered and air dried overnight to afford 4.5 g (96%) of 2-chloro-5-[4-chloro-1-methyl-5-(trifluoromethyl)-1H-pyrazol-3-yl]-4-fluoro-benzoic acid as a white solid. An analytical sample was recrystallized from ether/hexanes; mp 179°–181° C.

Anal. Calc. for $C_{13}H_6N_2O_2F_4Cl_2$: C,40.36; H,1.69; N,7.84. Found: C,40.49; H,1.74; N,7.77.

EXAMPLE 37

This example describes the preparation of 2-chloro-5-[4-chloro-1-methyl-5-(trifluoromethyl)-1H-pyrazol-3-yl]-4-fluorobenzoic acid, 1-methylethyl ester (Compound No. 135).

To a solution of 4.3 g (0.012 mole) 2-chloro-5-(4-chloro-1-methyl-5-(trifluoromethyl)-1H-pyrazol-3-yl)-4-fluorobenzoic acid in 50 mL methylene chloride was added 3.1 mL (0.036 mole) oxalyl chloride causing the evolution of gas. When this evolution ceased, one drop of DMF was added and the solution stirred until the gas evolution ceased. The solution was concentrated in vacuo and the resultant residue dissolved in 25 mL isopropanol and heated to 60° C. for 1 hour. The solution was cooled, poured into 200 mL cold water and the solid filtered and dried. The product was recrystallized from ethanol/water to yield 1.69 g (70%) of 2-chloro-5-[4-chloro-1-methyl-5-(trifluoromethyl)-1H-pyrazol-3-yl]-4fluorobenzoic acid, 1-methylethyl ester as a white solid; mp 69° C.

Anal. Calc. for $C_{15}H_{12}Cl_2F_4N_2O_2$: C,45.13; H,3.03; N,7.02. Found: C,45.14; H,3.04; N,7.03.

Examples 38 and 39 describe working embodiments of Process XIII.

EXAMPLE 38

This example describes the preparation of 2-chloro-5-[4-chloro-1-methyl-5-(trifluoromethyl)-1H-pyrazol-3-yl]-4-fluorobenzenesulfonyl chloride (Compound No. 346).

A solution of 4-chloro-3-(4-chloro-2-fluorophenyl)-1-methyl-5-(trifluoromethyl)-1H-pyrazole in 20 mL of chlorosulfonic acid was heated in a 120° C. oil bath for four hours and allowed to cool to room temperature. Methylene chloride was added and the solution added dropwise to a stirring mixture of ice and water (caution, extremely reactive). The layers were separated and the aqueous layer was washed with methylene chloride. The combined organic layers were dried with $MgSO_4$, filtered and concentrated and the resultant solid residue washed with a very small amount of ether and recrystallized from hexanes to afford 1.65 g (63%) of 2-chloro-5-[4-chloro-1-methyl-5-(trifluoromethyl)-1H-pyrazol-3-yl]-4-fluorobenzenesulfonyl chloride as a white solid; mp 116°–117° C.

Anal. Calc. for $C_{11}H_5N_2O_2S_1F_4Cl_3$: C,32.10; H,1.22; N,6.81; Cl,25.84. Found: C,32.15; H,1.17; N,6.76; Cl,25.77.

EXAMPLE 39

This example describes the preparation of 2-chloro-5-[4-chloro-1-methyl-5-(trifluoromethyl)-1H-pyrazol-3-yl]-4-fluorobenzenethiol (Compound No. 343).

To a solution of 12.8 g (0.031 mole) 2-chloro-5-[4-chloro-1-methyl-5-(trifluoromethyl)-1H-pyrazol-3-yl]-4-fluorobenzenesulfonyl chloride in 100 mL acetic acid was added 40.7 g (0.62 mole) zinc powder. The slurry was stirred at 80° C. for 4 hours, allowed to cool and filtered through Celite®.

The filtrate was poured into 1.0 L water, the solid filtered and dried. The solid was recrystallized from ethanol/water to give 10.2 g (95%) of 2-chloro-5-[4-chloro-1-methyl-5-(trifluoromethyl)-1H-pyrazol-3-yl]-4-fluorobenzenethiol as a yellow solid; mp 56°–58° C.

Anal. Calc. for $C_{11}H_6N_2S_1F_4Cl_2$: C,38.28; H,1.75; N,8.12. Found: C,38.29; H,2.02; N,8.12.

EXAMPLE 40

This example describes the preparation of 4-chloro-3-(4-chloro-5-(1,3-dioxolan-2-yl)-2-fluorophenyl)-1-methyl-5-(trifluoromethyl)-1H-pyrazole (Compound No. 100) and is a specific embodiment of Process XIV.

In an apparatus equipped with a Dean-Stark trap for azeotropic removal of water, 2.4 g (7.0 mmoles) 2-chloro-5-[4-chloro-1-methyl-5-(trifluoromethyl)-1H-pyrazol-3-yl]-4-fluorobenzaldehyde, 0.4 mL (7.7 mmoles) ethylene glycol and a catalytic amount of P-toluenesulfonic acid in 50 mL toluene was heated to reflux for 24 hours. The resultant mixture was concentrated and the residue purified by chromatography to give 1.65 g (61%) of 4-chloro-3-(4-chloro-5-(1,3-dioxolan-2-yl)-2-fluorophenyl)-1-methyl-5-(trifluoromethyl)-1H-pyrazole as a clear colorless oil; $n_D^{25}$1.5348.

Anal. Calc. for $C_{14}H_{10}Cl_2F_4N_2O_2$: C,43.66; H,262; N,7.27. Found: C,43.67; H,2.59; N,7.24.

EXAMPLE 41

This example describes the preparation of 3-(2-chloro-5-(4-chloro-1-methyl-5-(trifluoromethyl)-1H-pyrazol-3-yl)-4-fluorophenyl)propenoic acid, methyl ester (Compound No. 128) and is a specific embodiment of Process XV.

To a solution of 2.3 g (6.8 mmole) 2-chloro-5-[4-chloro-1-methyl-5-(trifluoromethyl)-1H-pyrazol-3-yl]-4-fluorobenzaldehyde in 25 mL methanol was added 2.27 g (6.8 mmole) methyl(triphenylphosphoranylidene)acetate, keeping the temperature below 35° C. The reaction mixture was allowed to stir for 15 minutes and diluted with ethyl acetate, washed with brine, dried over anhydrous $MgSO_4$, and concentrated in vacuo. The residue was purified chromatographically using 20% ethyl acetate in hexane as the eluent to give 2.0 g (74%) of 3-(2-chloro-5-(4-chloro-1-methyl-5-(trifluoromethyl)-1H-pyrazol-3-yl)-4-fluorophenyl)propenoic acid, methyl ester as a white solid; mp 117° C.

Anal. Calc. for $C_{15}H_{10}Cl_2F_4N_2O_2$: C,45.36; H,2.54; N,7.05. Found: C,45.41; H,2.59; N,7.03.

EXAMPLE 42

This example describes the preparation of (((((2-chloro-5-(4-chloro-1-methyl-5-(trifluoromethyl)-1H-pyrazol-3-yl)-4-fluorophenyl)methylene)amino)oxy)acetic acid (Compound No. 130) and is a specific embodiment of Process XVI.

A mixture of 3.4 g (0.01 mole) 2-chloro-5-[4-chloro-1-methyl-5-(trifluoromethyl)-1H-pyrazol-3-yl]-4-fluorobenzaldehyde, 2.73 g (0.0125 mole) carboxymethoxylamine hemihydrochloride and 1.03 g (0.0125 mole) sodium acetate in 50 mL ethanol was heated to reflux for 2 hours. The reaction mixture was allowed to cool, treated with 150 mL of water and the resultant precipitate collected and dried. The product was recrystallized from methylcyclohexane with a minimum amount of ethyl acetate to yield 3.35 g (81%) of ((((2-chloro-5-(4-chloro-1-methyl-5-(trifluoromethyl)-1H-pyrazol-3-yl)-4-fluorophenyl)methylene)amino)oxy)acetic acid as a white solid; mp 170° C.

Anal. Calc. for $C_{14}H_{19}Cl_2F_4N_3O_3$: C,40.60; H,2.19; N,10.15. Found: C,40.54; H,2.28; N,10.17.

Tables 4–6 show examples of compounds prepared according to Processes II–XVI. In Table 4 are listed examples of 1-methyl-5-arylpyrazole Compounds. In Table 5 are examples of 1-methyl-3-arylpyrazoles. Table 6 lists a variety of compounds, most of which include compounds wherein $R_6$ and $R_7$ are cyclized to form fused-ring heterocyclic structures.

TABLE 4

PHYSICAL DATA FOR 1-METHYL-5-ARYLPYRAZOLES

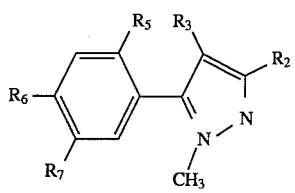

| Compound No. | $R_2$ | $R_3$ | $R_5$ | $R_6$ | $R_7$ | physical data (mp, bp, nD) |
|---|---|---|---|---|---|---|
| 62 | $CF_2H$ | Cl | F | H | F | nD, 1.5162 (25° C.) |
| 63 | $CF_3$ | Cl | F | Cl | $CH_3$ | 71.0–72.0° C. |
| 64 | $CF_2H$ | Cl | F | Cl | $CH_3$ | 91.0° C. |
| 65 | $CF_3$ | Cl | H | $NO_2$ | H | 122.5–123.5° C. |
| 66 | $CF_3$ | Cl | H | Cl | H | 68.9–69.6° C. |
| 67 | $CF_2Cl$ | Cl | H | Cl | H | 65.1–66.0° C. |
| 68 | $CF_3$ | Br | F | H | F | 53.0° C. |
| 69 | $CF_3$ | Cl | F | H | F | 69.0° C. |
| 70 | $CF_3$ | Cl | F | $NO_2$ | F | 88.0° C. |
| 71 | $CF_3$ | Cl | F | $OCH_3$ | F | nD 1.5062 (25° C.) |
| 72 | $CF_3$ | Cl | F | $NO_2$ | $OCH_3$ | 123.0–124.0° C. |
| 73 | $CF_3$ | Cl | F | $NH_2$ | $OCH_3$ | 120.0–120.5° C. |
| 74 | $CF_3$ | Cl | F | Cl | $OCH_3$ | 100.0° C. |
| 75 | $CF_3$ | Cl | F | F | H | 43.0–44.0° C. |
| 76 | $CF_3$ | Cl | F | Cl | $OCH_2C \equiv CH$ | 116.5–117.0° C. |
| 77 | $CF_3$ | Cl | F | F | $NO_2$ | 57.0–58.5° C. |
| 78 | $CF_3$ | Cl | F | $OCH_3$ | $NO_2$ | 108.0° C. |

TABLE 4-continued
PHYSICAL DATA FOR 1-METHYL-5-ARYLPYRAZOLES

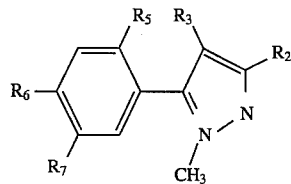

| Compound No. | $R_2$ | $R_3$ | $R_5$ | $R_6$ | $R_7$ | physical data (mp, bp, nD) |
|---|---|---|---|---|---|---|
| 79 | $CF_3$ | Cl | F | Cl | H | 73.0–74.0° C. |
| 80 | $CF_3$ | Cl | Cl | Cl | F | 71.5–72.5° C. |

TABLE 5
PHYSICAL DATA FOR 1-METHYL-3-ARYLPYRAZOLES

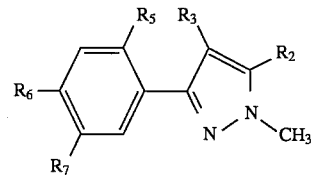

| Compound No. | $R_2$ | $R_3$ | $R_5$ | $R_6$ | $R_7$ | physical data (mp, bp, nD) |
|---|---|---|---|---|---|---|
| 81 | $CF_3$ | Cl | H | $NO_2$ | H | 93.0–95.0° C. |
| 82 | $CF_3$ | Cl | H | Cl | H | 68.2–69.2° C. |
| 83 | $CF_2Cl$ | Cl | H | Cl | H | 37.0–38.4° C. |
| 84 | $CF_3$ | Cl | Cl | Cl | F | 64.0° C. |
| 85 | $CF_3$ | Cl | Cl | Cl | H | 78.5–79.5° C. |
| 86 | $CF_3$ | Cl | Cl | Cl | $NO_2$ | 118.0–120.0° C. |
| 87 | $CF_3$ | Cl | Cl | Cl | $N(SO_2CH_3)_2$ | 137.0° C. |
| 88 | $CF_3$ | Cl | Cl | Cl | $NHCOCF_3$ | 125.0° C. |
| 89 | $CF_3$ | Cl | Cl | Cl | $SO_2Cl$ | 127.0–128.0° C. |
| 90 | $CF_3$ | Cl | Cl | Cl | $N(SO_2CH_2CH_3)_2$ | 185.0° C. |
| 91 | $CF_3$ | Cl | Cl | Cl | $NHSO_2CH_3$ | 160.0° C. |
| 92 | $CF_3$ | Cl | Cl | Cl | $NHSO_2CH_2CH_3$ | 125.0° C. |
| 93 | $CF_3$ | Cl | Cl | Cl | SH | 100.0° C. |
| 94 | $CF_3$ | Cl | F | Br | $OCH_3$ | 76.0–77.0° C. |
| 95 | $CF_3$ | Cl | F | Br | OH | 83.0–84.0° C. |
| 96 | $CF_3$ | Cl | F | Br | $OCH_2C\equiv CH$ | 112.0–113.5° C. |
| 97 | $CF_3$ | Cl | F | Br | $OCH(CH_3)CO_2Et$ | nD, 1.5217 (25° C.) |
| 98 | $CF_3$ | Cl | F | Cl | 2-(4,5-DIHYDROOXAZOLYL) | 110.0° C. |
| 99 | $CF_3$ | Cl | F | Cl | 4-MORPHOLINYL | 98.0–99.0° C. |
| 100 | $CF_3$ | Cl | F | Cl | 2-(1,3-DIOXOLANYL) | nD 1.5348 (25° C.) |
| 101 | $CF_3$ | Cl | F | Cl | 2-(1,3-DITHIOLANYL) | clear colorless oil |
| 102 | $CF_3$ | Cl | F | Cl | 2-(1,3-OXATHIOLANYL) | nD 1.5614 (25° C.) |
| 103 | $CF_3$ | Cl | F | Cl | $C(CH_3)_2C\equiv N$ | nD, 1.5274 (25° C.) |
| 104 | $CF_3$ | Cl | F | Cl | $C(CH_3)=NOCH_2CO_2Et$ | nD, 1.5203 (25° C.) |
| 105 | $CF_3$ | Cl | F | Cl | $C(CH_3)=NOCH_2CONH_2$ | 96.0° C. |
| 106 | $CF_3$ | Cl | F | Cl | $CH(CH_3)C\equiv N$ | nD, 1.5280 (25° C.) |
| 107 | $CF_3$ | Cl | F | Cl | $CH(CH_3)OH$ | 85.0–87.0° C. |
| 108 | $CF_3$ | Cl | F | Cl | $CH_2Br$ | 112.0–114.0° C. |
| 109 | $CF_3$ | Cl | F | Cl | $CH_2Cl$ | 100.0–102.0° C. |
| 110 | $CF_3$ | Cl | F | Cl | $CH_3CO_2CH_3$ | 64.0–65.0° C. |
| 111 | $CF_3$ | Cl | F | Cl | $CH_2CO_2H$ | 139.0–141.0° C. |
| 112 | $CF_3$ | Cl | F | Cl | $CH_2CONH_2$ | 185.0–189.0° C. |
| 113 | $CF_3$ | Cl | F | Cl | $CH_2CONHCH_2CH_2Cl$ | 187.0° C. |
| 114 | $CF_3$ | Cl | F | Cl | $CH_2CONHCH_3$ | 212.0° C. |
| 115 | $CF_3$ | Cl | F | Cl | $CH_2C\equiv N$ | 89.0–91.0° C. |
| 116 | $CF_3$ | Cl | F | Cl | $CH_2OCH_2CH_2F$ | 57.0° C. |
| 117 | $CF_3$ | Cl | F | Cl | $CH_2OCH_2CH_2OCH_3$ | nD, 1.5155 (25° C.) |
| 118 | $CF_3$ | Cl | F | Cl | $CH_2OCH_2CH_3$ | 34.0–37.0° C. |
| 119 | $CF_3$ | Cl | F | Cl | $CH_2OCH_2CO_2CH(CH_3)_2$ | 55.0° C. |
| 120 | $CF_3$ | Cl | F | Cl | $CH_2OCH_2C\equiv CH$ | 44.0° C. |
| 121 | $CF_3$ | Cl | F | Cl | $CH_2OCOCH_3$ | 90.0° C. |

TABLE 5-continued

PHYSICAL DATA FOR 1-METHYL-3-ARYLPYRAZOLES

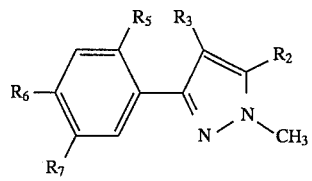

| Compound No. | R₂ | R₃ | R₅ | R₆ | R₇ | physical data (mp, bp, nD) |
|---|---|---|---|---|---|---|
| 122 | CF₃ | Cl | F | Cl | CH₂OH | 103.0–104.0° C. |
| 123 | CF₃ | Cl | F | Cl | CH₂SCH₂CO₂Et | 63.0° C. |
| 124 | CF₃ | Cl | F | Cl | CH₃ | 72.0–74.0° C. |
| 125 | CF₃ | Br | F | Cl | CH₃ | 93.0–95.0° C. |
| 126 | CF₂H | Cl | F | Cl | CH₃ | 115.0° C. |
| 127 | CF₃ | Cl | F | Cl | CH=C(CH₃)CO₂Et | 54.0° C. |
| 128 | CF₃ | Cl | F | Cl | CH=CHCO₂CH₃ | 117.0° C. |
| 129 | CF₃ | Cl | F | Cl | CH=NOCH₂CO₂Et | nD, 1.5330 (25° C.) |
| 130 | CF₃ | Cl | F | Cl | CH=NOCH₂CO₂H | 170.0° C. |
| 131 | CF₃ | Cl | F | Cl | CH=NOCH₂CONH₂ | 169.0° C. |
| 132 | CF₃ | Cl | F | Cl | CHBr₂ | 89.0–92.0° C. |
| 133 | CF₃ | Cl | F | Cl | CHO | 70.0–72.0° C. |
| 134 | CF₃ | Cl | F | Cl | CO₂-cyclohexyl | nD, 1.5287 (25° C.) |
| 135 | CF₃ | Cl | F | Cl | CO₂CH(CH₃)₂ | 69.0° C. |
| 136 | CF₃ | Cl | F | Cl | CO₂CH(CH₃)CH₂CH₃ | nD, 1.5150 (25° C.) |
| 137 | CF₃ | Cl | F | Cl | CO₂CH(CH₃)CO₂CH₃ | nD, 1.5190 (25° C.) |
| 138 | CF₃ | Cl | F | Cl | CO₂CH(CH₃)CO₂Et | nD, 1.5119 (25° C.) |
| 139 | CF₃ | Cl | F | Cl | CO₂CH₂CH(CH₃)₂ | nD, 1.5158 (25° C.) |
| 140 | CF₃ | Cl | F | Cl | CO₂CH₂CH(CH₃)CH₂CH₃ | nD, 1.5145 (25° C.) |
| 141 | CF₃ | Cl | F | Cl | CO₂CH₂CH₂CH(CH₃)₂ | nD, 1.5132 (25° C.) |
| 142 | CF₃ | Cl | F | Cl | CO₂CH₂CH₂OCH₃ | 64.0° C. |
| 143 | CF₃ | Cl | F | Cl | CO₂CH₂CO₂Et | 83.0° C. |
| 144 | CF₃ | Cl | F | Cl | CO₂CH₂C≡CH | 92.0° C. |
| 145 | CF₃ | Cl | F | Cl | CO₂CH₂OCH₃ | 77.0° C. |
| 146 | CF₃ | Cl | F | Cl | CO₂CH₃ | 78.0° C. |
| 147 | CF₃ | Cl | F | Cl | CO₂CHFCO₂Et | nD, 1.5112 (25° C.) |
| 148 | CF₃ | Cl | F | Cl | CO₂Et | 88.0° C. |
| 149 | CF₃ | Cl | F | Cl | CO₂H | 179.0–180.0° C. |
| 150 | CF₃ | Cl | F | Cl | CO₂n-butyl | clear oil |
| 151 | CF₃ | Cl | F | Cl | CO₂t-butyl | nD, 1.5130 (25° C.) |
| 152 | CF₃ | Cl | F | Cl | COCH₃ | 134.0–135.0° C. |
| 153 | CF₃ | Cl | F | Cl | CON(CH₃)₂ | clear oil |
| 154 | CF₃ | Cl | F | Cl | CONHC(CH₃)₂CH₂OH | 115.0° C. |
| 155 | CF₃ | Cl | F | Cl | CONHCH₂CH₂Cl | 129.0° C. |
| 156 | CF₃ | Cl | F | Cl | CONHCH₂OH | 143.0° C. |
| 157 | CF₃ | Cl | F | Cl | CONHCH₃ | 172.0° C. |
| 158 | CF₃ | Cl | F | Cl | CONHN(CH₃)₂ | 172.0° C. |
| 159 | CF₃ | Cl | F | Cl | CONHOCH₂CO₂CH₃ | 95.0° C. |
| 160 | CF₃ | Cl | F | Cl | COSCH(CH₃)₂ | nD, 1.5475 (25° C.) |
| 161 | CF₃ | Cl | F | Cl | COSCH(CH₃)CO₂Et | nD, 1.4723 (25° C.) |
| 162 | CF₃ | Cl | F | Cl | F | 45.5–46.5° C. |
| 163 | CF₃ | Cl | F | Cl | H | 34.0–35.0° C. |
| 164 | CCl₃ | Cl | F | Cl | H | 62.0–64.0° C. |
| 165 | CF₂H | Cl | F | Cl | H | 61.0° C. |
| 166 | CF₃ | Cl | F | Cl | N(CH₃)CH₂CH₂CH₃ | nD, 1.5030 (25° C.) |
| 167 | CF₃ | Cl | F | Cl | N(COCF₃)CH₂CH=CH₂ | 75.0° C. |
| 168 | CF₃ | Cl | F | Cl | N(COCF₃)CH₂CO₂Et | 76.0–79.0° C. |
| 169 | CF₃ | Cl | F | Cl | N(COCF₃)CH₂C≡CH | nD, 1.5061 (25° C.) |
| 170 | CF₃ | Cl | F | Cl | N(COCF₃)CH₃ | nD, 1.5004 (25° C.) |
| 171 | CF₃ | Cl | F | Cl | N(COCH₃)CH(CH₃)₂COCH₃ | 140.0° C. |
| 172 | CF₃ | Cl | F | Cl | N(SO₂CH₂CH₂CH₃)₂ | 138.0° C. |
| 173 | CF₃ | Cl | F | Cl | N(SO₂CH₂CH₃)₂ | 135.0° C. |
| 174 | CF₃ | Cl | F | Cl | N(SO₂CH₃)₂ | 205.0° C. |
| 175 | CF₃ | Cl | F | Cl | N(SO₂N(CH₃)₂)₂ | 149.0–153.0° C. |
| 176 | CF₃ | Cl | F | Cl | NEt₂ | nD, 1.5262 (25° C.) |
| 177 | CF₃ | Cl | F | Cl | NH₂ | 96.0–98.0° C. |
| 178 | CF₂H | Cl | F | Cl | NH₂ | 110.0–111.5° C. |
| 179 | CF₃ | Cl | F | Cl | NHCH(CH₃)₂ | nD, 1.5361 (25° C.) |
| 180 | CF₃ | Cl | F | Cl | NHCH(CH₃)CO₂Et | 55.0–57.0° C. |
| 181 | CF₃ | Cl | F | Cl | NHCH(CH₃)CO₂H | 167.0–169.0° C. |
| 182 | CF₃ | Cl | F | Cl | NHCH(CH₃)CONHCH₃ | 134.0–135.0° C. |
| 183 | CF₃ | Cl | F | Cl | NHCH₂CH=CH₂ | nD, 1.5483 (25° C.) |
| 184 | CF₃ | Cl | F | Cl | NHCH₂CO₂Et | 114.0–116.0° C. |

TABLE 5-continued

PHYSICAL DATA FOR 1-METHYL-3-ARYLPYRAZOLES

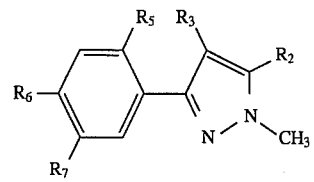

| Compound No. | R₂ | R₃ | R₅ | R₆ | R₇ | physical data (mp, bp, nD) |
|---|---|---|---|---|---|---|
| 185 | CF₃ | Cl | F | Cl | NHCH₂CO₂H | 176.0–182.0° C. |
| 186 | CF₃ | Cl | F | Cl | NHCH₂C≡CH | 73.0° C. |
| 187 | CF₃ | Cl | F | Cl | NHCH₃ | nD, 1.5509 (25° C.) |
| 188 | CF₃ | Cl | F | Cl | NHCO₂Et | 74.0–76.0° C. |
| 189 | CF₃ | Cl | F | Cl | NHCOCF₃ | 137.0–138.0° C. |
| 190 | CF₃ | Cl | F | Cl | NHCOCH₂CO₂CH₃ | 155.0° C. |
| 191 | CF₃ | Cl | F | Cl | NHCOCH₂OCH₃ | 163.0–165.0° C. |
| 192 | CF₃ | Cl | F | Cl | NHPO(OEt)₂ | 84.0–87.0° C. |
| 193 | CF₃ | Cl | F | Cl | NHSO₂CF₃ | 300.0° C. |
| 194 | CF₃ | Cl | F | Cl | NHSO₂CH₂CH₂CH₃ | 81.0° C. |
| 195 | CF₃ | Cl | F | Cl | NHSO₂CH₂CH₃ | 112.0° C. |
| 196 | CF₃ | Cl | F | Cl | NHSO₂CH₃ | 108.0° C. |
| 197 | CF₃ | Cl | F | Cl | NO₂ | 102.0–104.0° C. |
| 198 | CF₂H | Cl | F | Cl | NO₂ | 91–92.5° C. |
| 199 | CF₃ | Cl | F | Cl | O(CH₂)₅CO₂Et | nD, 1.5077 (25° C.) |
| 200 | CF₃ | Cl | F | Cl | O(CH₂)₅CO₂H | nD, 1.5174 (25° C.) |
| 201 | CF₃ | Cl | F | Cl | O(CH₂)₅CONHCH₂CH₂OH | 62.0–64.0° C. |
| 202 | CF₃ | Cl | F | Cl | O(CH₂)₅CONHCH₃ | 118.0–120.0° C. |
| 203 | CF₃ | Cl | F | Cl | O-(2-chloro-4-trifluoromethyl)phenyl | nD, 1.5356 (25° C.) |
| 204 | CF₃ | Cl | F | Cl | O-(2-nitro-4-trifluoromethylphenyl) | 119.0° C. |
| 205 | CF₃ | Cl | F | Cl | O-(4-trifluoromethyl)phenyl | nD, 1.5275 (25° C.) |
| 206 | CF₃ | Cl | F | Cl | O-(p-nitrophenyl) | nD, 1.5796 (25° C.) |
| 207 | CF₃ | Cl | F | Cl | O-n-dodecyl | nD, 1.4985 (25° C.) |
| 208 | CF₃ | Cl | F | Cl | O-n-hexyl | nD, 1.5104 (25° C.) |
| 209 | CF₂H | Cl | F | Cl | OC(CH₃)₂CH₂Cl | nD, 1.5210 (25° C.) |
| 210 | CF₃ | Cl | F | Cl | OC(CH₃)₃ | nD, 1.5128 (25° C.) |
| 211 | CF₃ | Cl | F | Cl | OCF₂H | 45.0° C. |
| 212 | CF₃ | Cl | F | Cl | OCH(CH₂CH₃)CO₂Et | nD, 1.4309 (25° C.) |
| 213 | CF₃ | Cl | F | Cl | OCH(CH₂CH₃)CO₂H | 139.0–140.0° C. |
| 214 | CF₃ | Cl | F | Cl | OCH(CH₂CH₃)CONHCH₃ | 152.0° C. |
| 215 | CF₃ | Cl | F | Cl | OCH(CH₃)(2-(4,5-dihydooxazolyl)) | nD, 1.5336 (25° C.) |
| 216 | CF₃ | Cl | F | Cl | OCH(CH₃)₂ | nD, 1.5169 (25° C.) |
| 217 | CF₃ | Cl | F | Cl | OCH(CH₃)C≡CH | 59.5–61.5° C. |
| 218 | CF₃ | Cl | F | Cl | OCH(CH₃)CH₂OCH₃ | clear oil |
| 219 | CF₃ | Cl | F | Cl | OCH(CH₃)CO₂(CH₂)₂Cl | nD, 1.5168 (25° C.) |
| 220 | CF₃ | Cl | F | Cl | OCH(CH₃)CO₂(CH₂)₃CH₃ | nD, 1.5005 (25° C.) |
| 221 | CF₃ | Cl | F | Cl | OCH(CH₃)CO₂(CH₂)₄Cl | nD, 1.5155 (25° C.) |
| 222 | CF₃ | Cl | F | Cl | OCH(CH₃)CO₂⁻Na⁺ | 51.0–60.0° C. |
| 223 | CF₃ | Cl | F | Cl | OCH(CH₃)CO₂CH(CH₃)₂ | clear, colorless oil |
| 224 | CF₃ | Cl | F | Cl | OCH(CH₃)CO₂CH(CH₃)CH₂CH₃ | nD, 1.5031 (25° C.) |
| 225 | CF₃ | Cl | F | Cl | OCH(CH₃)CO₂CH₂CH(CH₃)₂ | nD, 1.5037 (25° C.) |
| 226 | CF₃ | Cl | F | Cl | OCH(CH₃)CO₂CH₂CO₂Et | nD, 1.5061 (25° C.) |
| 227 | CF₃ | Cl | F | Cl | OCH(CH₃)CO₂CH₂OCH₃ | nD, 1.5120 (25° C.) |
| 228 | CF₃ | Cl | F | Cl | OCH(CH₃)CO₂CH₃ | nD, 1.5175 (25° C.) |
| 229 | CF₃ | Cl | F | Cl | OCH(CH₃)CO₂Et | nD, 1.5106 (25° C.) |
| 230 | CF₃ | Cl | F | Cl | OCH(CH₃)CO₂H | 150.0–151.0° C. |
| 231 | CF₃ | Cl | F | Cl | OCH(CH₃)CO₂t-butyl | nD, 1.4999 (25° C.) |
| 232 | CF₃ | Cl | F | Cl | OCH(CH₃)CON(CH₃)₂ | lt. yellow oil |
| 233 | CF₃ | Cl | F | Cl | OCH(CH₃)CONH₂ | 152.0° C. |
| 234 | CF₃ | Cl | F | Cl | OCH(CH₃)CONHCH₂CH₂Cl | 104.0° C. |
| 235 | CF₃ | C | F | Cl | OCH(CH₃)CONHCH₂CH₂OH | 131.0° C. |
| 236 | CF₃ | Cl | F | Cl | OCH(CH₃)CONHCH₂CO₂CH₃ | 111.0–112.0° C. |
| 237 | CF₃ | Cl | F | Cl | OCH(CH₃)CONHCH₃ | 134.5–135.5° C. |
| 238 | CF₃ | Cl | F | Cl | OCH(CH₃)CONHSO₂CH₃ | 159.0° C. |
| 239 | CF₃ | Cl | F | Cl | OCH(CH₃)COOCH₂CH₂OCH₂CH₂OMe | nD, 1.5047 (25° C.) |
| 240 | CF₃ | Cl | F | Cl | OCH(CH₃)C≡N | nD, 1.5223 (25° C.) |
| 241 | CF₃ | Cl | F | Cl | OCH(Et)CO₂CH(CH₃)₂ | nD, 1.5026 (25° C.) |
| 242 | CF₃ | Cl | F | Cl | OCH(Et)CO₂CH₃ | nD, 1.5127 (25° C.) |
| 243 | CF₃ | Cl | F | Cl | OCH(Et)CO₂n-butyl | nD, 1.4983 (25° C.) |
| 244 | CF₃ | Cl | F | Cl | OCH(Et)CO₂t-butyl | 63.0–65.0° C. |
| 245 | CF₃ | Cl | F | Cl | OCH(Et)CONH₂ | 153.0° C. |
| 246 | CF₃ | Cl | F | Cl | OCH(Et)C≡N | nD, 1.5167 (25° C.) |

TABLE 5-continued

PHYSICAL DATA FOR 1-METHYL-3-ARYLPYRAZOLES

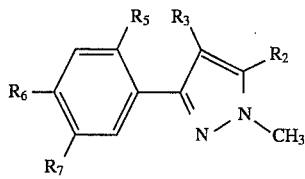

| Compound No. | R$_2$ | R$_3$ | R$_5$ | R$_6$ | R$_7$ | physical data (mp, bp, nD) |
|---|---|---|---|---|---|---|
| 247 | CF$_3$ | Cl | F | Cl | OCH(OCH$_3$)CO$_2$CH$_3$ | nD, 1.5174 (25° C.) |
| 248 | CF$_3$ | Cl | F | Cl | OCH(OCH$_3$)CO$_2$H | lt. yellow oil |
| 249 | CF$_3$ | Cl | F | Cl | OCH(OCH$_3$)CONHCH$_3$ | 96.0° C. |
| 250 | CF$_3$ | Cl | F | Cl | OCH$_2$(1,3-DIOXOLAN-2-YL) | 102.5–104.5° C. |
| 251 | CF$_3$ | Cl | F | Cl | OCH$_2$(2-pyridyl) | 122–123° C. (dec) |
| 252 | CF$_3$ | Cl | F | Cl | OCH$_2$(5-(2-chloro)thiophene) | 78–80° C. |
| 253 | CF$_3$ | Cl | F | Cl | OCH$_2$(OXIRANYL) | 85.5–86.5° C. |
| 254 | CF$_3$ | Cl | F | Cl | OCH$_2$(TETRAHYDRO-2H-PYRAN-2-YL) | 88.5–90.0° C. |
| 255 | CF$_3$ | Cl | F | Cl | OCH$_2$C(CH$_3$)$_2$CO$_2$CH$_3$ | nD, 1.5087 (25° C.) |
| 256 | CF$_3$ | Cl | F | Cl | OCH$_2$C(CH$_3$)$_2$CONHCH$_3$ | viscous oil |
| 257 | CF$_3$ | Cl | F | Cl | OCH$_2$C(Et)=NOCH$_2$CO$_2$Et | nD, 1.5147 (25° C.) |
| 258 | CF$_3$ | Cl | F | Cl | OCH$_2$C(Et)=NOCH$_2$CO$_2$H | 128.0° C. |
| 259 | CF$_3$ | Cl | F | Cl | OCH$_2$C(Et)=NOCH$_2$CONH$_2$ | 173.0° C. |
| 260 | CF$_3$ | Cl | F | Cl | OCH$_2$C(Et)=NOCH$_3$ | nD, 1.5216 (25° C.) |
| 261 | CF$_3$ | Cl | F | Cl | OCH$_2$C≡CH | 89.5–91.0° C. |
| 262 | CF$_3$ | Br | F | Cl | OCH$_2$C≡CH | 107.0° C. |
| 263 | CF$_3$ | Cl | F | Cl | OCH$_2$CF$_3$ | 68.0° C. |
| 264 | CF$_3$ | Cl | F | Cl | OCH$_2$CH(OCH$_3$)$_2$ | 62.0° C. |
| 265 | CF$_3$ | Cl | F | Cl | OCH$_2$CH$_2$(1,3-DIOXAN-2-YL) | 74.0–75.0° C. |
| 266 | CF$_3$ | Cl | F | Cl | OCH$_2$CH$_2$Br | nD, 1.5470 (25° C.) |
| 267 | CF$_3$ | Cl | F | Cl | OCH$_2$CH$_2$CH$_2$CH$_3$ | nD, 1.5153 (25° C.) |
| 268 | CF$_3$ | Cl | F | Cl | OCH$_2$CH$_2$CH$_2$OCH$_3$ | nD, 1.5175 (25° C.) |
| 269 | CF$_3$ | Cl | F | Cl | OCH$_2$CH$_2$F | 103.0° C. |
| 270 | CF$_3$ | Cl | F | Cl | OCH$_2$CH$_2$OCH$_3$ | 93.0–94.0° C. |
| 271 | CF$_3$ | Cl | F | Cl | OCH$_2$CH$_2$SCH(CH$_3$)CO$_2$Et | nD, 1.5275 (25° C.) |
| 272 | CF$_3$ | Cl | F | Cl | OCH$_2$CH$_2$SCH$_2$CO$_2$Et | nD, 1.5321 (25° C.) |
| 273 | CF$_3$ | Cl | F | Cl | OCH$_2$CH$_2$SCH$_3$ | nD, 1.5464 (25° C.) |
| 274 | CF$_3$ | Cl | F | Cl | OCH$_2$CH$_2$SO$_2$CH$_3$ | clear oil |
| 275 | CF$_3$ | Cl | F | Cl | OCH$_2$CH$_2$SOCH$_3$ | 87.0° C. |
| 276 | CF$_3$ | Cl | F | Cl | OCH$_2$CH$_3$ | 80.0° C. |
| 277 | CF$_3$ | Br | F | Cl | OCH$_2$CH=CH$_2$ | 52.5° C. |
| 278 | CF$_3$ | Cl | F | Cl | OCH$_2$CH=CH$_2$ | 76.0° C. |
| 279 | CF$_3$ | Cl | F | Cl | OCH$_2$CO$_2^-$(CH$_3$)$_2$CHNH$_3$+ | 123.0–125.0° C. |
| 280 | CF$_3$ | Cl | F | Cl | OCH$_2$CO$_2^-$Na$^+$ | 250.0° C. |
| 281 | CF$_3$ | Cl | F | Cl | OCH$_2$CO$_2$-cyclohexyl | 150.0° C. |
| 282 | CF$_3$ | Cl | F | Cl | OCH$_2$CO$_2$CH(CH$_3$)$_2$ | 134.0–135.0° C. |
| 283 | CF$_2$H | Cl | F | Cl | OCH$_2$CO$_2$CH(CH$_3$)$_2$ | 129.0–130.0° C. |
| 284 | C$_2$F$_5$ | H | F | Cl | OCH$_2$CO$_2$CH(CH$_3$)$_2$ | 91–92° C. |
| 285 | CF$_2$Cl | Cl | F | Cl | OCH$_2$CO$_2$CH(CH$_3$)$_2$ | 98° C. |
| 286 | CF$_3$ | Cl | F | Cl | OCH$_2$CO$_2$CH(CH$_3$)CH$_2$CH$_3$ | 101.0–103.0° C. |
| 287 | CF$_3$ | Cl | F | Cl | OCH$_2$CO$_2$CH$_2$CH(CH$_3$)CH$_2$CH$_3$ | 96.0° C. |
| 288 | CF$_3$ | Cl | F | Cl | OCH$_2$CO$_2$CH$_2$CH$_2$CH(CH$_3$)$_2$ | 128.0° C. |
| 289 | CF$_3$ | Cl | F | Cl | OCH$_2$CO$_2$CH$_3$ | 108.0–110.0° C. |
| 290 | CF$_3$ | Cl | F | Cl | OCH$_2$CO$_2$Et | 130.0–131.0° C. |
| 291 | CF$_3$ | Cl | F | Cl | OCH$_2$CO$_2$H | 174.0° C. |
| 292 | CF$_3$ | Cl | F | Cl | OCH$_2$CO$_2$n-butyl | 96.0–98.0° C. |
| 293 | CF$_3$ | Cl | F | Cl | OCH$_2$CO$_2$n-pentyl | 91.0–93.0° C. |
| 294 | CF$_3$ | Cl | F | Cl | OCH$_2$CO$_2$t-butyl | 127.0° C. |
| 295 | CF$_3$ | Cl | F | Cl | OCH$_2$COCH$_2$CH$_3$ | 93.0° C. |
| 296 | CF$_3$ | Cl | F | Cl | OCH$_2$CONH$_2$ | 191.0° C. |
| 297 | CF$_3$ | Cl | F | Cl | OCH$_2$CONHCH(CH$_3$)$_2$ | 130.0° C. |
| 298 | CF$_3$ | Cl | F | Cl | OCH$_2$CONHCH$_3$ | 144.0–145.0° C. |
| 299 | CF$_3$ | Cl | F | Cl | OCH$_2$CONHN(CH$_3$)$_2$ | 146.0–148.0° C. |
| 300 | CF$_3$ | Cl | F | Cl | OCH$_2$COSCH(CH$_3$)$_2$ | 96.0–97.0° C. |
| 301 | CF$_3$ | H | F | Cl | OCH$_2$C≡CH | 113.0° C. |
| 302 | CF$_2$H | Cl | F | Cl | OCH$_2$C≡CH | 68.0–69.0° C. |
| 303 | CF$_2$Cl | Cl | F | Cl | OCH$_2$C≡CH | nD, 1.5544 (24° C.) |
| 304 | CF$_3$ | Cl | F | Cl | OCH$_2$C≡N | 98.0° C. |
| 305 | CF$_3$ | Cl | F | Cl | OCH$_2$OCH$_2$CH$_2$F | nD, 1.5150 (25° C.) |
| 306 | CF$_3$ | Cl | F | Cl | OCH$_2$OCH$_2$CH$_2$OCH$_3$ | nD, 1.5134 (25° C.) |

TABLE 5-continued

PHYSICAL DATA FOR 1-METHYL-3-ARYLPYRAZOLES

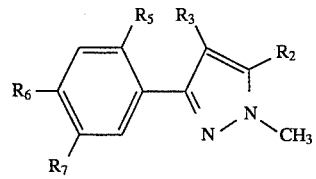

| Compound No. | $R_2$ | $R_3$ | $R_5$ | $R_6$ | $R_7$ | physical data (mp, bp, nD) |
|---|---|---|---|---|---|---|
| 307 | $CF_3$ | Cl | F | Cl | $OCH_2OCH_2C\equiv CH$ | nD, 1.5275 (25° C.) |
| 308 | $CF_3$ | Cl | F | Cl | $OCH_2OCH_3$ | 54.5–55.0° C. |
| 309 | $CF_3$ | Cl | F | Cl | $OCH_2SCH_3$ | 78.0–79.0° C. |
| 310 | $CF_3$ | Cl | F | Cl | $OCH_2SO_2CH_3$ | 137.0° C. |
| 311 | $CF_3$ | Cl | F | Cl | $OCH_2SOCH_3$ | 109.0–111.0° C. |
| 312 | $CF_3$ | Cl | F | Cl | $OCH_3$ | 70.0–71.0° C. |
| 313 | $CF_3$ | Br | F | Cl | $OCH_3$ | 85.0–86.0° C. |
| 314 | $CF_2H$ | Cl | F | Cl | $OCH_3$ | 128.0–130.0° C. |
| 315 | $CF_2Cl$ | Cl | F | Cl | $OCH_3$ | nD, 1.6399 (26° C.) |
| 316 | $CF_3$ | Cl | F | Cl | $OCH=CH_2$ | 57.0° C. |
| 317 | $CF_3$ | Cl | F | Cl | $OCHFCO_2CH(CH_3)_2$ | 96.0° C. |
| 318 | $CF_3$ | Cl | F | Cl | $OCHFCO_2Et$ | 60.0° C. |
| 319 | $CF_3$ | Cl | F | Cl | $OCHFCO_2H$ | 116.0° C. |
| 320 | $CF_3$ | Cl | F | Cl | $OCHFCOSCH(CH_3)_2$ | 65.0° C. |
| 321 | $CF_3$ | Cl | F | Cl | $OCOCH_2Cl$ | nD, 1.5299 (25° C.) |
| 322 | $CF_3$ | Cl | F | Cl | $OCOCH_2OCH_3$ | 76.0–78.0° C. |
| 323 | $CF_3$ | Cl | F | Cl | $OCOCH_3$ | 53.0–55.0° C. |
| 324 | $CF_3$ | Cl | F | Cl | $OCH_2CH_2OCH_2CH_2OCH_2CH_2OMe$ | nD, 1.5111 (25° C.) |
| 325 | $CF_3$ | Cl | F | Cl | OH | 123.0–126.0° C. |
| 326 | $CF_3$ | Br | F | Cl | OH | 83.0° C. |
| 327 | $CF_3$ | H | F | Cl | OH | 131.0° C. |
| 328 | $CF_2H$ | Cl | F | Cl | OH | 113.0–114.0° C. |
| 329 | $CF_2Cl$ | Cl | F | Cl | OH | 107–109° C. |
| 330 | $CF_3$ | Cl | F | Cl | $OSO_2CH_3$ | 64.0–65.5° C. |
| 331 | $CF_3$ | Cl | F | Cl | $OSO_2$n-propyl | nD, 1.5213 (25° C.) |
| 332 | $CF_2H$ | Cl | F | Cl | Ot-butyl | nD, 1.5276 (25° C.) |
| 333 | $CF_3$ | Cl | F | Cl | $SCF_2H$ | nD, 1.5321 (25° C.) |
| 334 | $CF_3$ | Cl | F | Cl | $SCH(CH_3)_2$ | clear oil |
| 335 | $CF_3$ | Cl | F | Cl | $SCH(CH_3)CO_2Et$ | nD, 1.5345 (25° C.) |
| 336 | $CF_3$ | Cl | F | Cl | $SCH_2CH_2OCH_3$ | 57.0° C. |
| 337 | $CF_3$ | Cl | F | Cl | $SCH_2CO_2CH(CH_3)_2$ | nD, 1.5358 (25° C.) |
| 338 | $CF_3$ | Cl | F | Cl | $SCH_2CO_2Et$ | 63.0–64.0° C. |
| 339 | $CF_3$ | Cl | F | Cl | $SCH_2CO_2H$ | 128.0° C. |
| 340 | $CF_3$ | Cl | F | Cl | $SCH_2CONH_2$ | 167.0° C. |
| 341 | $CF_3$ | Cl | F | Cl | $SCH_2C\equiv CH$ | 98.0° C. |
| 342 | $CF_3$ | Cl | F | Cl | $SCH_3$ | 89.0–90.0° C. |
| 343 | $CF_3$ | Cl | F | Cl | SH | 56.0–58.0° C. |
| 344 | $CF_3$ | Cl | F | Cl | $SO_2$(1-pyrazolyl) | 155.0° C. |
| 345 | $CF_3$ | Cl | F | Cl | $SO_2CH(CH_3)_2$ | 132° C. |
| 346 | $CF_3$ | Cl | F | Cl | $SO_2Cl$ | 116.0–117.0° C. |
| 347 | $CF_3$ | Cl | F | Cl | $SO_2N(CH_3)_2$ | 118.0° C. |
| 348 | $CF_3$ | Cl | F | Cl | $SO_2NHCH_3$ | 113.0° C. |
| 349 | $CF_3$ | Cl | F | Cl | $SOCH(CH_3)_2$ | 119.0° C. |
| 350 | $CF_3$ | Cl | F | Cl | trans-$CH=C(CH_3)CO_2H$ | 213° C. |
| 351 | $CF_3$ | Cl | F | Cl | trans-$CH=CHCO_2H$ | 209° C. |
| 352 | $CF_3$ | Cl | F | F | H | nD, 1.6284 (25° C.) |
| 353 | $CF_3$ | Cl | F | F | $NH_2$ | 82.0° C. |
| 354 | $CF_3$ | Cl | F | F | Cl | 50.0–51.0° C. |
| 355 | $CF_3$ | Cl | F | F | $NO_2$ | 90.5–91.5° C. |
| 356 | $CF_3$ | Cl | F | F | $NHCOCH_3$ | 115.0–116.0° C. |
| 357 | $CF_3$ | Cl | F | F | $N(SO_2CH_3)_2$ | 176.5° C. |
| 358 | $CF_3$ | Cl | F | F | $NHSO_2CH_3$ | 163.0–164.0° C. |
| 359 | $CF_3$ | Cl | F | F | $NHCOCH_2OCH_3$ | 152.0–154.0° C. |
| 360 | $CF_3$ | Cl | H | $OCH_3$ | $NO_2$ | 114.0–115.0° C. |
| 361 | $CF_3$ | Cl | F | H | F | nD, 1.4977 (25° C.) |
| 362 | $CF_3$ | Br | F | H | F | nD, 1.6267 (25° C.) |
| 363 | $CF_3$ | Cl | F | H | $OC(CH_3)_2CH_2Cl$ | nD, 1.5145 (25° C.) |
| 364 | $CF_2H$ | Cl | F | H | F | nD, 1.5218 (25° C.) |
| 365 | $CF_2H$ | Br | F | H | F | 61.5° C. |
| 366 | $CF_3$ | Cl | F | $NH_2$ | $OCH_3$ | 62.5–63.5° C. |
| 367 | $CF_3$ | Cl | F | $NH_2$ | $OCH_2CH_2F$ | 135.0° C. |
| 368 | $CF_3$ | Cl | F | $NH_2$ | OEt | 136.0° C. |
| 369 | $CF_3$ | Cl | F | $NH_2$ | $OCH_2C\equiv CH$ | 72.0° C. |

TABLE 5-continued

PHYSICAL DATA FOR 1-METHYL-3-ARYLPYRAZOLES

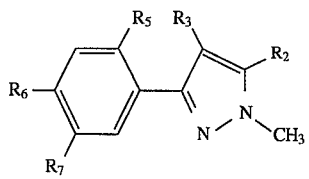

| Compound No. | $R_2$ | $R_3$ | $R_5$ | $R_6$ | $R_7$ | physical data (mp, bp, nD) |
|---|---|---|---|---|---|---|
| 370 | $CF_3$ | Cl | F | $NH_2$ | $OCH(CH_3)CCH$ | nD, 1.5450 (25° C.) |
| 371 | $CF_3$ | H | F | $NH_2$ | $OCH_3$ | 121.5–123.0° C. |
| 372 | $CF_3$ | Br | F | $NH_2$ | $OCH_3$ | 85.0–86.0° C. |
| 373 | $CF_3$ | Cl | F | $NH_2$ | $OCH_2CH_2OCH_2CH_2OCH_2CH_2OMe$ | nD, 1.5254 (25° C.) |
| 374 | $CF_3$ | Cl | F | $NH_2$ | F | 84.0–86.0° C. |
| 375 | $CF_3$ | Cl | F | $NH_2$ | $OC(CH_3)_3$ | light yellow oil |
| 376 | $CF_3$ | Cl | F | $NH_2$ | $N(CH_3)CH_2CH_2CH_3$ | nD, 1.5352 (25° C.) |
| 377 | $CF_3$ | Cl | F | $NH_2$ | $NEt_2$ | nD, 1.5321 (25° C.) |
| 378 | $CF_3$ | Cl | F | $NH_2$ | 4-MORPHOLINYL | 165.0–166.0° C. |
| 379 | $CF_3$ | Cl | F | $NH_2$ | $N(COCH_3)CH(CH_3)_2$ | 178.0° C. |
| 380 | $CF_3$ | Cl | F | $NH_2$ | $OCH_2CH_2SCH_3$ | nD, 1.5591 (25° C.) |
| 381 | $CF_2H$ | Cl | F | $NH_2$ | Ot-butyl | nD, 1.5443 (25° C.) |
| 382 | $CF_3$ | Cl | F | $NH_2$ | $OCH_2CF_3$ | 66.0° C. |
| 383 | $CF_3$ | Cl | F | $NH_2$ | $NHCH_2CH=CH_2$ | 112.0° C. |
| 384 | $CF_3$ | Cl | F | $OCH_2C\equiv CH$ | $NO_2$ | 142.0° C. |
| 385 | $CF_3$ | Cl | F | $OCH_2C\equiv CH$ | $NH_2$ | 94.0–96.0° C. |
| 386 | $CF_3$ | Cl | F | $OCH_2CO_2Et$ | $NO_2$ | 95.0–96.0° C. |
| 387 | $CF_3$ | Cl | F | $OCH_3$ | $NO_2$ | 116.0° C. |
| 388 | $CF_3$ | H | F | $NO_2$ | F | 80.0–81.0° C. |
| 389 | $CF_3$ | Cl | F | $NO_2$ | F | nD, 1.5276 (25° C.) |
| 390 | $CF_3$ | Cl | F | $NO_2$ | $OCH_3$ | 115.0–116.0° C |
| 391 | $CF_3$ | Cl | F | $NO_2$ | $OCH_2CH_2F$ | 134° C. |
| 392 | $CF_3$ | Cl | F | $NO_2$ | $OCH_2CH_3$ | 99.0° C. |
| 393 | $CF_3$ | Cl | F | $NO_2$ | $SCH_2CO_2Et$ | 79.0° C. |
| 394 | $CF_3$ | Cl | F | $NO_2$ | $OCH_2C\equiv CH$ | 105.0° C. |
| 395 | $CF_3$ | Cl | F | $NO_2$ | $OCH(CH_3)C\equiv CH$ | 107.5–108.0° C. |
| 396 | $CF_3$ | Br | F | $NO_2$ | F | 45.5° C. |
| 397 | $CF_3$ | Br | F | $NO_2$ | $OCH_3$ | 144.5–145.5° C. |
| 398 | $CF_3$ | H | F | $NO_2$ | $OCH_3$ | 140.0–141.5° C. |
| 399 | $CF_3$ | Cl | F | $NO_2$ | $OCH_2CH_2OCH_2CH_2OCH_2CH_2OMe$ | nD, 1.5188 (25° C.) |
| 400 | $CF_3$ | Cl | F | $NO_2$ | $OCH_2CO_2Et$ | 104.0° C. |
| 401 | $CF_3$ | Cl | F | $NO_2$ | $OC(CH_3)_3$ | 80.0° C. |
| 402 | $CF_3$ | Cl | F | $NO_2$ | $N(CH_3)CH_2CH_2CH_3$ | nD, 1.5534 (25° C.) |
| 403 | $CF_3$ | Cl | F | $NO_2$ | $NHCH(CH_3)_2$ | 100.0° C. |
| 404 | $CF_3$ | Cl | F | $NO_2$ | $NEt_2$ | nD, 1.5387 (25° C.) |
| 405 | $CF_3$ | Cl | F | $NO_2$ | 4-MORPHOLINYL | 136.0–137.0° C. |
| 406 | $CF_3$ | Cl | F | $NO_2$ | $N(COCH_3)CH(CH_3)_2$ | 123.0° C. |
| 407 | $CF_3$ | Cl | F | $NO_2$ | $SCH(CH_3)CO_2Et$ | nD, 1.5543 (25° C.) |
| 408 | $CF_3$ | Cl | F | $NO_2$ | OH | 86.0° C. |
| 409 | $CF_3$ | Cl | F | $NO_2$ | $NHCH_2CH_2OCH_3$ | 109.0° C. |
| 410 | $CF_3$ | Cl | F | $NO_2$ | $OCH_2COCH_2CH_3$ | 103.0° C. |
| 411 | $CF_3$ | Cl | F | $NO_2$ | $OCH(CH_3)CH_2OCH_3$ | nD, 1.5263(25° C.) |
| 412 | $CF_3$ | Cl | F | $NO_2$ | $OCH_2CH_2CH_2OCH_3$ | 67.0° C. |
| 413 | $CF_3$ | Cl | F | $NO_2$ | $N(COCF_3)CH_2CH_2CH_2OCH_3$ | 105.0° C. |
| 414 | $CF_2H$ | Cl | F | $NO_2$ | F | 80.0° C. |
| 415 | $CF_2H$ | Cl | F | $NO_2$ | $OCH_3$ | 161.0° C. |
| 416 | $CF_3$ | Cl | F | $NO_2$ | $OCH_2CH_2SCH_3$ | nD, 1.5587 (25° C.) |
| 417 | $CF_2H$ | Br | F | $NO_2$ | F | 83.0–85.0° C. |
| 418 | $CF_2H$ | Br | F | $NO_2$ | $OCH_3$ | 154.0–156.0° C. |
| 419 | $CF_2H$ | Cl | F | $NO_2$ | Ot-butyl | 71.0–73.0° C. |
| 420 | $CF_3$ | Cl | F | $NO_2$ | $OCH_2CF_3$ | 108.0–109.0° C. |
| 421 | $CF_3$ | Cl | F | $NO_2$ | $NHCH_2CH=CH_2$ | 54.0–56.0° C. |
| 422 | $CF_3$ | Cl | F | $NO_2$ | $N(COCF_3)CH_2CH=CH_2$ | 91.0° C. |
| 423 | $CF_3$ | Cl | F | $OCH_3$ | $NH_2$ | light yellow oil |
| 424 | $CF_3$ | Cl | F | $OCH_3$ | Cl | 88.0° C. |
| 425 | $CF_3$ | Cl | F | $OCH_3$ | $NHCOCH_2CO_2CH_3$ | 111.0° C. |
| 426 | $CF_3$ | Cl | F | $OCH_3$ | $NHCOCH(CH_3)_2$ | 134.0° C. |
| 427 | $CF_3$ | Cl | F | $OCH_3$ | H | 97.0° C. |
| 428 | $CF_3$ | Cl | F | $OCHFCO_2Et$ | $NO_2$ | 84.5–85.5° C. |
| 429 | $CF_3$ | Cl | F | OH | $NO_2$ | m.p. 89.0–90.0° C. |
| 430 | $CF_3$ | Cl. | F | $SCH_2CO_2Et$ | $NO_2$ | 90.0° C. |
| 431 | $CF_3$ | Cl | H | $OCH_2CO_2Et$ | $NO_2$ | 88.0° C. |

TABLE 5-continued
PHYSICAL DATA FOR 1-METHYL-3-ARYLPYRAZOLES
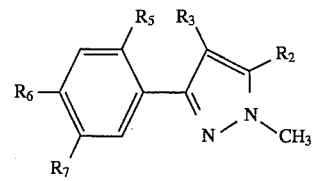
| Compound No. | $R_2$ | $R_3$ | $R_5$ | $R_6$ | $R_7$ | physical data (mp, bp, nD) |
|---|---|---|---|---|---|---|
| 432 | $CF_3$ | Cl | H | H | $OCH_3$ | b.p.$_{0.8}$ 120.0° C. |
| 433 | $CF_3$ | Cl | H | H | $CF_3$ | b.p.$_{3.0}$ 80.0–120.0° C. |
| 434 | $CF_3$ | Cl | H | F | H | 35.5–36.5° C. |
In Table 6 are listed various other compounds according to Formula I whose structures do not conveniently fit into Tables 4 and 5.

TABLE 6

| Compound # | Name | Structure | Analysis (%) | | |
|---|---|---|---|---|---|
| | | | | Calc'd | Found |
| 435 | 1H-pyrazole,-4-chloro-3-(6-fluoro-2,-3-dihydro-1,4-benzoxathiin-7-yl)-1-methyl-5-(trifluoromethyl)-<br>MP: 93.0 | 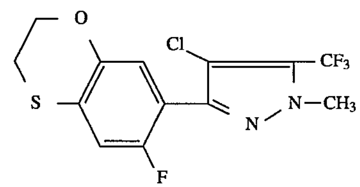 | C<br>H<br>Cl<br>F<br>N<br>S | 44.27<br>2.57<br>10.05<br>21.55<br>7.94<br>9.09 | 44.34<br>2.57<br><br><br>7.98<br> |
| 436 | 1H-pyrazole,-4-chloro-3-(6-fluoro-2,-3-dihydro-1,4-benzoxathiin-7-yl)-1-methyl-5-(trifluoromethyl),-S,-S-dioxide<br>MP: 200.0 | 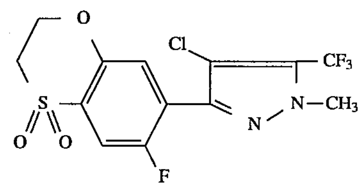 | C<br>H<br>Cl<br>F<br>N<br>S | 40.58<br>2.36<br>9.21<br>19.75<br>7.28<br>8.33 | 40.70<br>2.35<br><br><br>7.26<br> |
| 437 | 1H-pyrazole,-4-chloro-3-(6-fluoro-2,-3-dihydro-1,4-benzoxathiin-7-yl)-1-methyl-5-(trifluoromethyl),-S-oxide<br>MP: 159.0 | 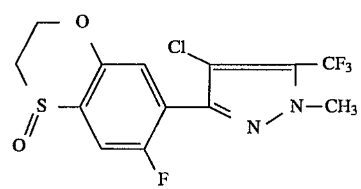 | C<br>H<br>Cl<br>F<br>N<br>S | 42.34<br>2.46<br>9.61<br>20.61<br>7.60<br>8.70 | 42.54<br>2.43<br><br><br>7.58<br> |
| 438 | 2H-1,4-benzothiazin-3(4H)-one,-6-[4-chloro-1-methyl-5-(trifluoromethyl)-1H-pyrazol-3-yl]-7-fluoro-4-(2-propynyl)-<br>MP: 174.0 | 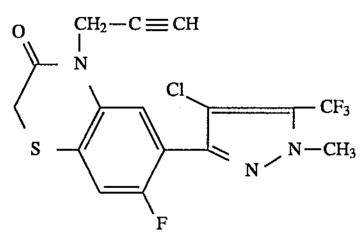 | C<br>H<br>Cl<br>F<br>N<br>S | 47.59<br>2.50<br>8.78<br>18.82<br>10.41<br>7.94 | 47.69<br>2.51<br><br><br>10.36<br> |

TABLE 6-continued

| Compound # | Name | Structure | Analysis (%) | | |
|---|---|---|---|---|---|
| | | | | Calc'd | Found |
| 439 | 2H-1,-4-benzothiazin-3(4H)-one,-6-[4-chloro-1-methyl-5-(trifluoromethyl)-1H-pyrazol-3-yl]-7-fluoro-<br>MP: 220.0 | 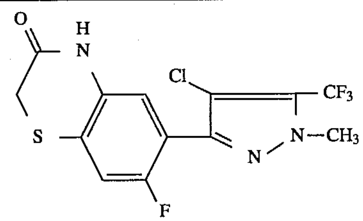 | C<br>H<br>Cl<br>F<br>N<br>S | 42.69<br>2.20<br>9.69<br>20.78<br>11.49<br>8.77 | 42.73<br>2.19<br><br><br>11.40<br> |
| 440 | 1H-pyrazole,-4-chloro-3-[3-(chloromethylene)-6-fluoro-2,-3-dihydro-5-benzofuranyl]-1-methyl-5-(trifluoromethyl)-<br>MP: 121.0 | 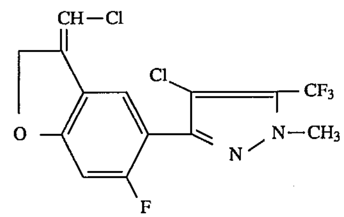 | C<br>H<br>Cl<br>F<br>N | 45.80<br>2.20<br>19.31<br>20.70<br>7.63 | 45.80<br>2.36<br><br><br>7.62 |
| 441 | 1H-imidazo[2,1-c]-[1,4]-benzoxazine,-8-[4-chloro-1-methyl-5-(trifluoromethyl)-1H-pyrazol-3-yl]-7-fluoro-2,4-dihydro-<br>MP: 118.0–120.0 | 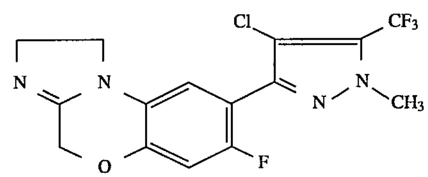 | C<br>H<br>Cl<br>F<br>N | 48.08<br>2.96<br>9.46<br>20.28<br>14.95 | 48.54<br>3.10<br><br><br> |
| 442 | 1H-pyrazole,-4-chloro-3-(7-fluoro-2,3-dihydro-1,4-benzoxathiin-6-yl)-1-methyl-5-(trifluoromethyl)-<br>MP: 125.0 | 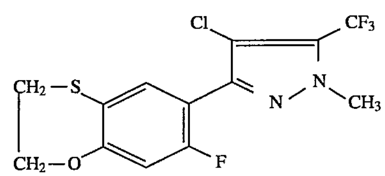 | C<br>H<br>Cl<br>F<br>N<br>S | 44.27<br>2.57<br>10.05<br>21.55<br>7.94<br>9.09 | 44.30<br>2.52<br><br><br>7.93<br> |

TABLE 6-continued

| Compound # | Name | Structure | Analysis (%) | | |
|---|---|---|---|---|---|
| | | | | Calc'd | Found |
| 443 | 4H-1,-4-benzoxazine-4-acetic acid,-6-[4-chloro-1-methyl-5-(trifluoromethyl)-1H-pyrazol-3-yl]-7-fluoro-alpha-methyl-3-oxo-,ethyl ester MP: viscous oil | 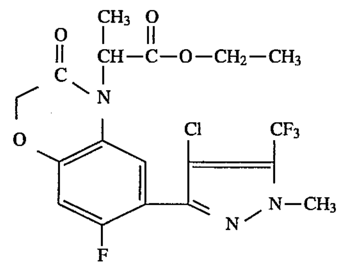 | C H Cl F N | 48.07 3.59 7.88 16.90 9.34 | 48.04 3.32 9.62 |
| 444 | 1H-isoindole-1,-3(2H)-dione,-2-[5-[4-chloro-1-methyl-5-(trifluoromethyl)-1H-pyrazol-3-yl]-2,4-difluorophenyl]-4,-5,-6,-7,-tetrahydro- MP: 76.0–78.0 | 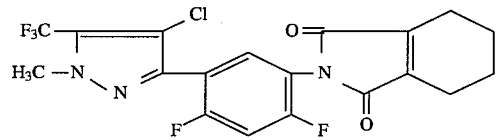 | C H Cl F N | 51.19 2.94 7.95 21.31 9.43 | 52.29 3.30 9.14 |
| 445 | 2H-1,-4-benzoxazin-3(4H)-one,-6-[4-chloro-1-methyl-5-(trifluoromethyl)-1H-pyrazol-3-yl]-4-ethyl-7-fluoro- MP: 95.0–97.0 | 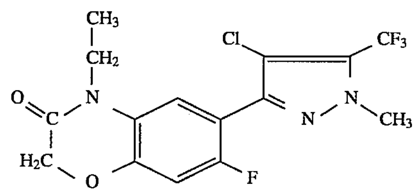 | C H Cl F N | 47.70 3.20 9.39 20.12 11.12 | 47.51 3.22 |
| 446 | 2H-1,-4-benzoxazin-3(4H)-one,-6-[4-chloro-1-methyl-5-(trifluoromethyl)-1H-pyrazol-3-yl]-7-fluoro-4-(2-propynyl)- MP: 142.0–143.0 | 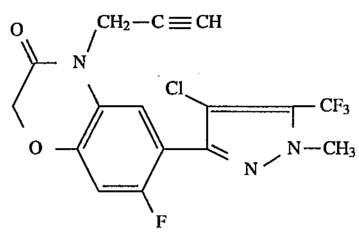 | C H Cl F N | 49.56 2.60 9.14 19.60 10.84 | 49.58 2.62 10.85 |

TABLE 6-continued

| Compound # | Name | Structure | Analysis (%) | | |
|---|---|---|---|---|---|
| | | | | Calc'd | Found |
| 447 | 4H-1,4-benzoxazine-4-acetonitrile, 6-[4-chloro-1-methyl-5-(trifluoromethyl)-1H-pyrazol-3-yl]-7-fluoro-2,3-dihydro-3-oxo- MP: 162.0–163.0 | 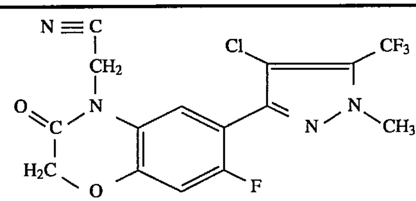 | C H Cl F N | 46.35 2.33 9.12 19.55 14.41 | 46.03 2.34 |
| 448 | 4H-1,4-benzoxazine-4-acetamide, 6-[4-chloro-1-methyl-5-(trifluoromethyl)-1H-pyrazol-3-yl]-7-fluoro-2,3-dihydro-N-methyl-3-oxo- MP: 223.0–225.0 | 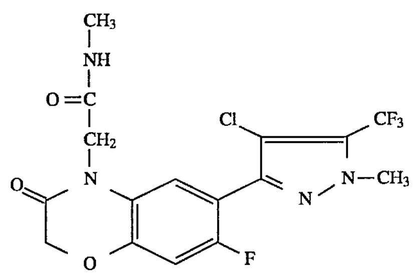 | C H Cl F N | 45.67 3.11 8.43 18.06 13.32 | 45.75 3.10 |
| 449 | 4H-1,4-benzoxazine-4-acetic acid, 6-[4-chloro-1-methyl-5-(trifluoromethyl)-1H-pyrazol-3-yl]-7-fluoro-2,3-dihydro-3-oxo-, 1,1-dimethylethyl ester MP: 161.0–162.0 | 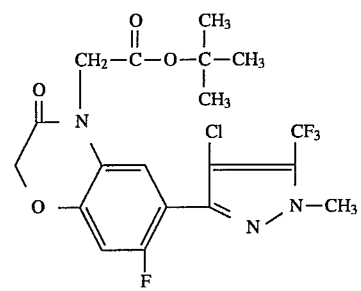 | C H Cl F N | 49.20 3.91 7.64 16.39 9.06 | 49.45 4.06 |

TABLE 6-continued

| Compound # | Name | Structure | | Analysis (%) | |
| --- | --- | --- | --- | --- | --- |
| | | | | Calc'd | Found |
| 450 | 4H-1,4-benzoxazine-4-acetic acid,-6-[4-chloro-1-methyl-5-(trifluoromethyl)-1H-pyrazol-3-yl]-7-fluoro-3-oxo-,-1-methylethyl ester<br>MP: 176.0–177.0 | 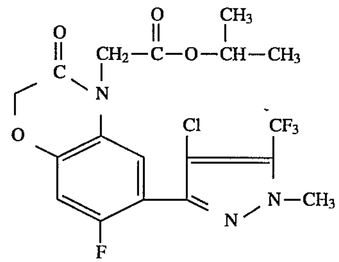 | C<br>H<br>Cl<br>F<br>N | 48.07<br>3.59<br>7.88<br>16.90<br>9.34 | 48.25<br>3.70<br><br><br>9.30 |
| 451 | 4H-1,4-benzoxazine-4-acetic acid,-6-[4-chloro-1-methyl-5-(trifluoromethyl)-1H-pyrazol-3-yl]-7-fluoro-2,3-dihydro-3-oxo,-ethyl ester<br>MP: 131.0–133.0 | 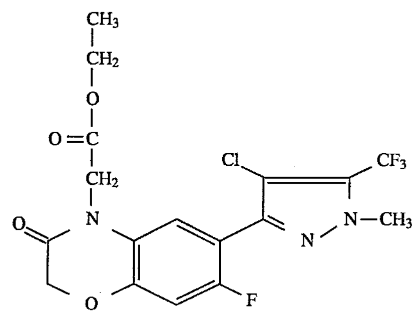 | C<br>H<br>Cl<br>F<br>N | 46.86<br>3.24<br>8.14<br>17.44<br>9.64 | 47.00<br>3.24 |
| 452 | 4H-1,4-benzoxazine-4-acetamide,-6-[4-chloro-1-methyl-5-(trifluoromethyl)-1H-pyrazol-3-yl]-7-fluoro-2,3-dihydro-3-oxo-<br>MP: 215.0–217.0 | 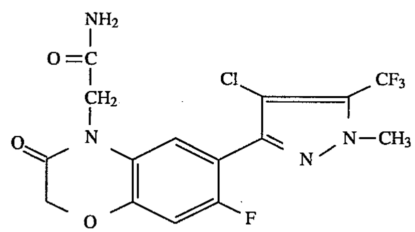 | C<br>H<br>Cl<br>F<br>N | 44.30<br>2.73<br>8.72<br>18.69<br>13.78 | 44.34<br>2.73 |

TABLE 6-continued

| Compound # | Name | Structure | Analysis (%) | | |
|---|---|---|---|---|---|
| | | | | Calc'd | Found |
| 453 | 2H-1,4-benzoxazine-4-acetic acid,-6-[4-chloro-1-methyl-5-(trifluoromethyl)-1H-pyrazol-3-yl]-7-fluoro-3,4-dihydro-3-oxo- MP: 194.0–196.0 | 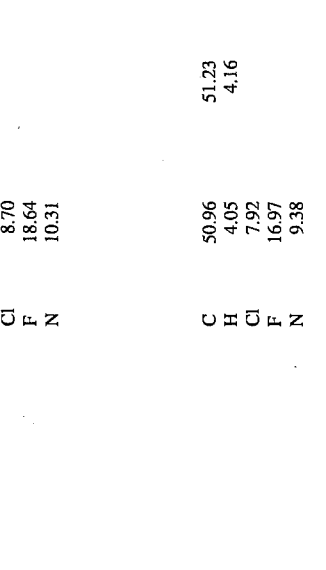 | C H Cl F N | 44.19 2.47 8.70 18.64 10.31 | 44.13 2.33 |
| 454 | 2H-1,4-benzoxazin-3(4H)-one,-6-[4-chloro-1-methyl-5-(trifluoromethyl)-1H-pyrazol-3-yl]-7-fluoro-4-[(tetrahydro-2H-pyran-2-yl)-methyl]- MP: 133.0–135.0 | 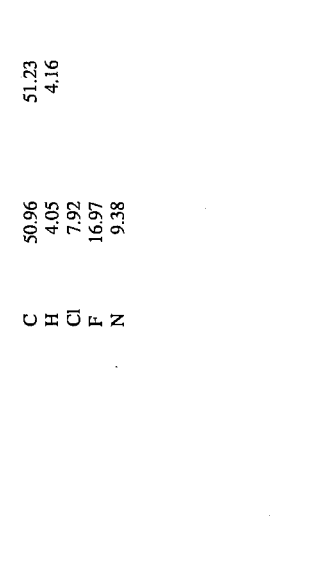 | C H Cl F N | 50.96 4.05 7.92 16.97 9.38 | 51.23 4.16 |
| 455 | 2H-1,4-benzoxazin-3(4H)-one,-6-[4-chloro-1-methyl-5-(trifluoromethyl)-1H-pyrazol-3-yl]-7-fluoro-4-(1,3-dioxolan-2-ylmethyl)- MP: 150.5–151.5 | 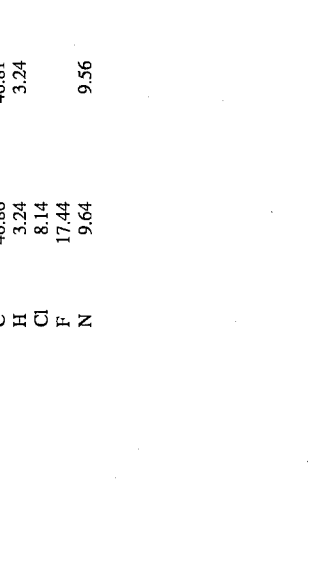 | C H Cl F N | 46.86 3.24 8.14 17.44 9.64 | 46.81 3.24 9.56 |

TABLE 6-continued

| Compound # | Name | Structure | Analysis (%) | | |
|---|---|---|---|---|---|
| | | | | Calc'd | Found |
| 456 | 2H-1,4-benzoxazin-3(4H)-one,-6-[4-chloro-1-methyl-5-(trifluoromethyl)-1H-pyrazol-3-yl]-7-fluoro-4-(2-propenyl)-MP: 84.0-86.0 | 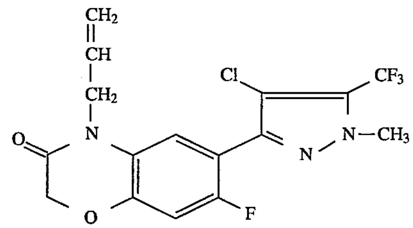 | C<br>H<br>Cl<br>F<br>N | 49.31<br>3.10<br>9.10<br>19.50<br>10.78 | 49.27<br>3.08 |
| 457 | 2H-1,4-benzoxazin-3(4H)-one,-6-[4-chloro-1-methyl-5-(trifluoromethyl)-1H-pyrazol-3-yl]-4-[2-(1,3-dioxan-2-yl)-ethyl]-7-fluoro-MP: 125.5-127.5 | 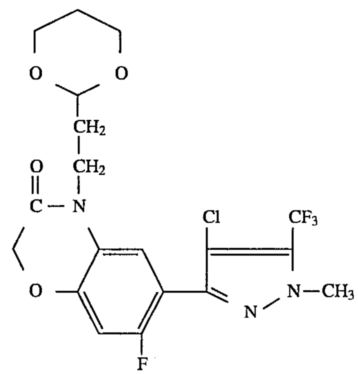 | C<br>H<br>Cl<br>F<br>N | 49.20<br>3.91<br>7.64<br>16.39<br>9.06 | 49.44<br>3.97<br><br><br>8.80 |
| 458 | 2H-1,4-benzoxazin-3(4H)-one,-6-[4-chloro-1-methyl-5-(trifluoromethyl)-1H-pyrazol-3-yl]-7-fluoro-4-(2-methoxyethyl)-MP: 91.5-92.5 | 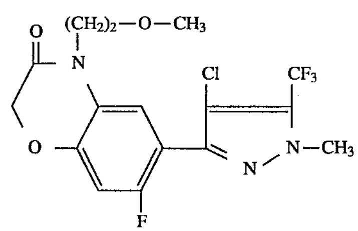 | C<br>H<br>Cl<br>F<br>N | 47.13<br>3.46<br>8.69<br>18.64<br>10.31 | 47.27<br>3.51 |

TABLE 6-continued

| Compound # | Name | Structure | Analysis (%) | | |
|---|---|---|---|---|---|
| | | | | Calc'd | Found |
| 459 | 2H-1,4-benzoxazin-3(4H)-one,-6-[4-chloro-1-methyl-5-(trifluoromethyl)-1H-pyrazol-3-yl]-7-fluoro-4-(2-pyridinylmethyl)-<br>MP: 137.0–139.0 | 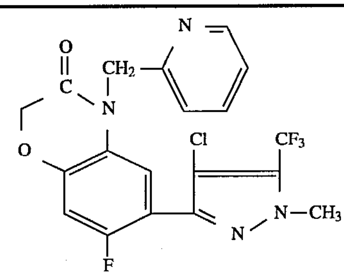 | C<br>H<br>Cl<br>F<br>N | 51.77<br>2.97<br>8.04<br>17.24<br>12.71 | 51.50<br>2.99<br><br><br>12.57 |
| 460 | 2H-1,4-benzoxazin-3(4H)-one,-6-[4-chloro-1-methyl-5-(trifluoromethyl)-1H-pyrazol-3-yl]-7-fluoro-4-(methoxymethyl)-<br>MP: 156.5–157.5 | 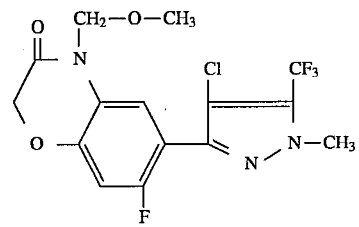 | C<br>H<br>Cl<br>F<br>N | 45.76<br>3.07<br>9.00<br>19.30<br>10.67 | 45.93<br>3.21<br><br><br> |
| 461 | 2H-1,4-benzoxazin-3(4H)-one,-6-[4-chloro-1-methyl-5-(trifluoromethyl)-1H-pyrazol-3-yl]-7-fluoro-4-methyl-<br>MP: 140.5–141.5 | 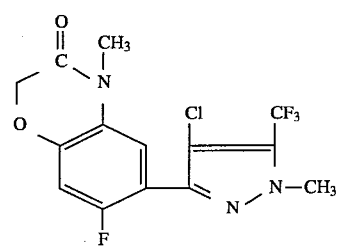 | C<br>H<br>Cl<br>F<br>N | 46.23<br>2.77<br>9.75<br>20.90<br>11.55 | 46.24<br>2.71<br><br><br>11.68 |
| 462 | 2H-1,4-benzoxazin-3(4H)-one,-6-[4-chloro-1-methyl-5-(trifluoromethyl)-1H-pyrazol-3-yl]-<br>MP: 216.0 | 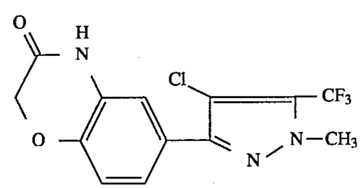 | C<br>H<br>Cl<br>F<br>N | 47.08<br>2.74<br>10.69<br>17.18<br>12.67 | 47.04<br>2.75<br><br><br>12.66 |

TABLE 6-continued

| Compound # | Name | Structure | Analysis (%) | | |
|---|---|---|---|---|---|
| | | | | Calc'd | Found |
| 463 | 2H-1,1-benzoxazin-3(4H)-one,-6-[4-chloro-1-methyl-5-(trifluoromethyl)-1H-pyrazol-3-yl]-7-fluoro-MP: 207.0 | 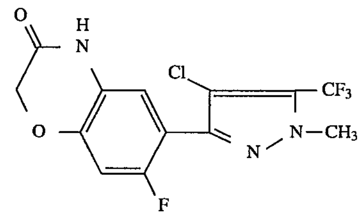 | C<br>H<br>Cl<br>F<br>N | 44.65<br>2.31<br>10.14<br>21.73<br>12.02 | 44.66<br>2.31<br><br><br>11.97 |
| 464 | 2H-1,4-benzoxazin-3(4H)-one,-6-[4-chloro-1-methyl-5-(trifluoromethyl)-1H-pyrazol-3-yl]-7-fluoro-2-methoxy-4-(2-propynyl)-MP: 101.0–103.0 | 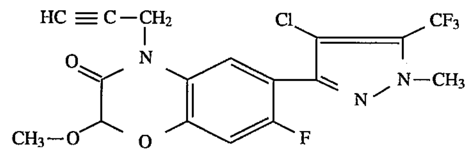 | C<br>H<br>Cl<br>F<br>N | 48.88<br>2.90<br>8.49<br>18.19<br>10.06 | 48.95<br>3.00 |
| 465 | 2H-1,4-benzoxazin-3(4H)-one,-6-[4-chloro-1-methyl-5-(trifluoromethyl)-1H-pyrazol-3-yl]-2,7-difluoro-4-(2-propynyl)-MP: 114.0–116.0 | 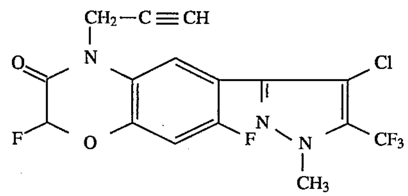 | C<br>H<br>Cl<br>F<br>N | 47.37<br>2.24<br>8.74<br>23.42<br>10.36 | 47.55<br>2.45 |
| 466 | 4H-1,4-benzoxazine-4-acetic acid,-6-[4-chloro-1-methyl-5-(trifluoromethyl)-1H-pyrazol-3-yl]-2,7-difluoro-3-oxo-,-ethyl ester MP: 114.5–116.0 | 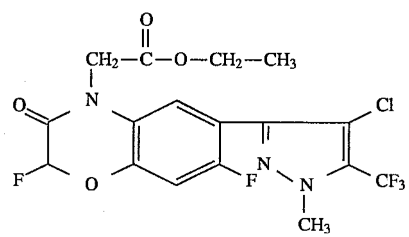 | C<br>H<br>Cl<br>F<br>N | 45.00<br>2.89<br>7.81<br>20.94<br>9.26 | 45.00<br>2.81 |

TABLE 6-continued

| Compound # | Name | Structure | Analysis (%) | | |
|---|---|---|---|---|---|
| | | | | Calc'd | Found |
| 467 | 2H-1,4-benzoxazin-3(4H)-one,-6-[4-chloro-1-methyl-5-(trifluoromethyl)-1H-pyrazol-3-yl]-2,7-difluoro- MP: 186.5–187.5 | 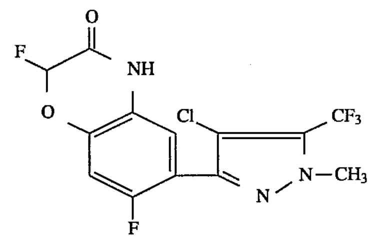 | C H Cl F N | 42.47 1.92 9.64 25.84 11.43 | 42.61 2.13 |
| 468 | 2H-1,4-benzoxazin-3(4H)-one,-6-[4-chloro-1-methyl-5-(trifluoromethyl)-1H-pyrazol-3-yl]-7-fluoro-2-methyl-4-(2-propynyl)- MP: 150.0–151.0 | 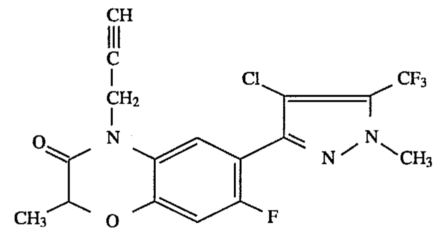 | C H Cl F N | 50.82 3.01 8.82 18.92 10.46 | 50.76 3.02 |
| 469 | 2H-1,4-benzoxazin-3(4H)-one,-6-[4-chloro-1-methyl-5-(trifluoromethyl)-1H-pyrazol-3-yl]-7-fluoro-2-methyl- MP: 187.0–189.0 | 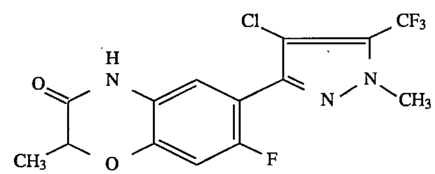 | C H Cl F N | 46.23 2.77 9.75 20.90 11.55 | 46.43 2.80 |
| 470 | propanoic acid,-2-[4-[4-chloro-1-methyl-5-(trifluoromethyl)-1H-pyrazol-3-yl]-5-fluoro-2-nitrophenoxy]-,-ethyl ester MP: 136.0–138.0 | 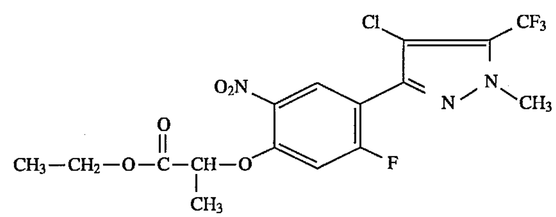 | C H Cl F N | 43.70 3.21 8.06 17.28 9.56 | 43.81 3.22 |

TABLE 6-continued

| Compound # | Name | Structure | | Analysis (%) | |
|---|---|---|---|---|---|
| | | | | Calc'd | Found |
| 471 | 2H-1,4-benzoxazin-3(4H)-one,-6-[4-chloro-1-methyl-5-(trifluoromethyl)-1H-pyrazol-3-yl]-2-ethyl-7-fluoro-4-(2-propynyl)-<br>MP: 126.5–127.5 | 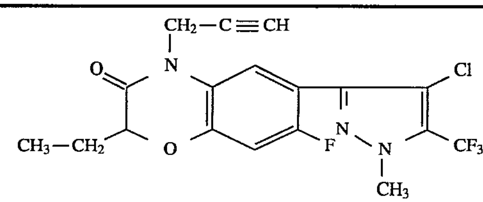 | C<br>H<br>Cl<br>F<br>N | 52.00<br>3.39<br>8.53<br>18.28<br>10.11 | 52.00<br>3.38 |
| 472 | 2H-1,4-benzoxazin-3(4H)-one,-6-[4-chloro-1-methyl-5-(trifluoromethyl)-1H-pyrazol-3-yl]-2-ethyl-7-fluoro-<br>MP: 191.0–192.0 | 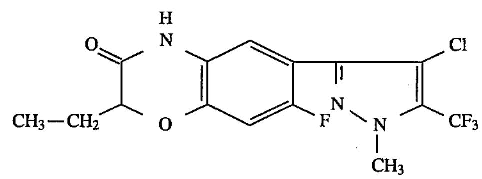 | C<br>H<br>Cl<br>F<br>N | 47.70<br>3.20<br>9.39<br>20.12<br>11.12 | 47.75<br>3.18 |
| 473 | 2H-1,4-benzoxazin-3(4H)-one,-6-[4-chloro-1-methyl-5-(trifluoromethyl)-1H-pyrazol-3-yl]-7-fluoro-2-phenyl-4-(2-propynyl)-<br>MP: 146.0–147.0 | 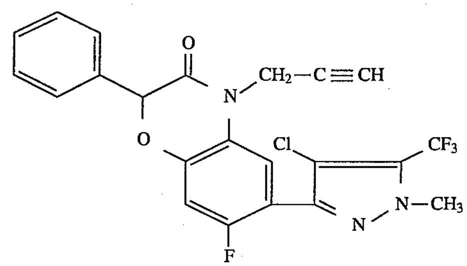 | C<br>H<br>Cl<br>F<br>N | 56.97<br>3.04<br>7.64<br>16.39<br>9.06 | 56.77<br>3.07 |
| 474 | 1H-benzimidazole,-6-[4-chloro-1-methyl-5-(trifluoromethyl)-1H-pyrazol-3-yl]-5-fluoro-1-(2-propenyl)-2-(trifluoromethyl)-<br>MP: 96.0 | 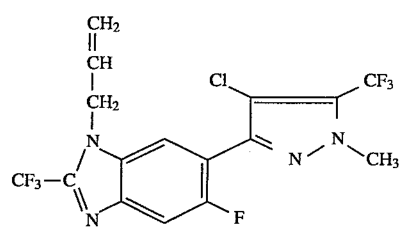 | C<br>H<br>Cl<br>F<br>N | 45.03<br>2.36<br>8.31<br>31.17<br>13.13 | 44.99<br>2.27<br><br><br>13.18 |

TABLE 6-continued

| Compound # | Name | Structure | Analysis (%) | | |
| --- | --- | --- | --- | --- | --- |
| | | | | Calc'd | Found |
| 475 | 2(1H)-quinoxalinone,-7-[4-chloro-1-methyl-5-(trifluoromethyl)-1H-pyrazol-3-yl]-6-fluoro-<br>MP: 250.0 | 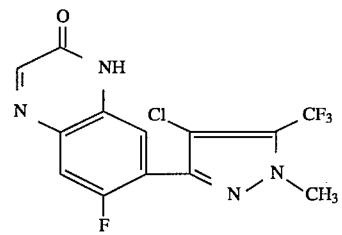 | C<br>H<br>Cl<br>F<br>N | 45.04<br>2.04<br>10.23<br>21.92<br>16.16 | 45.10<br>2.04<br><br><br>16.16 |
| 476 | 2H-1,4-benzoxazin-3(4H)-one,-7-[4-chloro-1-methyl-5-(trifluoromethyl)-1H-pyrazol-3-yl]-6-fluoro-<br>MP: 242.0 | 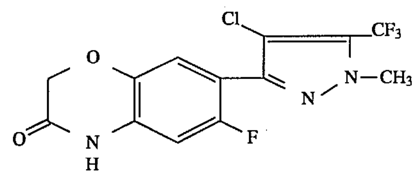 | C<br>H<br>Cl<br>F<br>N | 44.65<br>2.31<br>10.14<br>21.73<br>12.02 | 44.61<br>2.27<br><br><br>11.99 |
| 477 | 2H-1,4-benzothiazin-3(4H)-one,-7-[4-chloro-1-methyl-5-(trifluoromethyl)-1H-pyrazol-3-yl]-6-fluoro-<br>MP: 225.0 | 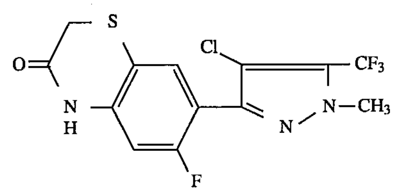 | C<br>H<br>Cl<br>F<br>N<br>S | 42.69<br>2.20<br>9.69<br>20.78<br>11.49<br>8.77 | 42.73<br>2.23<br><br><br>11.40<br>8.79 |
| 478 | 2(1H)-quinoxalinone,-7-[4-chloro-1-methyl-5-(trifluoromethyl)-1H-pyrazol-3-yl]-6-fluoro-3,-4-dihydro-<br>MP: 240.0 | 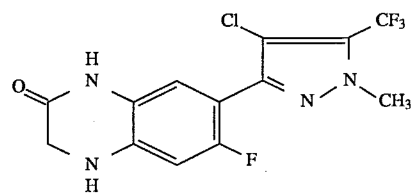 | C<br>H<br>Cl<br>F<br>N | 44.78<br>2.60<br>10.17<br>21.80<br>16.07 | 44.76<br>2.59<br><br><br>16.06 |
| 479 | 2H-1,4-benzoxazin-3(4H)-one,-7-[4-chloro-1-methyl-5-(trifluoromethyl)-1H-pyrazol-3-yl]-6-fluoro-4-(2-propynyl)-<br>MP: 181.0 | 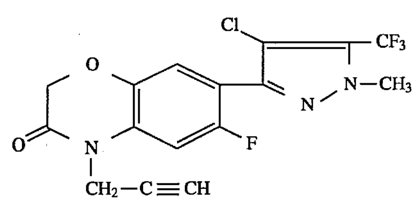 | C<br>H<br>Cl<br>F<br>N | 49.56<br>2.60<br>9.14<br>19.60<br>10.84 | 49.48<br>2.56<br><br><br>10.95 |

TABLE 6-continued

| Compound # | Name | Structure | | Analysis (%) | |
|---|---|---|---|---|---|
| | | | | Calc'd | Found |
| 480 | 1H-benzimidazole,-5-[4-chloro-1-methyl-5-(trifluoromethyl)-1H-pyrazol-3-yl]-6-fluoro-1-(2-propenyl)-2-(trifluoromethyl)- MP: nD 1.5186 (25° C.) | 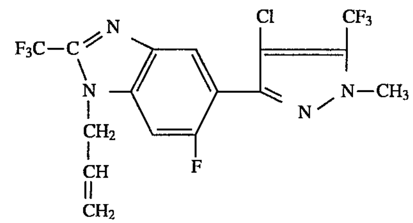 | C H Cl F N | 45.03 2.36 8.31 31.17 13.13 | 45.08 2.25 13.20 |
| 481 | 1H-pyrazole,- 4-chloro-3-[3-(chloromethylene)-5-fluoro-2,-3-dihydro-6-benzofuranyl]-1-methyl-5-(trifluoromethyl)-(Z)- MP: 140.5-142.5 | 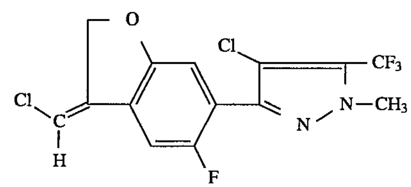 | C H Cl F N | 45.80 2.20 19.31 20.70 7.63 | 45.64 2.22 7.60 |
| 482 | 1H-pyrazole,- 4-chloro-3-[3-(chloromethylene)-5-fluoro-2,-3-dihydro-6-benzofuranyl]-1-methyl-5-(trifluoromethyl)-(E)- MP: 132.0-135.0 | 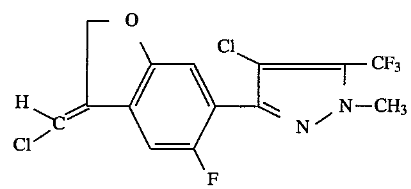 | C H Cl F N | 45.80 2.20 19.31 20.70 7.63 | 45.71 2.23 7.63 |
| 483 | phenol,-2,-4,-6-trichloro-3-[4-chloro-1-methyl-5-(trifluoromethyl)-1H-pyrazol-3-yl],-hemihydrate MP: 122.5 | 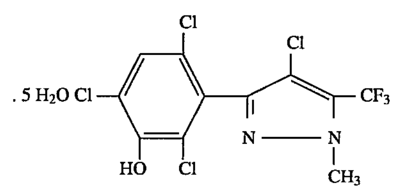 | C H Cl F N | 34.77 1.33 37.32 15.00 7.37 | 33.87 1.46 7.14 |
| 484 | 1H-pyrazole-1-acetic acid,-4-chloro-5-(4-chloro-2-fluoro-5-methoxyphenyl)-3-(trifluoromethyl)-,-methyl ester MP: clear glass (bp$_{0.065}$ 130-150° C.)* | 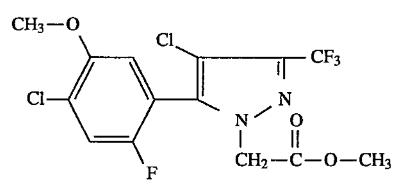 | C H Cl F N | 41.92 2.51 17.68 18.95 6.98 | 42.01 2.50 6.98 |

TABLE 6-continued

| Compound # | Name | Structure | Analysis (%) | | |
|---|---|---|---|---|---|
| | | | | Calc'd | Found |
| 485 | 1H-pyrazole,-3,-3'-[dithiobis(4-chloro-6-fluoro-1,3-phenylene)-[-bis]4-chloro-1-methyl-5-(trifluoromethyl)-<br>MP: 169.0 | 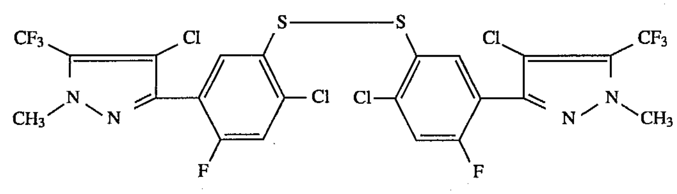 | C<br>H<br>Cl<br>F<br>N<br>S | 38.39<br>1.46<br>20.60<br>22.08<br>8.14<br>9.32 | 38.61<br>1.55<br><br><br>8.06<br>9.24 |
| 486 | 2(5H)-furanone,-3-[2-chloro-5-[4-chloro-1-methyl-5-(trifluoromethyl)-1H-pyrazol-3-yl]-4-fluorophenoxy]-dihydro-<br>MP: nD 1.5352 (25° C.) | 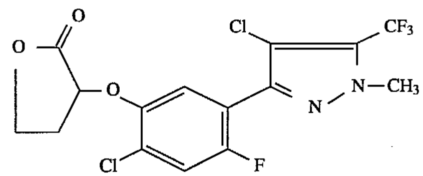 | C<br>H<br>Cl<br>F<br>N | 43.61<br>2.44<br>17.16<br>18.39<br>6.78 | 43.58<br>2.48<br><br><br>6.68 |
| 487 | benzenepropanenitrile,-<br>2-chloro-alpha-[2-chloro-5-[4-chloro-1-methyl-5-(trifluoromethyl)-1H-pyrazol-3-yl]-4-fluorophenyl]-5-[4-chloro-1-methyl-5-(trifluoromethyl)-1H-pyrazol-3-yl]-4-fluoro-<br>MP: 130.0–134.0 | 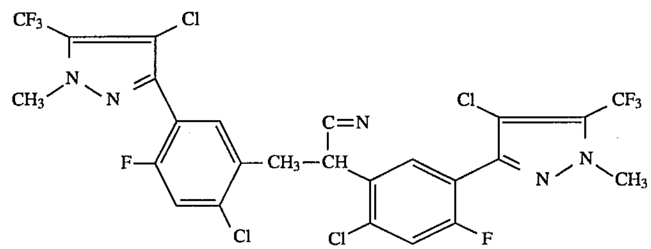 | C<br>H<br>Cl<br>F<br>N | 44.34<br>1.93<br>20.94<br>22.44<br>10.34 | 44.41<br>2.01<br><br><br>10.36 |
| 488 | oxazolidine,-2-[2-chloro-5-[4-chloro-1-methyl-5-(trifluoromethyl)-1H-pyrazol-3-yl]-4-fluorophenyl]-4,4-dimethyl-<br>MP: 106.0 | 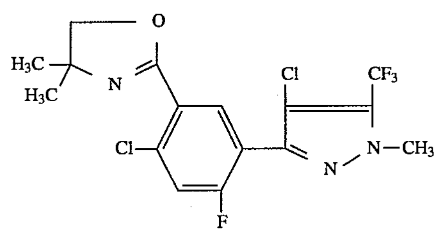 | C<br>H<br>Cl<br>F<br>N | 46.85<br>3.19<br>17.29<br>18.53<br>10.24 | 46.71<br>3.24<br><br><br>10.23 |

TABLE 6-continued

| Compound # | Name | Structure | Analysis (%) | |
|---|---|---|---|---|
| | | | Calc'd | Found |
| 489 | 1H-pyrazole,-4-chloro-3-(4-chloro-2-fluoro-5-methoxyphenyl)-1-(1-methylethyl)-5-(trifluoromethyl)- MP: nD 1.5192 (24° C.) | 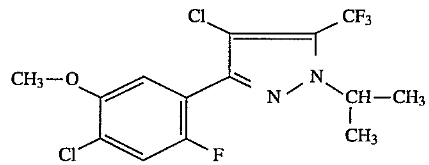 | C 45.30<br>H 3.26<br>Cl 19.10<br>F 20.48<br>N 7.55 | 45.19<br>3.27<br><br><br>7.49 |
| 490 | 1H-pyrazole,-4-chloro-3-[4-chloro-2-fluoro-5-[4-(methoxymethyl)-1,-3-dioxolan-2-yl]phenyl]-1-methyl-5-(trifluoromethyl)- MP: nD 1.5218 (25° C.) | 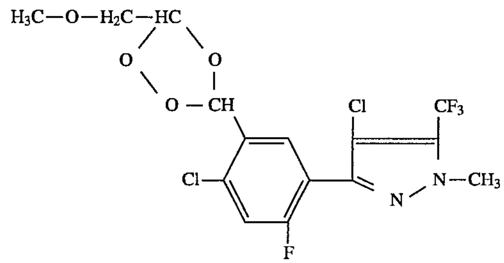 | C 44.77<br>H 3.29<br>Cl 16.52<br>F 17.71<br>N 6.53 | 44.75<br>3.32<br><br><br>6.56 |
| 491 | acetamide,-N-4-[4-chloro-1-methyl-5-(trifluoromethyl)-1H-pyrazol-3-yl]-5-fluoro-2-nitrophenyl]-2,-2,-2-trifluoro-N-2-propenyl- MP: nD 1.5143 (25° C.) | 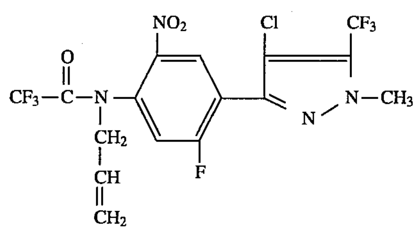 | C 40.48<br>H 2.12<br>Cl 7.47<br>F 28.02<br>N 11.80 | 40.71<br>2.13<br><br><br>11.70 |
| 492 | benzenamine,-4-[4-chloro-1-methyl-5-(trifluoromethyl)-1H-pyrazol-3-yl]-5-fluoro-2-nitro-N-2-propenyl- MP: 99.0 | 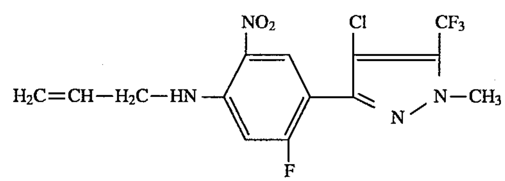 | C 44.40<br>H 2.93<br>Cl 9.36<br>F 20.07<br>N 14.79 | 44.53<br>2.97<br><br><br>14.76 |

TABLE 6-continued

| Compound # | Name | Structure | Analysis (%) | | |
|---|---|---|---|---|---|
| | | | | Calc'd | Found |
| 493 | glycine,-N-[4-[4-chloro-1-methyl-5-(trifluoromethyl)-1H-pyrazol-3-yl]-5-fluoro-2-nitrophenyl]-,-methyl ester MP: 176.0 | 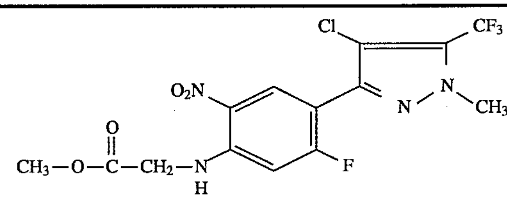 | C H Cl F N | 40.94 2.70 8.63 18.50 13.64 | 40.96 2.75 13.74 |
| 494 | butanoic acid,-2-[4-[4-chloro-1-methyl-5-(trifluoromethyl)-1H-pyrazol-3-yl]-5-fluoro-2-nitrophenoxy]-,-ethyl ester MP: 117.0–118.0 | 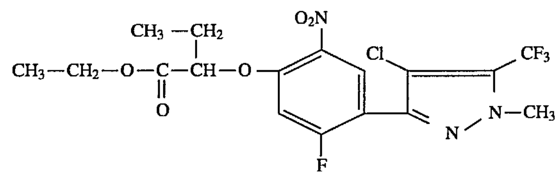 | C H Cl F N | 45.00 3.55 7.81 16.75 9.26 | 44.96 3.48 |
| 495 | acetic acid,-[4-[4-chloro-1-methyl-5-(trifluoromethyl)-1H-pyrazol-3-yl]-5-fluoro-2-nitrophenoxy]-methoxy-,-methyl ester MP: 113.5–114.5 | 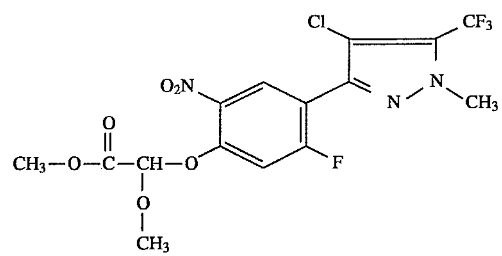 | C H Cl F N | 40.79 2.74 8.03 17.21 9.51 | 40.93 2.73 |
| 496 | benzeneacetic acid,-alpha-[4-[4-chloro-1-methyl-5-(trifluoromethyl]1-H-pyrazol-3-yl]-5-fluoro-2-nitrophenoxy]-,-methyl ester MP: 160.0–161.0 | 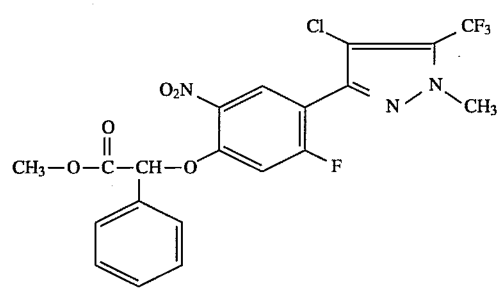 | C H Cl F N | 49.25 2.89 7.27 15.58 8.61 | 49.16 2.88 |

TABLE 6-continued

| Compound # | Name | Structure | | Analysis (%) | |
|---|---|---|---|---|---|
| | | | | Calc'd | Found |
| 497 | 1H-pyrazole,-4-chloro-3-[2-fluoro-4-[2-(methylthio)-ethoxy]-5-nitrophenyl]-1-methyl-5-(trifluoromethyl)-<br>MP: 69.0 | 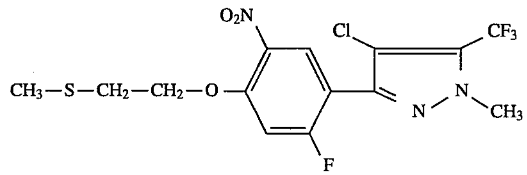 | C<br>H<br>Cl<br>F<br>N<br>S | 40.64<br>2.92<br>8.57<br>18.37<br>10.16<br>7.75 | 40.45<br>2.87<br><br><br>10.16 |
| 498 | acetic acid,-[4-[4-chloro-1-methyl-5-(trifluoromethyl)-1H-pyrazol-3-yl]-5-fluoro-2-nitrophenoxy]-,-butyl ester<br>MP: 65.0 | 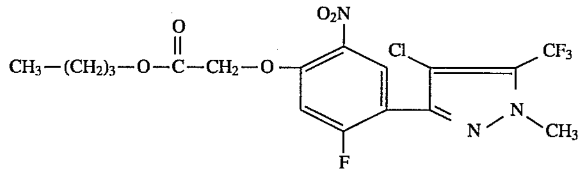 | C<br>H<br>Cl<br>F<br>N | 45.00<br>3.55<br>7.81<br>16.75<br>9.26 | 44.97<br>3.56<br><br><br>9.29 |
| 499 | 1H-pyrazole,-4-chloro-3-(2,4-dimethoxy-5-nitrophenyl)-1-methyl-5-(trifluoromethyl)-<br>MP: 158.0 | 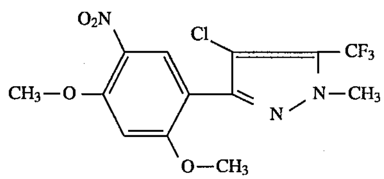 | C<br>H<br>Cl<br>F<br>N | 42.70<br>3.03<br>9.69<br>15.59<br>11.49 | 42.77<br>3.04<br><br><br>11.50 |
| 500 | cyclopropanecarboxamide,-1-bromo-N-[2-chloro-5-[4-chloro-1-methyl-5-(trifluoromethyl)-1H-pyrazol-3-yl]-4-fluorophenyl]-<br>MP: 80.0–94.0 | 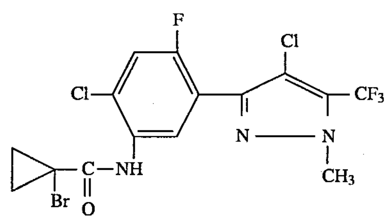 | C<br>H<br>Br<br>Cl<br>F<br>N | 37.92<br>2.12<br>16.82<br>14.93<br>16.00<br>8.85 | 38.41<br>2.26<br><br><br><br>8.80 |
| 501 | 1H-pyrazole,-4-chloro-1-(chloromethyl)-3-(2,4-difluorophenyl)-5-(trifluoromethyl)-<br>MP: nD 1.5096 (25° C.) | 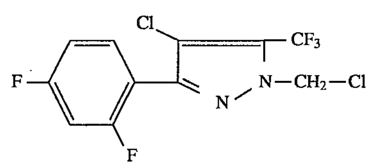 | C<br>H<br>Cl<br>F<br>N | 39.91<br>1.52<br>21.42<br>28.69<br>8.46 | 40.03<br>1.50<br><br><br>8.49 |

*Bulb-to-bulb distillation.

PRE-EMERGENCE HERBICIDE TESTS

As noted above, the compounds of this invention have been found to be surprisingly effective as herbicides.

The tests for pre-emergence herbicide activity are conducted as follows:

Topsoil is placed in an aluminum pan and compacted to a depth of 0.95 to 1.27 cm from the top of the pan. On the top of the soil is placed a predetermined number of seeds of each of several monocotyledonous and dicotyledonous annual plant species and/or vegetative propagules of various perennial plant species. A known amount of the active ingredient dissolved or suspended in an organic solvent, e.g., acetone, or water as carrier is then applied directly to the seed bed, which is then covered with a layer of untreated topsoil to level fill the pan. After treatment, the pans are moved to a greenhouse bench where they are watered from below as needed to give adequate moisture for germination and growth.

Approximately 10–14 days (usually 11 days) after seeding and treating, the pans are observed and the results (% inhibition) are recorded.

Tables 7 and 7A below summarize the results of the pre-emergence herbicidal activity tests of compounds of this invention in weeds. The herbicidal rating shown in these tables is the percent inhibition of each plant species. The plant species usually regarded as weeds which are utilized in one set of tests, the data for which are shown in the tables, are identified by letter headings above the columns in accordance with the following legend:

Yens—Yellow nutsedge

Anbg—Annual bluegrass

Sejg—Seedling johnsongrass

Dobr—Downy Brome

Bygr—Barnyardgrass

Mogl—Morningglory

Cobu—Cocklebur

Vele—Velvetleaf

Inmu—Indian Mustard

Wibw—Wild buckwheat

Where noted in the tables below, the symbol "C" represents 100% control and the symbol "N" indicates that the species was planted, but no data obtained for one reason or another. Compound Nos. 1–61 are intermediate compounds and do not appear in Tables 7 and below.

TABLE 7

PREEMERGENCE TESTS % PLANT INHIBITION

| Cpd. No. | | Rate kg/ha | Yens | Anbg | Sejg | Dobr | Bygr | Mogl | Cobu | Vele | Inmu | Wibw |
|---|---|---|---|---|---|---|---|---|---|---|---|---|
| 62 | | 11.21 | 0 | 0 | 30 | 0 | 20 | 30 | 0 | 60 | 20 | 20 |
| 63 | | 11.21 | 0 | C | C | C | C | C | 60 | C | C | C |
| 64 | | 11.21 | 10 | 90 | 80 | 90 | 80 | 80 | 10 | C | C | C |
| 65 | ) | 11.21 | 0 | 70 | 70 | 0 | 30 | 20 | 0 | 90 | N | 80 |
| 66 | | 11.21 | 0 | 50 | 90 | 60 | 10 | C | 20 | 90 | 50 | 90 |
| 67 | | 11.21 | 0 | 40 | 40 | 40 | 0 | 90 | 0 | 80 | 50 | 90 |
| 68 | * | 11.21 | 30 | 0 | 10 | 0 | 10 | 30 | 0 | 40 | 0 | N |
| 69 | | 11.21 | 0 | 0 | 0 | 0 | 0 | 30 | 0 | 50 | 0 | 0 |
| 70 | | 11.21 | 0 | 40 | 80 | 20 | 40 | 80 | 20 | 90 | 80 | 80 |
| 71 | | 11.21 | 0 | 90 | 40 | 10 | 0 | 30 | 0 | 60 | 30 | 70 |
| 72 | | 11.21 | 0 | 20 | 60 | 20 | 60 | 40 | 20 | 90 | 90 | 90 |
| 73 | | 11.21 | 0 | 0 | 0 | 0 | 0 | 0 | 0 | 50 | 20 | 0 |
| 74 | | 1.12 | 0 | 10 | 60 | 20 | 20 | 50 | 0 | 90 | 90 | C |
| 75 | | 11.21 | 20 | 0 | 50 | 20 | 20 | 90 | 10 | 80 | 30 | 50 |
| 76 | | 1.12 | 0 | 10 | 0 | 10 | 0 | 40 | 20 | 50 | 60 | C |
| 77 | | 11.21 | 0 | 80 | 40 | 10 | 30 | 0 | 0 | 30 | 30 | 20 |
| 78 | | 11.21 | 0 | 0 | 0 | 0 | 0 | 0 | 0 | 0 | 0 | 0 |
| 79 | | 11.21 | 20 | 90 | 80 | 80 | 80 | C | 30 | C | C | C |
| 80 | | 11.21 | 0 | 90 | 80 | 70 | 70 | 60 | 60 | C | 80 | 90 |
| 81 | ) | 11.21 | 0 | 60 | 90 | 80 | 60 | 30 | 20 | 90 | 20 | C |
| 82 | | 11.21 | 30 | 60 | C | C | C | C | 40 | C | 80 | C |
| 83 | | 11.21 | 20 | 40 | C | 90 | 60 | 30 | 40 | 90 | 60 | 90 |
| 84 | | 11.21 | 30 | C | C | C | C | 90 | 80 | C | C | C |
| 85 | | 11.21 | 0 | C | C | C | C | C | 40 | C | C | C |
| 86 | | 11.21 | 0 | 0 | 0 | 0 | 0 | 20 | 10 | 90 | 30 | C |
| 87 | | 11.21 | 10 | 10 | 30 | 20 | 40 | 70 | 10 | 90 | 70 | 90 |
| 88 | | 11.21 | 10 | 20 | 30 | 10 | 10 | 10 | 20 | 80 | 20 | C |
| 90 | | 11.21 | 0 | 10 | 50 | 10 | 10 | 10 | 0 | 20 | 10 | 30 |
| 91 | | 1.12 | 0 | 0 | 0 | 0 | 0 | 90 | 20 | C | 90 | 70 |
| 92 | | 1.12 | 0 | 0 | 0 | 0 | 0 | 80 | 20 | 90 | 20 | 80 |
| 94 | | 1.12 | 20 | C | C | C | C | 90 | 60 | C | C | C |
| 95 | | 1.12 | 20 | 30 | 50 | 20 | 50 | 40 | 20 | 90 | 80 | C |
| 96 | | 1.12 | 20 | C | 90 | C | 80 | C | 60 | C | C | C |
| 97 | | 1.12 | 20 | 80 | 50 | 80 | 50 | 40 | 90 | C | 90 | C |
| 99 | | 11.21 | 30 | 80 | 90 | C | 90 | 90 | 80 | C | C | C |
| 100 | | 1.12 | 0 | 90 | 90 | C | 70 | 80 | 20 | C | C | C |
| 101 | | 1.12 | 0 | 70 | 80 | 80 | 40 | 80 | 30 | C | C | 90 |
| 102 | | 1.12 | 20 | 60 | 90 | 80 | 80 | C | 30 | C | C | C |
| 103 | | 1.12 | 0 | 20 | 40 | 70 | 20 | 60 | 0 | 50 | 40 | C |
| 104 | | 1.12 | 0 | 20 | 80 | 80 | 10 | 80 | 20 | 90 | 80 | 70 |
| 105 | | 1.12 | 20 | 0 | 60 | 40 | 70 | 80 | 10 | 90 | 80 | 80 |
| 106 | | 1.12 | 0 | 30 | 80 | 80 | 80 | 60 | 20 | 80 | 90 | C |

TABLE 7-continued

| | PREEMERGENCE TESTS % PLANT INHIBITION | | | | | | | | | | |
|---|---|---|---|---|---|---|---|---|---|---|---|
| Cpd. No. | | Rate kg/ha | Yens | Anbg | Sejg | Dobr | Bygr | Mogl | Cobu | Vele | Inmu | Wibw |
| 107 | | 1.12 | 0 | 20 | 40 | 30 | 80 | C | 20 | 90 | 80 | 80 |
| 108 | | 11.21 | 20 | 50 | 90 | C | C | 90 | 80 | C | C | C |
| 109 | | 1.12 | 0 | 20 | 80 | 20 | 90 | 70 | 30 | 90 | 90 | C |
| 110 | | 1.12 | 0 | 0 | 0 | 0 | 20 | 70 | 50 | C | 80 | 70 |
| 111 | | 11.21 | 60 | 80 | 80 | 70 | 40 | C | 90 | C | C | C |
| 112 | | 11.21 | 80 | C | 90 | 20 | C | C | 40 | C | C | 90 |
| 113 | | 11.21 | 0 | 10 | 30 | 0 | 80 | 30 | 0 | 80 | 80 | 40 |
| 114 | | 11.21 | 90 | C | 90 | 60 | C | C | 70 | C | C | C |
| 115 | | 1.12 | 0 | 40 | 70 | 70 | 80 | 80 | 20 | C | C | 90 |
| 116 | | 1.12 | 0 | 90 | 90 | 80 | 90 | 90 | 50 | C | 90 | C |
| 117 | | 1.12 | 0 | C | 70 | 90 | C | 90 | 70 | C | C | C |
| 118 | | 1.12 | 0 | C | 90 | C | 90 | C | 80 | 90 | C | C |
| 119 | | 11.21 | 70 | 10 | 80 | 80 | C | C | C | C | C | C |
| 120 | | 1.12 | 10 | 70 | 80 | 70 | 80 | 80 | 30 | C | 90 | C |
| 121 | | 11.21 | 70 | C | 80 | 70 | C | C | 60 | C | C | C |
| 122 | | 1.12 | 0 | 20 | 40 | 20 | 80 | 80 | 40 | C | C | 70 |
| 123 | | 1.12 | 30 | 0 | 40 | 70 | 30 | C | 50 | C | 80 | 90 |
| 124 | | 11.21 | 20 | C | C | C | C | C | C | C | C | C |
| 125 | | 1.12 | 0 | C | C | 90 | C | 90 | 30 | C | C | C |
| 126 | | 1.12 | 0 | C | C | C | C | C | 50 | C | C | C |
| 127 | | 1.12 | 0 | 0 | 20 | 0 | 30 | 70 | 20 | C | 90 | C |
| 128 | | 1.12 | 0 | 0 | 30 | 0 | 0 | 80 | 70 | C | 70 | C |
| 129 | | 1.12 | 0 | 0 | 60 | 40 | 20 | C | 90 | C | 90 | C |
| 130 | | 1.12 | 20 | 0 | 70 | 30 | 30 | C | 90 | C | C | 90 |
| 131 | | 1.12 | 20 | 0 | 70 | 30 | 40 | C | 80 | C | 90 | C |
| 132 | | 11.21 | 30 | 60 | 70 | 80 | 90 | C | 70 | C | 90 | C |
| 133 | | 1.12 | 20 | 20 | 80 | 0 | 80 | 70 | 40 | C | C | 70 |
| 134 | | 1.12 | 0 | 50 | 40 | 70 | 10 | 20 | 30 | 70 | 60 | 90 |
| 135 | | 1.12 | 0 | C | C | C | C | 90 | 90 | C | C | C |
| 137 | | 1.12 | 20 | 70 | 50 | 80 | 70 | C | C | C | C | 90 |
| 138 | | 1.12 | 20 | 40 | 30 | 90 | 50 | C | C | C | C | C |
| 142 | | 1.12 | 0 | 10 | 20 | 70 | 40 | C | 60 | C | 90 | 50 |
| 143 | | 1.12 | 10 | 10 | 40 | 20 | 20 | 90 | 80 | C | C | C |
| 144 | | 1.12 | 10 | 10 | 20 | 10 | 30 | 80 | C | C | 80 | 70 |
| 145 | | 1.12 | 60 | 0 | 30 | 20 | 30 | C | 70 | C | C | 70 |
| 146 | | 1.12 | 20 | C | C | C | C | C | 90 | C | C | C |
| 147 | | 1.12 | 30 | 0 | 40 | 10 | 40 | 80 | 20 | C | 80 | 70 |
| 148 | | 1.12 | 0 | 70 | 50 | 80 | 90 | C | 90 | C | C | C |
| 149 | | 1.12 | 20 | 0 | 20 | 0 | 20 | 90 | 30 | C | 70 | 60 |
| 150 | | 1.12 | 0 | 70 | 90 | 80 | 60 | 40 | 60 | 90 | 80 | C |
| 151 | | 1.12 | 0 | C | C | C | 90 | 70 | 90 | 90 | 90 | C |
| 152 | | 1.12 | 0 | 70 | 20 | 70 | 60 | 90 | 20 | C | 90 | 90 |
| 153 | | 1.12 | 30 | C | C | 50 | C | 90 | 10 | C | C | 90 |
| 154 | | 1.12 | 30 | 10 | C | 10 | 90 | C | C | C | C | C |
| 155 | | 1.12 | 0 | 90 | 90 | 30 | 80 | 90 | 70 | C | C | C |
| 156 | | 1.12 | 20 | 20 | C | 20 | 90 | C | 80 | C | C | 90 |
| 157 | | 1.12 | 50 | C | 90 | 80 | C | C | 80 | C | C | C |
| 158 | | 1.12 | 10 | 30 | 80 | 70 | 80 | C | 50 | C | C | 90 |
| 159 | ( | 11.21 | C | 90 | C | 90 | C | C | C | C | C | C |
| 160 | | 1.12 | 0 | 20 | 80 | 50 | 30 | 30 | 40 | 40 | 20 | 90 |
| 161 | | 11.21 | 60 | 40 | 90 | 80 | C | C | C | C | C | C |
| 162 | | 1.12 | 20 | 80 | C | 90 | 70 | 80 | 70 | 90 | 80 | C |
| 163 | | 11.21 | 50 | C | C | C | C | C | C | C | C | C |
| 164 | + | 11.21 | 10 | 70 | 80 | C | 20 | C | 40 | C | C | C |
| 165 | | 11.21 | 40 | C | C | C | C | C | C | C | C | C |
| 166 | | 1.12 | 30 | 70 | 80 | 80 | 40 | 50 | 50 | 90 | 90 | C |
| 167 | @ | 11.21 | 0 | 50 | 80 | C | 70 | 50 | 40 | 90 | C | C |
| 168 | | 11.21 | 0 | 0 | 0 | 0 | 0 | 30 | 30 | 80 | 30 | C |
| 169 | | 1.12 | 0 | 20 | 80 | C | 50 | 40 | 30 | 70 | 80 | 90 |
| 170 | @ | 11.21 | 0 | 30 | 90 | C | 80 | C | 40 | C | C | C |
| 171 | | 11.21 | 20 | 40 | 80 | 50 | 90 | 60 | 40 | C | 70 | 80 |
| 172 | | 1.12 | 20 | 30 | 0 | 0 | 20 | 0 | 0 | 30 | 80 | 80 |
| 173 | | 1.12 | 20 | C | 60 | 90 | 70 | 60 | 30 | 80 | 80 | 80 |
| 174 | | 1.12 | 0 | 30 | 80 | 60 | 50 | 70 | 30 | 90 | 90 | 90 |
| 175 | | 11.21 | 0 | 80 | 20 | 40 | 70 | 80 | 10 | 80 | 10 | 90 |
| 176 | | 11.21 | 20 | C | C | C | 90 | C | 80 | C | C | C |
| 177 | | 11.21 | 20 | C | C | 90 | 90 | C | C | 90 | C | C |
| 179 | | 1.12 | 0 | 70 | 90 | 90 | 70 | 80 | 80 | 90 | C | C |
| 180 | | 1.12 | 0 | 0 | 0 | 40 | 30 | 90 | 80 | C | 90 | C |
| 181 | | 11.21 | 30 | C | 80 | C | 90 | C | C | C | C | C |
| 182 | | 11.21 | 90 | C | C | C | C | C | C | C | C | C |
| 183 | + | 1.12 | 0 | 50 | 80 | 90 | 20 | 70 | 70 | 90 | 90 | C |
| 184 | | 11.21 | 0 | 20 | 0 | 20 | 30 | C | 60 | C | C | C |
| 185 | | 11.21 | 20 | C | 80 | C | C | C | C | C | C | C |

TABLE 7-continued

PREEMERGENCE TESTS % PLANT INHIBITION

| Cpd. No. | | Rate kg/ha | Yens | Anbg | Sejg | Dobr | Bygr | Mogl | Cobu | Vele | Inmu | Wibw |
|---|---|---|---|---|---|---|---|---|---|---|---|---|
| 186 | | 1.12 | 0 | 40 | 60 | C | 20 | 80 | 70 | C | 80 | C |
| 187 | ÷ | 1.12 | 0 | 30 | 70 | 50 | 20 | 40 | 40 | 80 | C | C |
| 188 | | 11.21 | 20 | 60 | 80 | 70 | 80 | C | 80 | C | 80 | C |
| 189 | | 1.12 | 0 | 0 | 0 | 10 | 0 | 50 | 30 | 80 | 80 | 80 |
| 190 | | 1.12 | 0 | 20 | 20 | 10 | 10 | C | 30 | C | 90 | C |
| 191 | | 11.21 | 0 | 0 | 20 | 30 | 70 | 70 | 40 | C | 80 | C |
| 192 | | 11.21 | 0 | C | 90 | C | 90 | 90 | 90 | C | C | C |
| 193 | | 11.21 | 50 | C | 50 | 60 | 40 | C | C | C | C | C |
| 194 | | 1.12 | 20 | 0 | 30 | 20 | 0 | 80 | 30 | 90 | 60 | 80 |
| 195 | | 1.12 | 0 | 0 | 20 | 20 | 50 | C | 90 | C | 80 | 30 |
| | | 1.12 | 0 | N | 0 | N | 0 | 0 | 0 | N | N | N |
| 196 | | 1.12 | 50 | 0 | 0 | 20 | 60 | 80 | 50 | C | C | 70 |
| 197 | | 11.21 | 0 | 0 | 30 | 30 | 80 | 60 | 80 | C | C | C |
| 199 | | 1.12 | 0 | 0 | 20 | 20 | 20 | 70 | 40 | C | 80 | 60 |
| 200 | | 1.12 | 0 | 0 | 0 | 0 | 30 | C | 80 | C | 90 | 60 |
| 201 | | 1.12 | 0 | 0 | 20 | 0 | 30 | 70 | 70 | C | 80 | 30 |
| 202 | | 1.12 | 0 | 0 | 20 | 20 | 20 | 60 | 50 | 60 | 70 | 80 |
| 204 | | 1.12 | 0 | 0 | 0 | 0 | 0 | 0 | 0 | 0 | 0 | 0 |
| 206 | | 11.21 | 0 | 0 | 20 | 0 | 10 | 20 | 20 | 0 | 20 | 40 |
| 207 | @ | 1.12 | 0 | 0 | 0 | 0 | 0 | 0 | 0 | 0 | 0 | 0 |
| 208 | | 1.12 | 30 | 50 | 80 | C | 60 | 60 | 80 | 80 | 70 | C |
| 209 | | 1.12 | 0 | 0 | 0 | 0 | 20 | 20 | 0 | 20 | 0 | 0 |
| 210 | | 1.12 | 20 | 20 | 80 | 70 | 40 | 80 | 30 | 80 | 80 | C |
| 211 | | 1.12 | 10 | 80 | C | C | C | C | 80 | C | C | C |
| 212 | | 1.12 | 20 | 30 | 50 | 80 | 70 | 80 | 70 | C | C | 90 |
| 213 | | 1.12 | 20 | 90 | 50 | 90 | C | 60 | 50 | C | C | 80 |
| 214 | | 1.12 | 30 | 80 | 70 | 70 | 90 | 80 | 50 | C | C | C |
| 215 | | 1.12 | 0 | 60 | 40 | 20 | 80 | 80 | 30 | C | C | 90 |
| 216 | | 1.12 | 30 | C | C | C | 90 | C | 80 | C | C | C |
| 217 | | 1.12 | 20 | C | C | C | C | C | 80 | C | C | C |
| 218 | | 1.12 | 0 | 50 | 40 | 70 | 80 | C | 70 | C | C | C |
| 219 | | 1.12 | 30 | 60 | 50 | 60 | 70 | 90 | 90 | C | C | 70 |
| 220 | | 1.12 | 50 | 70 | 60 | 70 | 70 | 80 | 90 | 90 | 90 | 60 |
| 221 | | 1.12 | 30 | 30 | 50 | 50 | 20 | 80 | 80 | 80 | C | 30 |
| 222 | | 1.12 | 40 | 80 | 30 | 60 | 80 | 70 | 80 | C | C | C |
| 223 | | 1.12 | 40 | 60 | 50 | 60 | 60 | 80 | 90 | C | 90 | 40 |
| 224 | | 1.12 | 0 | 40 | 70 | 80 | 70 | 60 | C | C | 50 | C |
| | | 1.12 | 0 | N | N | N | 0 | 0 | 0 | N | N | N |
| 225 | | 1.12 | 30 | 90 | 60 | 80 | 60 | 50 | 80 | C | C | 60 |
| 226 | | 1.12 | 30 | 20 | 40 | 50 | 50 | 80 | 90 | 90 | C | 50 |
| 227 | | 1.12 | 30 | 50 | 50 | 40 | 70 | 80 | 90 | C | C | 60 |
| 228 | | 1.12 | 20 | 60 | 50 | 80 | 50 | 80 | C | 90 | C | 60 |
| 229 | | 1.12 | 60 | C | C | C | 90 | C | 90 | C | C | C |
| 230 | | 1.12 | 20 | 60 | 80 | 60 | 90 | 90 | 60 | C | C | C |
| 231 | | 1.12 | 0 | 20 | 40 | 50 | 30 | 0 | 40 | 40 | 20 | 20 |
| 232 | | 1.12 | 40 | C | 80 | 70 | 90 | C | 30 | C | C | C |
| 233 | | 1.12 | 30 | 80 | 70 | 50 | 90 | 90 | 30 | C | C | C |
| 234 | | 1.12 | 20 | 40 | 50 | 30 | 40 | 70 | 30 | C | C | 90 |
| 235 | | 1.12 | 30 | 90 | 70 | 30 | C | C | 30 | C | C | C |
| 236 | | 1.12 | 30 | 90 | 90 | C | 50 | C | C | C | C | C |
| 237 | | 1.12 | 60 | 90 | 90 | 80 | C | C | 40 | C | C | C |
| 238 | | 1.12 | 50 | 10 | 20 | 20 | 20 | 70 | C | C | C | 80 |
| | | 1.12 | 40 | 10 | 10 | 0 | 0 | 80 | C | C | C | 70 |
| 239 | | 1.12 | 30 | 30 | 50 | 50 | 30 | 80 | 90 | C | C | 30 |
| 240 | | 1.12 | 0 | 80 | 90 | C | 80 | C | 90 | C | C | C |
| 241 | | 1.12 | 20 | C | 60 | 90 | 60 | 50 | 50 | C | 70 | 80 |
| 242 | | 1.12 | 30 | 90 | 30 | 90 | 40 | 80 | 60 | C | C | 80 |
| 243 | | 1.12 | 20 | 80 | 30 | 60 | 30 | 60 | 70 | C | 90 | 60 |
| 244 | | 1.12 | 30 | 0 | 10 | 50 | 0 | 0 | 0 | 20 | 0 | 10 |
| 245 | | 1.12 | 0 | 60 | 60 | 30 | 80 | 80 | 30 | 90 | C | C |
| 246 | | 1.12 | 0 | 90 | 80 | C | 70 | 80 | 90 | 90 | C | C |
| 247 | | 1.12 | 30 | 20 | 50 | 20 | 50 | C | 70 | C | 90 | 80 |
| 248 | | 1.12 | 30 | 30 | 20 | 0 | 40 | 90 | 50 | C | 90 | 90 |
| 249 | | 1.12 | 60 | C | 90 | 80 | C | C | 50 | C | C | C |
| 250 | | 1.12 | 0 | 30 | 60 | 90 | 80 | 90 | 10 | C | 70 | C |
| 253 | | 1.12 | 20 | 30 | 60 | 40 | 80 | 90 | 20 | 90 | 90 | 90 |
| 254 | | 1.12 | 0 | 80 | 70 | 80 | 70 | 20 | 30 | C | 70 | C |
| 255 | | 1.12 | 0 | 0 | 30 | 40 | 0 | 90 | 60 | 90 | 90 | 80 |
| 256 | | 1.12 | 0 | 60 | 60 | 40 | 80 | 80 | 40 | C | C | C |
| 257 | | 1.12 | 0 | 10 | 20 | 20 | 0 | 70 | 30 | 90 | 80 | 80 |
| 258 | | 1.12 | 0 | 20 | 40 | 10 | 20 | 80 | C | 80 | C | 70 |
| 259 | | 1.12 | 0 | 0 | 0 | 0 | 0 | 60 | N | 30 | 20 | 0 |
| 260 | | 1.12 | 0 | 20 | 30 | C | 20 | 30 | 30 | 40 | 50 | 80 |
| 261 | | 11.21 | 30 | C | C | C | C | C | C | C | C | C |

TABLE 7-continued

PREEMERGENCE TESTS % PLANT INHIBITION

| Cpd. No. | | Rate kg/ha | Yens | Anbg | Sejg | Dobr | Bygr | Mogl | Cobu | Vele | Inmu | Wibw |
|---|---|---|---|---|---|---|---|---|---|---|---|---|
| 262 | | 1.12 | 40 | C | C | C | C | C | 80 | C | C | C |
| 263 | | 1.12 | 0 | C | C | C | C | C | C | C | C | C |
| 264 | | 1.12 | 30 | 60 | 70 | C | 80 | C | 70 | C | 90 | C |
| 265 | | 1.12 | 0 | 90 | 80 | 90 | 20 | 20 | 20 | 70 | 60 | C |
| 266 | | 1.12 | 30 | 70 | 50 | C | 90 | 70 | 40 | 40 | 80 | C |
| 267 | | 1.12 | 30 | 60 | 90 | 90 | 70 | 70 | 70 | 90 | 80 | C |
| 268 | | 1.12 | 0 | 40 | 60 | C | 60 | 70 | 60 | 90 | 80 | C |
| 269 | | 1.12 | 20 | C | C | C | 90 | 90 | 60 | C | C | C |
| 270 | | 1.12 | 30 | 70 | 70 | C | 90 | C | 60 | C | C | C |
| 271 | | 1.12 | 30 | 50 | 80 | 80 | 80 | 80 | 70 | 80 | 80 | C |
| 272 | | 1.12 | 40 | 20 | 80 | 70 | 90 | C | 70 | C | C | C |
| 273 | | 1.12 | 20 | 80 | 70 | 60 | C | C | 40 | C | C | C |
| 274 | | 1.12 | 0 | 20 | 40 | 20 | 80 | 80 | 0 | C | C | 60 |
| 275 | | 1.12 | 20 | 20 | 40 | 20 | 80 | C | 70 | C | C | C |
| 276 | | 1.12 | 20 | C | C | C | C | C | 80 | C | C | C |
| 277 | | 1.12 | 20 | C | C | C | C | C | 50 | C | C | C |
| 278 | | 1.12 | 20 | C | 90 | C | 90 | C | 70 | C | C | C |
| 279 | | 11.21 | C | 90 | C | C | 90 | C | C | C | C | C |
| 280 | | 11.21 | 90 | 50 | 80 | 40 | 80 | C | C | C | 90 | C |
| 281 | | 1.12 | 0 | 0 | 0 | 0 | 0 | 40 | 80 | 70 | 20 | 50 |
| 282 | | 1.12 | 40 | 20 | 30 | 20 | 20 | 90 | 30 | C | 30 | 90 |
| 283 | | 1.12 | 40 | 20 | 20 | 0 | 0 | C | C | C | 70 | 70 |
| 286 | | 1.12 | 0 | 0 | 20 | 20 | 50 | C | C | C | 0 | 80 |
| 289 | | 1.12 | 70 | 30 | 70 | 20 | 20 | 90 | 50 | C | 40 | 90 |
| 290 | | 1.12 | 80 | 30 | 30 | 20 | 20 | C | C | C | 40 | 90 |
| 291 | | 1.12 | 30 | 30 | 40 | 20 | 20 | C | C | C | 40 | C |
| 292 | | 1.12 | 40 | 20 | 40 | 20 | 20 | C | 40 | 80 | 30 | 80 |
| 293 | | 1.12 | 20 | 0 | 20 | 0 | 20 | C | 80 | C | 0 | 70 |
| 294 | + | 1.12 | 0 | 0 | 20 | 20 | 20 | 70 | 80 | 70 | 0 | 90 |
| 295 | | 1.12 | 0 | 40 | 60 | 50 | 50 | 60 | 30 | 70 | 60 | C |
| 296 | | 1.12 | 30 | 0 | 0 | 0 | 30 | 90 | 90 | C | C | C |
| 297 | | 1.12 | 0 | 20 | 40 | 60 | 80 | 20 | 10 | 90 | 70 | 90 |
| 298 | | 1.12 | 50 | 30 | 30 | 20 | 80 | C | 40 | C | C | C |
| 299 | | 1.12 | 0 | 0 | 20 | 20 | 70 | C | 80 | C | C | 70 |
| 300 | | 1.12 | 20 | 0 | 0 | 0 | 0 | C | 80 | C | 40 | 50 |
| 301 | | 11.21 | 0 | 0 | 0 | 90 | 20 | 30 | 0 | 40 | 40 | 90 |
| 302 | | 1.12 | 0 | C | 90 | C | C | C | 90 | C | C | C |
| 304 | | 1.12 | 10 | 80 | 80 | C | 80 | C | 90 | C | C | C |
| 305 | | 1.12 | 0 | 90 | 90 | C | 90 | 70 | 30 | C | 90 | C |
| 306 | | 1.12 | 0 | 60 | 40 | C | 80 | 80 | 70 | C | C | C |
| 307 | @ | 1.12 | 30 | 80 | 80 | C | 70 | C | 90 | 90 | 90 | C |
| 308 | | 1.12 | 40 | C | C | C | C | C | 80 | C | C | C |
| 309 | | 1.12 | 40 | C | 90 | C | C | C | 80 | C | C | C |
| 310 | | 1.12 | 20 | 90 | 70 | 20 | 80 | C | 30 | C | C | C |
| 311 | | 1.12 | 60 | C | 90 | 90 | C | C | 60 | C | C | C |
| 312 | | 11.21 | 60 | C | C | C | C | C | C | C | C | C |
| 313 | | 1.12 | 30 | C | C | C | C | C | 90 | C | C | C |
| 314 | | 1.12 | 20 | 80 | 90 | C | 90 | C | 80 | C | C | C |
| 316 | | 1.12 | 0 | C | 90 | C | 90 | 90 | 50 | C | C | C |
| 317 | | 1.12 | 10 | 90 | 70 | 60 | 60 | 90 | C | C | 80 | C |
| 318 | | 11.21 | 70 | C | 90 | C | C | C | C | C | C | C |
| 319 | | 1.12 | 20 | 80 | 40 | 70 | 30 | 90 | 50 | C | 80 | C |
| 320 | | 1.12 | 0 | 60 | 40 | 40 | 30 | C | 90 | C | 80 | C |
| 321 | | 1.12 | 20 | 20 | 30 | 80 | 60 | 60 | 20 | C | 50 | C |
| 322 | | 1.12 | 0 | 20 | 30 | 80 | 30 | C | 30 | C | 60 | C |
| 323 | | 1.12 | 0 | 60 | 70 | 90 | 70 | 80 | 20 | C | 50 | C |
| 324 | | 1.12 | 20 | 70 | 50 | 70 | 80 | C | 30 | 90 | 90 | C |
| 325 | | 11.21 | 0 | 90 | C | C | C | 90 | 90 | C | C | C |
| 326 | | 11.21 | 20 | C | 90 | C | 90 | C | 80 | C | C | C |
| 327 | | 11.21 | 0 | 0 | 0 | 0 | 0 | 0 | 0 | 20 | 0 | 0 |
| 328 | | 1.12 | 0 | 10 | 40 | 90 | 0 | 70 | 20 | C | 0 | C |
| 330 | | 1.12 | 20 | 60 | 80 | 80 | 70 | 80 | 20 | C | C | C |
| 331 | | 1.12 | 0 | 30 | 40 | 70 | 20 | 70 | 50 | 80 | 70 | 80 |
| 332 | | 1.12 | 0 | 60 | 80 | 70 | 60 | 80 | 0 | 80 | 70 | 90 |
| 333 | | 1.12 | 0 | 70 | 90 | C | 70 | 90 | 40 | C | C | 90 |
| 334 | | 1.12 | 0 | 60 | 70 | 80 | 80 | 40 | 40 | 70 | 80 | C |
| 335 | | 1.12 | 0 | 0 | 0 | 0 | 0 | C | C | C | 90 | 80 |
| 336 | | 1.12 | 0 | 30 | 60 | 80 | 40 | 90 | 60 | 80 | 80 | 90 |
| 337 | | 1.12 | 10 | 0 | 30 | 20 | 70 | C | 70 | C | 80 | 80 |
| 338 | | 1.12 | 20 | 20 | 20 | 20 | 70 | C | 50 | 80 | 80 | 70 |
| 339 | | 1.12 | 30 | 10 | 0 | 0 | 10 | 80 | 90 | C | 90 | 90 |
| 340 | | 1.12 | 20 | 80 | 70 | 40 | 80 | C | C | C | C | 90 |
| 341 | @ | 1.12 | 20 | C | 90 | 90 | 70 | 90 | 90 | C | C | C |
| 342 | | 1.12 | 30 | C | C | C | 90 | C | 80 | C | C | C |

TABLE 7-continued

PREEMERGENCE TESTS % PLANT INHIBITION

| Cpd. No. | | Rate kg/ha | Yens | Anbg | Sejg | Dobr | Bygr | Mogl | Cobu | Vele | Inmu | Wibw |
|---|---|---|---|---|---|---|---|---|---|---|---|---|
| 343 | | 11.21 | 0 | 0 | 0 | 20 | 0 | 20 | 0 | 50 | 30 | 80 |
| 344 | | 1.12 | 0 | 0 | 0 | 0 | 0 | 0 | 0 | 60 | 0 | 0 |
| 345 | | 1.12 | 0 | 0 | 20 | 20 | 30 | 20 | 0 | 70 | 50 | 70 |
| 346 | | 11.21 | 30 | 0 | 0 | 0 | 0 | 80 | 30 | C | C | 60 |
| 347 | | 11.21 | 0 | 80 | 70 | 70 | 80 | 80 | 30 | C | 90 | 80 |
| 348 | | 1.12 | 40 | 60 | 40 | 20 | 80 | C | C | C | C | 70 |
| 349 | | 1.12 | 0 | 20 | 60 | 30 | 70 | 30 | 20 | 80 | 70 | 80 |
| 352 | | 11.21 | 20 | 30 | 50 | 40 | 30 | 80 | 60 | 90 | 60 | 80 |
| 353 | | 11.21 | 0 | 80 | 70 | 20 | 50 | 80 | 80 | C | C | C |
| 354 | | 1.12 | 0 | 20 | 70 | 30 | 60 | 20 | 20 | 90 | 30 | C |
| 355 | | 11.21 | 0 | 0 | 30 | 0 | 20 | 0 | 30 | 80 | 30 | 90 |
| 356 | | 11.21 | 30 | C | C | 80 | 90 | C | 40 | C | C | C |
| 357 | | 11.21 | 20 | 30 | 80 | 40 | 70 | 80 | 20 | 60 | 90 | 70 |
| 358 | | 11.21 | 70 | 60 | 50 | 30 | 80 | C | 80 | C | C | 70 |
| 359 | | 1.12 | 20 | 0 | 20 | 0 | 40 | 40 | 30 | 90 | 90 | C |
| 360 | | 11.21 | 0 | 0 | 0 | 0 | 0 | 0 | 0 | 0 | 0 | 0 |
| 361 | | 11.21 | 0 | 0 | 40 | 60 | 80 | 50 | 0 | 90 | 50 | 80 |
| 362 | | 11.21 | 0 | 50 | 80 | 60 | 50 | 80 | 20 | 90 | 60 | C |
| 363 | | 11.21 | 0 | 0 | 40 | 20 | 0 | 0 | 0 | 50 | 0 | 60 |
| 364 | | 11.21 | 0 | 30 | 80 | 80 | 80 | 70 | 20 | C | 60 | 90 |
| 365 | | 11.21 | 30 | 70 | C | C | C | 90 | 30 | C | 70 | 90 |
| 366 | | 11.21 | 20 | C | C | C | C | 50 | 50 | C | 70 | C |
| 367 | | 11.21 | 0 | 0 | 0 | 0 | 0 | 0 | 0 | 0 | 0 | 0 |
| 368 | | 11.21 | 0 | 0 | 0 | 0 | 0 | 0 | 0 | 30 | 0 | 0 |
| 369 | | 11.21 | 0 | 0 | 0 | 0 | 0 | 30 | 0 | 80 | 30 | 80 |
| 370 | | 11.21 | 0 | 0 | 20 | 0 | 0 | 20 | 0 | 30 | 30 | 80 |
| 371 | | 11.21 | 0 | 0 | 0 | 0 | 0 | 0 | 0 | 0 | 0 | 0 |
| 372 | | 11.21 | 0 | 0 | 0 | 0 | 0 | 0 | 0 | 40 | 10 | 0 |
| 373 | | 11.21 | 0 | 0 | 0 | 0 | 0 | 0 | 0 | 0 | 0 | 20 |
| 374 | | 11.21 | 0 | 0 | 30 | 0 | 0 | 0 | 0 | 80 | 30 | 90 |
| 375 | | 11.21 | 0 | 0 | 0 | 0 | 0 | 0 | 0 | 0 | 0 | 0 |
| 376 | | 11.21 | 0 | 0 | 20 | 0 | 0 | 20 | 0 | 70 | 80 | 30 |
| 377 | | 11.21 | 0 | 0 | 60 | 20 | 40 | 20 | 0 | 90 | 80 | 20 |
| 378 | | 11.21 | 0 | 20 | 50 | 0 | 80 | 70 | 0 | 50 | 80 | 30 |
| 379 | | 11.21 | 0 | 0 | 0 | 0 | 0 | 0 | 0 | 30 | 0 | 50 |
| 380 | | 11.21 | 0 | 0 | 0 | 0 | 0 | 20 | 0 | 30 | 0 | 0 |
| 381 | | 1.12 | 0 | 0 | 20 | 0 | 0 | 0 | 0 | 0 | 0 | 0 |
| 382 | | 11.21 | 0 | 0 | 0 | 0 | 0 | 40 | 0 | 70 | 0 | 80 |
| 383 | | 11.21 | 10 | 10 | 0 | 20 | 10 | 50 | 10 | 70 | 70 | 40 |
| | | 11.21 | 0 | 0 | 0 | 0 | 0 | 40 | 0 | 60 | 60 | 20 |
| 384 | | 11.21 | 0 | 0 | 0 | 0 | 20 | 0 | 0 | 0 | 30 | 0 |
| 385 | | 11.21 | 0 | 0 | 0 | 0 | 30 | 0 | 0 | 20 | 0 | 0 |
| 386 | | 11.21 | 0 | 0 | 0 | 0 | 40 | 20 | 0 | 80 | 80 | 40 |
| 387 | | 11.21 | 0 | 0 | 0 | 0 | 0 | 0 | 0 | 0 | 0 | 0 |
| 388 | | 11.21 | 0 | 30 | 0 | 0 | 0 | 30 | 10 | 80 | 50 | 80 |
| 389 | | 11.21 | 30 | C | C | C | C | C | 70 | C | C | C |
| 390 | | 11.21 | 20 | C | C | C | C | C | 80 | C | C | C |
| 391 | | 1.12 | 20 | C | C | 80 | C | 70 | 50 | C | C | C |
| 392 | | 1.12 | 30 | C | C | C | C | C | 60 | C | C | C |
| 393 | | 1.12 | 0 | 0 | 20 | 0 | 20 | 80 | 0 | 80 | 20 | 40 |
| 394 | | 1.12 | 10 | 30 | 80 | 90 | 60 | 50 | 40 | 90 | C | C |
| 395 | | 1.12 | 10 | 30 | 80 | C | 50 | 30 | 40 | 70 | 80 | C |
| 396 | | 11.21 | 30 | C | C | 90 | 90 | C | 70 | C | C | C |
| 397 | | 1.12 | 20 | 20 | 80 | 90 | 90 | 50 | 20 | 80 | 80 | 90 |
| 398 | | 1.12 | 0 | 0 | 0 | 0 | 0 | 0 | 0 | 0 | 0 | 0 |
| 399 | | 1.12 | 0 | 0 | 30 | 0 | 80 | 40 | 20 | 70 | C | 90 |
| 400 | | 11.21 | 80 | 30 | 30 | 20 | 60 | 0 | 0 | 90 | 80 | 90 |
| 401 | | 1.12 | 30 | 60 | 80 | 40 | 30 | 40 | 20 | 80 | 80 | C |
| 402 | | 1.12 | 0 | 30 | 60 | 80 | 30 | 0 | 0 | 40 | 50 | 80 |
| 403 | | 11.21 | 20 | 40 | 90 | 90 | 80 | 70 | 80 | 80 | 70 | C |
| 404 | | 11.21 | 30 | 60 | 90 | C | 70 | 80 | 30 | 90 | 90 | C |
| 405 | | 11.21 | 30 | 50 | 90 | 50 | 80 | 70 | 60 | C | 80 | C |
| 406 | | 11.21 | 20 | 30 | 90 | 40 | C | 80 | 60 | C | C | 90 |
| 407 | | 11.21 | 40 | 20 | 20 | 20 | 40 | C | C | C | 80 | 80 |
| 408 | @ | 11.21 | 20 | 80 | 70 | 20 | 30 | 70 | 40 | C | 80 | C |
| 409 | + | 11.21 | 0 | 0 | 40 | 20 | 20 | 40 | 20 | 50 | N | N |
| 410 | + | 11.21 | 0 | 30 | 60 | 40 | 60 | 40 | 30 | 60 | 70 | 30 |
| 411 | | 1.12 | 0 | 90 | C | C | 80 | 80 | 40 | 90 | C | C |
| 412 | | 1.12 | 0 | 20 | 40 | 30 | 50 | 70 | 40 | 60 | 50 | 80 |
| 413 | | 11.21 | 0 | 20 | 60 | 50 | 40 | 40 | 20 | 70 | 40 | 90 |
| 414 | | 11.21 | 20 | C | 90 | 60 | 60 | C | 20 | C | C | C |
| 415 | | 1.12 | 0 | 30 | 80 | 30 | 80 | 40 | 20 | 90 | 90 | 70 |
| 416 | | 1.12 | 10 | 70 | 80 | 20 | 80 | 30 | 60 | 80 | C | 30 |
| 417 | | 1.12 | 20 | 0 | 30 | 0 | 0 | 20 | 0 | 60 | 40 | 30 |

TABLE 7-continued

PREEMERGENCE TESTS % PLANT INHIBITION

| Cpd. No. | | Rate kg/ha | Yens | Anbg | Sejg | Dobr | Bygr | Mogl | Cobu | Vele | Inmu | Wibw |
|---|---|---|---|---|---|---|---|---|---|---|---|---|
| 418 | | 1.12 | 20 | 20 | 70 | 40 | 70 | 30 | 70 | 80 | 60 | 50 |
| 419 | | 1.12 | 0 | 20 | 30 | 30 | 10 | 70 | 20 | 80 | 60 | 80 |
| 420 | | 1.12 | 0 | 20 | 80 | 80 | 70 | 20 | 20 | 60 | 50 | C |
| 421 | | 11.21 | 0 | 80 | 90 | C | 40 | C | 80 | C | 90 | C |
| 422 | | 11.21 | 0 | 70 | 90 | C | 70 | 70 | 40 | C | 70 | C |
| 423 | | 11.21 | 0 | 0 | 0 | 0 | 0 | 0 | 0 | 50 | 20 | 20 |
| 424 | | 11.21 | 0 | 0 | 40 | 20 | 0 | 0 | 0 | 40 | 0 | 30 |
| 425 | | 11.21 | 0 | 0 | 70 | 20 | 20 | C | 40 | C | C | 30 |
| 426 | | 11.21 | 0 | 0 | 50 | 10 | 50 | 40 | 0 | 70 | 60 | 70 |
| 427 | ( | 11.21 | 0 | 0 | 0 | 0 | 0 | 0 | 0 | 0 | 10 | 0 |
| 428 | | 11.21 | 0 | 0 | 0 | 0 | 20 | 30 | 0 | 90 | 70 | 70 |
| 429 | | 11.21 | 0 | 30 | 30 | 10 | 20 | 0 | 0 | 30 | 50 | 10 |
| 430 | | 11.21 | 20 | 0 | 30 | 0 | 0 | 70 | 40 | 60 | 30 | 20 |
| 431 | | 11.21 | 0 | 0 | 0 | 0 | 0 | 0 | 0 | 60 | 20 | 0 |
| 432 | | 11.21 | 0 | 20 | 50 | 70 | 10 | 20 | 10 | C | 10 | 90 |
| 433 | | 11.21 | 0 | 0 | 0 | 0 | 0 | 0 | 0 | 0 | 0 | 0 |
| 435 | | 11.21 | 0 | 40 | 60 | 30 | 70 | C | 20 | C | 90 | 90 |
| | + | 11.21 | N | N | N | 0 | 0 | 0 | 0 | 0 | 0 | 0 |
| 436 | + | 11.21 | N | N | N | 0 | 0 | 0 | 0 | 0 | 0 | 0 |
| | | 11.21 | 20 | 0 | 0 | 0 | 0 | 30 | 0 | 40 | 20 | 10 |
| 437 | + | 11.21 | 0 | 0 | 0 | 0 | 40 | 80 | 30 | 80 | 80 | 60 |
| 438 | | 1.12 | 0 | 30 | 60 | 40 | 30 | 70 | 50 | 80 | 80 | 40 |
| 439 | | 1.12 | 0 | 0 | 0 | 0 | 0 | 80 | 50 | 50 | 60 | 40 |
| 440 | | 11.21 | 0 | 30 | 50 | 70 | 40 | 50 | 20 | 60 | 40 | C |
| 441 | | 1.12 | 0 | 40 | 40 | 20 | 80 | 90 | 20 | C | C | 70 |
| 442 | | 11.21 | 10 | 60 | 80 | 70 | C | 80 | 20 | C | C | C |
| 443 | | 1.12 | 0 | 80 | 10 | 50 | 40 | 90 | 80 | C | 90 | C |
| 444 | | 1.12 | 0 | 30 | 80 | 20 | 30 | 0 | 0 | 0 | N | N |
| 445 | | 1.12 | 10 | C | 80 | C | 80 | C | C | C | C | C |
| 446 | | 1.12 | 60 | C | 80 | 90 | 80 | C | C | 90 | C | C |
| 447 | | 1.12 | 30 | C | 40 | 80 | 90 | C | C | C | C | C |
| 448 | | 1.12 | 80 | C | 90 | 80 | C | C | C | C | C | C |
| 449 | ( | 1.12 | 0 | 60 | 80 | 50 | 60 | 30 | 30 | 70 | 10 | 30 |
| 450 | | 1.12 | 0 | 0 | 10 | 0 | 20 | 80 | 20 | 90 | 10 | 40 |
| 451 | | 1.12 | 20 | 0 | 20 | 20 | 30 | C | 70 | 80 | 50 | 70 |
| 452 | | 1.12 | 80 | C | 90 | 70 | C | C | C | C | C | C |
| 453 | | 1.12 | 0 | 0 | 0 | 0 | 0 | 90 | 20 | C | 30 | 80 |
| 454 | ( | 1.12 | 0 | C | 80 | 80 | 80 | 90 | 80 | C | C | C |
| 455 | | 1.12 | 40 | C | 90 | C | 90 | C | C | C | C | C |
| 456 | | 1.12 | 40 | C | 80 | C | 80 | C | C | C | C | C |
| 457 | | 1.12 | 0 | C | 70 | 40 | 60 | C | 40 | 90 | 90 | C |
| 458 | ( | 1.12 | 50 | C | 90 | C | 90 | C | C | C | C | C |
| 459 | | 1.12 | 10 | C | 60 | 70 | 90 | C | 70 | C | C | C |
| 460 | ( | 1.12 | 20 | C | 90 | C | 90 | C | 70 | C | C | C |
| 461 | | 1.12 | 60 | C | 90 | C | 90 | C | 30 | C | C | C |
| 462 | | 11.21 | 0 | 0 | 0 | 0 | 60 | 80 | 50 | 90 | C | C |
| 463 | | 1.12 | 50 | 30 | 70 | 50 | 80 | C | 80 | C | C | C |
| 464 | | 1.12 | 0 | C | 70 | 80 | 70 | 90 | 30 | C | C | C |
| 465 | | 11.21 | 20 | C | C | C | C | C | C | C | C | C |
| 466 | | 11.21 | 70 | 0 | 0 | 10 | 0 | 90 | 50 | C | 80 | C |
| 467 | | 11.21 | 10 | 20 | 10 | 10 | 80 | 0 | 10 | C | C | 80 |
| 468 | | 1.12 | 0 | 90 | 50 | 90 | 60 | 80 | 70 | 90 | C | C |
| 469 | | 1.12 | 20 | 20 | 20 | 10 | 80 | 70 | 20 | C | C | C |
| | | 1.12 | 20 | 40 | 0 | 0 | 40 | 80 | 10 | C | C | C |
| 470 | | 1.12 | 0 | 0 | 0 | 0 | 0 | 20 | 40 | 20 | 0 | 0 |
| 471 | | 11.21 | 20 | 90 | 80 | 80 | 20 | 30 | 30 | 90 | 80 | C |
| 472 | | 11.21 | 0 | 0 | 0 | 0 | 20 | 20 | 10 | 90 | 70 | 50 |
| 473 | | 11.21 | 0 | 0 | 0 | 0 | 0 | 0 | 0 | 10 | N | 30 |
| 474 | | 11.21 | 0 | 80 | C | C | 90 | C | 70 | C | 90 | C |
| 475 | | 11.21 | 20 | 70 | 60 | 30 | 80 | C | 40 | C | C | C |
| 476 | | 11.21 | 0 | 0 | 0 | 0 | 0 | 0 | 0 | 0 | 0 | 0 |
| 477 | | 11.21 | 0 | 30 | 0 | 0 | 0 | 0 | 0 | 0 | 0 | 0 |
| 478 | | 11.21 | 30 | 80 | 70 | 40 | C | C | C | C | C | C |
| 479 | | 11.21 | 0 | 0 | 0 | 0 | 0 | 0 | 0 | 0 | 0 | 0 |
| 480 | | 11.21 | 0 | 0 | 0 | 0 | 0 | 0 | 0 | 0 | 0 | 0 |
| 481 | | 11.21 | 0 | 40 | 30 | 60 | 20 | 30 | 0 | 70 | 60 | 90 |
| 482 | | 11.21 | 30 | 80 | 60 | C | 80 | C | 80 | C | C | C |
| 484 | @ | 5.61 | 0 | 0 | 20 | 0 | 0 | 20 | 0 | 60 | 20 | 20 |
| 485 | | 11.21 | 0 | 20 | 30 | 30 | 0 | 0 | 0 | 30 | 30 | 70 |
| 486 | | 1.12 | 0 | 70 | 60 | 80 | 80 | 90 | 20 | 80 | C | 80 |
| 487 | | 11.21 | 0 | 0 | 0 | 0 | 0 | 50 | 0 | 40 | 20 | 0 |
| 489 | | 11.21 | 0 | 90 | 80 | C | 30 | 10 | 0 | 10 | 0 | 10 |
| | | 1.12 | 0 | 0 | 0 | 0 | 0 | 0 | 0 | 0 | 0 | 0 |
| 490 | | 1.12 | 0 | 60 | 50 | 60 | 60 | 70 | 40 | C | 80 | 90 |

TABLE 7-continued

PREEMERGENCE TESTS % PLANT INHIBITION

| Cpd. No. | Rate kg/ha | Yens | Anbg | Sejg | Dobr | Bygr | Mogl | Cobu | Vele | Inmu | Wibw |
|---|---|---|---|---|---|---|---|---|---|---|---|
| 491 | 11.21 | 0 | 0 | 0 | 0 | 0 | 0 | 0 | 0 | 0 | 0 |
| 492 | 11.21 | 0 | 0 | 0 | 0 | 0 | 0 | 0 | 0 | 0 | 0 |
| 493 | 11.21 | 20 | 0 | 0 | 0 | 0 | 0 | 0 | 10 | 20 | 0 |
| 494 | 11.21 | 0 | 0 | 0 | 0 | 0 | 0 | 0 | 10 | 20 | 10 |
| 495 | 1.12 | 0 | 0 | 0 | 0 | 0 | 10 | 0 | 10 | 0 | 0 |
| 496 | 1.12 | 0 | 0 | 0 | 0 | 0 | 0 | 0 | 0 | 0 | 0 |
| 497 | 11.21 | 0 | 0 | 0 | 0 | 0 | 20 | 0 | 0 | 0 | 0 |
| 498 | 11.21 | 0 | 0 | 0 | 0 | 80 | 50 | 10 | C | 70 | 90 |
| 499 | 11.21 | 0 | 0 | 0 | 0 | 0 | 0 | 0 | 0 | 0 | 0 |
| 501 | 11.21 | 20 | 90 | 60 | 90 | 90 | 80 | 20 | C | 90 | 40 |
|  | 1.12 | 0 | 0 | 0 | 0 | 0 | 0 | 0 | 30 | 20 | 20 |

*Poor germination-Wibw.
@cocklebur germination eratic
+Excessive damping off
(Sejg germination was thin.
)FREQUENT DAMPING OFF-Inmu, Wibw

TABLE 7A

PREEMERGENCE TESTS % PLANT INHIBITION

| Cpd. No. | Rate kg/ha | Yens | Anbg | Sejg | Dobr | Bygr | Mogl | Cobu | Vele | Inmu | Wibw |
|---|---|---|---|---|---|---|---|---|---|---|---|
| 89 | 11.21 | 10 | 0 | 0 | 0 | 0 | 20 | 0 | 90 | 70 | 30 |
| 93 | 1.12 | 0 | 0 | 0 | 0 | 0 | 30 | 20 | 20 | 10 | 20 |
| 98 | 1.12 | 0 | 0 | 70 | 60 | 30 | 80 | 20 | 90 | 70 | 60 |
| 136 | 1.12 | 0 | 90 | 90 | C | 70 | 80 | 90 | 90 | 90 | C |
| 139 | 1.12 | 20 | 20 | 40 | 80 | 30 | 70 | 70 | C | 90 | 90 |
| 140 | 1.12 | 0 | 30 | 70 | 60 | 0 | 70 | 80 | 90 | 70 | 70 |
| 141 | 1.12 | 0 | 20 | 50 | 70 | 20 | 80 | 70 | 70 | 80 | 90 |
| 178 | 1.12 | 0 | 20 | 10 | 30 | 10 | 50 | 20 | C | 90 | C |
| 198 | 1.12 | 0 | 0 | 0 | 0 | 0 | 0 | 0 | 80 | 20 | 70 |
| 203 | 11.21 | 0 | 0 | 20 | 10 | 0 | 10 | 20 | 0 | 0 | 0 |
| 205 | 11.21 | 0 | 0 | 20 | 0 | 0 | 0 | 0 | 10 | 30 | 10 |
| 251 | 1.12 | 0 | 50 | 70 | 80 | 0 | 40 | 30 | 60 | 20 | 90 |
| 252 | 1.12 | 0 | 30 | 60 | 60 | 20 | 40 | 30 | 20 | 10 | 10 |
| 285 | 1.12 | 0 | 0 | 0 | 0 | 50 | C | 80 | C | 10 | 80 |
| 287 | 1.12 | 30 | 0 | 0 | 0 | 0 | 70 | 90 | C | 60 | 80 |
| 288 | 1.12 | 0 | 0 | 0 | 0 | 0 | C | 30 | C | 20 | 90 |
| 303 | 11.21 | 0 | C | C | C | C | C | C | C | C | C |
| 315 | 11.21 | 20 | C | C | C | C | C | C | C | C | C |
| 329 | 1.12 | 0 | 0 | 0 | 0 | 0 | 70 | 0 | C | 90 | C |
| 350 | 1.12 | 0 | 0 | 0 | 0 | 0 | 80 | 10 | C | C | 50 |
| 351 | 1.12 | 0 | 0 | 0 | 0 | 0 | 80 | 80 | C | C | C |
| 488 | 1.12 | 0 | 30 | 40 | 80 | 70 | 70 | 0 | C | 60 | C |
| 500 | 11.21 | 0 | 10 | 70 | 80 | 30 | 60 | 40 | 70 | 30 | 90 |

POST-EMERGENCE HERBICIDE TESTS

The post-emergence herbicidal activity of some of the various compounds of this invention was demonstrated by greenhouse testing in the following manner. Topsoil is placed in aluminum pans having holes in the bottom and compacted to a depth of 0.95 to 1.27 cm from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a bench in the greenhouse and watered from below as needed. After the plants reach the desired age (two to three weeks), each pan, is removed individually to a spraying chamber and sprayed by means of an atomizer, operating at a spray pressure of 170.3 kPa (10 psig) at the application rates noted. In the spray solution is an amount of an emulsifying agent mixture to give a spray solution or suspension which contains about 0.4% by volume of the emulsifier. The spray solution or suspension contains a sufficient amount of the candidate chemical in order to give application rates of the active ingredient corresponding to those shown in Tables 8 and 8A, while applying a total amount of solution or suspension equivalent to 1870 L/Ha (200 gallons/acre). The pans were returned to the greenhouse and watered as before and the injury to the plants as compared to the control is observed at approximately 10–14 days (usually 11 days) and in some instances observed again at 24–28 days (usually 25 days) after spraying. The post-emergent herbicidal activity shown in these tables is the percent inhibition of each plant species.

TABLE 8

POST EMERGENCE TESTS % PLANT INHIBITION

| Cpd. No. | Rate kg/ha | Yens | Anbg | Sejg | Dobr | Bygr | Mogl | Cobu | Vele | Inmu | Wibw |
|---|---|---|---|---|---|---|---|---|---|---|---|
| 62 | 11.21 | 0 | 0 | 0 | 0 | 0 | 0 | 0 | 10 | 0 | 0 |
| 63 | 11.21 | 0 | 20 | 70 | 20 | 20 | C | 0 | C | 40 | C |
| 64 | 11.21 | 0 | 20 | 20 | 0 | 30 | 60 | 20 | 60 | 20 | 80 |
| 65 | 11.21 | 0 | 0 | 50 | 10 | 70 | 50 | 40 | 70 | 30 | 70 |
| 66 | 11.21 | 0 | 0 | 80 | 30 | 20 | 70 | 0 | 50 | 30 | C |
| 67 | 11.21 | 20 | 20 | 80 | 40 | 40 | 70 | 20 | 80 | 40 | C |
| 68 | 11.21 | 0 | 0 | 0 | 0 | 0 | 0 | 0 | 0 | 0 | 0 |
| 69 | 11.21 | 0 | 0 | 0 | 0 | 0 | 10 | 0 | 10 | 0 | 0 |
| 70 | 11.21 | 0 | 10 | 10 | 10 | 40 | 40 | 30 | 50 | 20 | N |
| 71 | 11.21 | 0 | 0 | 0 | 0 | 0 | 20 | 30 | 20 | 20 | 40 |
| 72 | 11.21 | 10 | 10 | 10 | 20 | 50 | 30 | 60 | 90 | 30 | 90 |
| 73 | 11.21 | 0 | 0 | 0 | 0 | 0 | 0 | 10 | 20 | 20 | 20 |
| 74 | 1.12 | 10 | 0 | 10 | 10 | 10 | 20 | 20 | 40 | 40 | 90 |
| 75 | 11.21 | 0 | 0 | 0 | 0 | 0 | 10 | 0 | 0 | 0 | 60 |
| 76 | 1.12 | 10 | 40 | 40 | 30 | 50 | 50 | 40 | 90 | 70 | C |
| 77 | 11.21 | 0 | 20 | 20 | 0 | 20 | 10 | 20 | 30 | 60 | 60 |
| 78 | 11.21 | 0 | 0 | 10 | 10 | 0 | 10 | 10 | 40 | 40 | 30 |
| 79 | 11.21 | 10 | 60 | 30 | 20 | 20 | 60 | 20 | C | 90 | C |
| 80 | 11.21 | 0 | 0 | 0 | 0 | 0 | 10 | 10 | 60 | 0 | N |
| 81 | 11.21 | 50 | 0 | 70 | 10 | 70 | 60 | 40 | 80 | 10 | 90 |
| 82 | 11.21 | 10 | 0 | 40 | 20 | 30 | 90 | 0 | 20 | 30 | 60 |
| 83 | 11.21 | 20 | 0 | 60 | 40 | 40 | 80 | 70 | C | 90 | C |
| 84 | 11.21 | 10 | 10 | 40 | 0 | 10 | 50 | 20 | C | 0 | N |
| 85 | 11.21 | 20 | 60 | 90 | 50 | 70 | C | 40 | C | 20 | C |
| 86 | 11.21 | 10 | 30 | 80 | 0 | 80 | C | 70 | C | 60 | C |
| 87 | 11.21 | 10 | 10 | 40 | 0 | 20 | 70 | 50 | C | 30 | 40 |
| 88 | 11.21 | 0 | 10 | 70 | 10 | 50 | C | C | C | 60 | C |
| 90 | 11.21 | 0 | 10 | 0 | 10 | 0 | 60 | 30 | C | 50 | 50 |
| 91 | 1.12 | 10 | 50 | 40 | 40 | 30 | 60 | C | 40 | 50 | 80 |
| 92 | 1.12 | 20 | 30 | 40 | 50 | 30 | C | 80 | C | 80 | 80 |
| 94 | 1.12 | 10 | 90 | 90 | C | C | 90 | 80 | C | 80 | C |
| 95 | 1.12 | 10 | 60 | 50 | 40 | 80 | 80 | C | C | 70 | C |
| 96 | 1.12 | 40 | C | C | C | C | C | 90 | C | C | C |
| 97 | 1.12 | 50 | 70 | 60 | 90 | C | 90 | C | C | C | C |
| 99 | 11.21 | 10 | C | C | 90 | C | C | 90 | C | C | C |
| 100 | 1.12 | 20 | C | C | C | C | C | 80 | C | 80 | C |
| 101 | 1.12 | 30 | 90 | 70 | C | C | C | C | C | C | C |
| 102 | 1.12 | 20 | 90 | C | C | 90 | C | 60 | C | C | C |
| 103 | 1.12 | 10 | 40 | 70 | 30 | 80 | 80 | 60 | C | 70 | C |
| 104 | 1.12 | 20 | 30 | 80 | 40 | 50 | C | 70 | C | 40 | C |
| 105 | 1.12 | 20 | 30 | 20 | 0 | 20 | 40 | 20 | 80 | 30 | C |
| 106 | 1.12 | 10 | 30 | 40 | 20 | 60 | C | 60 | C | 60 | 90 |
| 107 | 1.12 | 10 | 0 | 20 | 0 | 30 | 50 | 50 | 90 | 40 | 90 |
| 108 | 11.21 | 0 | 90 | 90 | C | C | C | C | C | C | C |
| 109 | 1.12 | 10 | 40 | 20 | 0 | 30 | 60 | 40 | C | 40 | 90 |
| 110 | 1.12 | 20 | 30 | 40 | 20 | 70 | 80 | 60 | C | 30 | C |
| 111 | 11.21 | 30 | 0 | 20 | 20 | 60 | C | C | C | 80 | C |
| 112 | 11.21 | 40 | 30 | 30 | 0 | 60 | 80 | 60 | C | 40 | 70 |
| 113 | 11.21 | 0 | 0 | 0 | 0 | 0 | 30 | 20 | 50 | 0 | 20 |
| 114 | 11.21 | 10 | 10 | 0 | 0 | 0 | 50 | 20 | 50 | 10 | 60 |
| 115 | 1.12 | 20 | 40 | 40 | 20 | 80 | 60 | 60 | C | 60 | C |
| 116 | 1.12 | 20 | 80 | 70 | 70 | 80 | C | C | C | 80 | 80 |
| 117 | 1.12 | 20 | 90 | C | C | C | C | 90 | C | 90 | C |
| 118 | 1.12 | 30 | 30 | 30 | 20 | 30 | 60 | 80 | 90 | 30 | C |
| 119 | 11.21 | 20 | C | C | C | C | C | C | C | C | C |
| 120 | 1.12 | 10 | 40 | 80 | 50 | 80 | C | 90 | C | 70 | C |
| 121 | 11.21 | 20 | 40 | 90 | 90 | C | C | 90 | C | 90 | C |
| 122 | 1.12 | 20 | 20 | 70 | 20 | 70 | 80 | 60 | C | 50 | 90 |
| 123 | 1.12 | 20 | 0 | 50 | 60 | 50 | C | 70 | C | 30 | 90 |
| 124 | 11.21 | 20 | 70 | C | 50 | 90 | C | 70 | C | 90 | C |
| 125 | 1.12 | 0 | 20 | 0 | 0 | 0 | 30 | 40 | C | 30 | C |
| 126 | 1.12 | 10 | 40 | 30 | 0 | 50 | 60 | 30 | 90 | 40 | 80 |
| 127 | 1.12 | 20 | 20 | C | 80 | 60 | C | C | C | C | C |
| 128 | 1.12 | 20 | 30 | C | C | 50 | C | C | C | 90 | C |
| 129 | 1.12 | 30 | 40 | 90 | 80 | 80 | 90 | C | C | 90 | C |
| 130 | 1.12 | 20 | 20 | 70 | 30 | 40 | C | C | C | 40 | C |
| 131 | 1.12 | 30 | 20 | 50 | 20 | 0 | C | C | C | 40 | C |
| 132 | 11.21 | 30 | 60 | C | 80 | C | C | C | C | C | C |
| 133 | 1.12 | 40 | 0 | 50 | 20 | 50 | C | C | C | 40 | 80 |
| 134 | 1.12 | 20 | C | C | C | C | C | C | C | C | C |
| 135 | 1.12 | 20 | C | C | C | C | C | C | C | C | C |
| 137 | 1.12 | 20 | C | C | C | C | C | C | C | C | C |
| 138 | 1.12 | 20 | C | C | C | C | C | C | C | C | C |
| 142 | 1.12 | 30 | C | C | C | C | C | C | C | C | C |

TABLE 8-continued

POST EMERGENCE TESTS % PLANT INHIBITION

| Cpd. No. | Rate kg/ha | Yens | Anbg | Sejg | Dobr | Bygr | Mogl | Cobu | Vele | Inmu | Wibw |
|---|---|---|---|---|---|---|---|---|---|---|---|
| 143 | 1.12 | 20 | C | 0 | C | C | C | C | C | C | C |
| 144 | 1.12 | 20 | 60 | 90 | C | 70 | C | C | C | C | C |
| 145 | 1.12 | 20 | 80 | 80 | C | 70 | 80 | C | C | C | C |
| 146 | 1.12 | 30 | 80 | 80 | 40 | 90 | C | C | C | 90 | C |
| 147 | 1.12 | 30 | 0 | 70 | 0 | 80 | C | C | C | 40 | C |
| 148 | 1.12 | 20 | C | C | C | C | C | C | C | C | C |
| 149 | 1.12 | 20 | 0 | 40 | 0 | 30 | C | 70 | C | 50 | C |
| 150 | 1.12 | 20 | C | C | C | C | C | C | C | 90 | C |
| 151 | 1.12 | 20 | C | C | C | C | C | C | C | 80 | C |
| 152 | 1.12 | 20 | 30 | 20 | 40 | 0 | 50 | 40 | 60 | 50 | 90 |
| 153 | 1.12 | 10 | 40 | 90 | 40 | 30 | C | 40 | C | 50 | 90 |
| 154 | 1.12 | 20 | 20 | 70 | 40 | 80 | C | 80 | C | 40 | 80 |
| 155 | 1.12 | 20 | 30 | 80 | 90 | 80 | C | 40 | C | 50 | 80 |
| 156 | 1.12 | 10 | 30 | 70 | 60 | 30 | C | 80 | C | 30 | 80 |
| 157 | 1.12 | 20 | 50 | 80 | 40 | 60 | 80 | 50 | C | 70 | C |
| 158 | 1.12 | 20 | 50 | 80 | 60 | 50 | C | 80 | C | 20 | 90 |
| 159 | 11.21 | 50 | 50 | C | C | C | C | C | C | 80 | C |
| 160 | 1.12 | 30 | 70 | 80 | 60 | 80 | C | C | C | 80 | C |
| 161 | 11.21 | 20 | C | C | C | C | C | C | C | C | C |
| 162 | 1.12 | 10 | 10 | 40 | 30 | 20 | 50 | 20 | 30 | 10 | 90 |
| 163 | 11.21 | 30 | 60 | 50 | 30 | 60 | C | 30 | C | 30 | C |
| 164 | 11.21 | 0 | 0 | 0 | 0 | 0 | 20 | 40 | 20 | 40 | 30 |
|  | 11.21 | 0 | 30 | 30 | 0 | 20 | 20 | 40 | 30 | 60 | 20 |
| 165 | 11.21 | 10 | 80 | 80 | 80 | 80 | C | 40 | C | 20 | C |
| 166 | 1.12 | 0 | 20 | 30 | 0 | 0 | 20 | 20 | 60 | 30 | 90 |
| 167 | 11.21 | 0 | 60 | C | 60 | 90 | 90 | 90 | C | C | C |
|  | 11.21 | 20 | 60 | 80 | 50 | 80 | 80 | 70 | C | 90 | C |
| 168 | 11.21 | 40 | 20 | 80 | 20 | 70 | 80 | C | C | 60 | C |
| 169 | 1.12 | 30 | 30 | 80 | 30 | 50 | 90 | 70 | 90 | 50 | C |
| 170 | 11.21 | 20 | 50 | 80 | 40 | 70 | 90 | 70 | 90 | 70 | C |
|  | 11.21 | 0 | 40 | 80 | 20 | 80 | 90 | 80 | C | 90 | C |
| 171 | 11.21 | 0 | 10 | 50 | 30 | 50 | 20 | 40 | C | 30 | C |
| 172 | 1.12 | 20 | 0 | 40 | 20 | 30 | 50 | 60 | 80 | 30 | 30 |
| 173 | 1.12 | 20 | 0 | 40 | 20 | 20 | 70 | 80 | 70 | 30 | 60 |
| 174 | 1.12 | 20 | 0 | 40 | 20 | 30 | 60 | 70 | 80 | 30 | 80 |
| 175 | 11.21 | 20 | 40 | 90 | 90 | 90 | C | 60 | C | 60 | C |
| 176 | 11.21 | 20 | 90 | 90 | 80 | 90 | C | 90 | C | 90 | C |
| 177 | 11.21 | 10 | 60 | C | C | C | C | C | C | C | C |
| 179 | 1.12 | 30 | 80 | 90 | 60 | 80 | C | 70 | C | 80 | C |
| 180 | 1.12 | 30 | 40 | 90 | 70 | C | 90 | 80 | C | C | C |
| 181 | 11.21 | 40 | 50 | C | 80 | C | 90 | C | C | C | C |
| 182 | 11.21 | 20 | C | C | C | C | C | C | C | C | C |
| 183 | 1.12 | 0 | 40 | 80 | 50 | 60 | 80 | 80 | 90 | 50 | C |
| 184 | 11.21 | 30 | 20 | 60 | 20 | 70 | C | C | C | 60 | C |
| 185 | 11.21 | 20 | 30 | 80 | 30 | 70 | 90 | 90 | C | 80 | C |
| 186 | 1.12 | 30 | 80 | 80 | 90 | 80 | C | 80 | C | 80 | C |
| 187 | 1.12 | 0 | 40 | 70 | 30 | 40 | 40 | 70 | 80 | 30 | 90 |
| 188 | 11.21 | 30 | 80 | C | C | 90 | 90 | C | C | 80 | C |
| 189 | 1.12 | 30 | 20 | 60 | 20 | 40 | 50 | 40 | 80 | 40 | 80 |
| 190 | 1.12 | 20 | 0 | 50 | 20 | 30 | C | 90 | C | 50 | 50 |
| 191 | 11.21 | 10 | 30 | C | 20 | 60 | C | 40 | 90 | 90 | C |
| 192 | 11.21 | 30 | C | C | C | C | C | C | C | C | C |
| 193 | 11.21 | 0 | 20 | 70 | 60 | 80 | C | C | C | 80 | 90 |
| 194 | 1.12 | 20 | 50 | 70 | 30 | 80 | 90 | 90 | C | 60 | 90 |
| 195 | 1.12 | 30 | 30 | 30 | 40 | 80 | 90 | C | C | 50 | 80 |
| 196 | 1.12 | 30 | 30 | 60 | 40 | 70 | 90 | 90 | C | 60 | 80 |
| 197 | 11.21 | 10 | 50 | 80 | 30 | C | 80 | 90 | C | 90 | C |
| 199 | 1.12 | 30 | 30 | 80 | 30 | 60 | C | 50 | C | 50 | 30 |
| 200 | 1.12 | 20 | 20 | 20 | 30 | 30 | C | 80 | C | 60 | 50 |
| 201 | 1.12 | 0 | 0 | 20 | 20 | 0 | C | 70 | C | 40 | 50 |
| 202 | 1.12 | 20 | 0 | 30 | 20 | 20 | C | 60 | 80 | 30 | 50 |
| 204 | 1.12 | 0 | 0 | 20 | 0 | 0 | 0 | 10 | 20 | 0 | 30 |
| 206 | 11.21 | 0 | 30 | 90 | 50 | 80 | 70 | 40 | C | 60 | C |
| 207 | 1.12 | 0 | 0 | 20 | 0 | 0 | 30 | 30 | 40 | 30 | 20 |
| 208 | 1.12 | 10 | 60 | 90 | 60 | 90 | C | 90 | C | C | C |
| 209 | 1.12 | 10 | 0 | 0 | 0 | 0 | 20 | 20 | 40 | 0 | 40 |
| 210 | 1.12 | 10 | 10 | 10 | 10 | 10 | 90 | 50 | 40 | 20 | 90 |
| 211 | 1.12 | 0 | 20 | 70 | 50 | 70 | 80 | 60 | C | 30 | C |
| 212 | 1.12 | 40 | 90 | 90 | 80 | C | 90 | 90 | C | 90 | 90 |
| 213 | 1.12 | 30 | 20 | 10 | 30 | 40 | 60 | C | 90 | 90 | 90 |
| 214 | 1.12 | 30 | 60 | 60 | 80 | 40 | 60 | 90 | 60 | 90 | 90 |
| 215 | 1.12 | 10 | 30 | 50 | 40 | 80 | C | C | C | C | 90 |
| 216 | 1.12 | 10 | 60 | C | 80 | 80 | 90 | 60 | C | 60 | C |
| 217 | 1.12 | 20 | 90 | 90 | C | 90 | 90 | 90 | C | 90 | C |

TABLE 8-continued

POST EMERGENCE TESTS % PLANT INHIBITION

| Cpd. No. | Rate kg/ha | Yens | Anbg | Sejg | Dobr | Bygr | Mogl | Cobu | Vele | Inmu | Wibw |
|---|---|---|---|---|---|---|---|---|---|---|---|
| 218 | 1.12 | 30 | C | C | C | C | C | 90 | C | 90 | C |
| 219 | 1.12 | 60 | 50 | C | C | C | C | C | C | 90 | 90 |
| 220 | 1.12 | 40 | C | 90 | 90 | C | C | C | C | C | C |
| 221 | 1.12 | 50 | 90 | 90 | C | C | C | 90 | C | C | C |
| 222 | 1.12 | 80 | 0 | 20 | 90 | 90 | 90 | 80 | C | C | 90 |
| 223 | 1.12 | 30 | 90 | 90 | C | C | 90 | C | C | C | C |
| 224 | 1.12 | 40 | 50 | 80 | 60 | 90 | 90 | C | C | 80 | C |
| 225 | 1.12 | 30 | 90 | 90 | 60 | C | C | C | C | 90 | C |
| 226 | 1.12 | 30 | 60 | 70 | C | C | 90 | C | C | C | 90 |
| 227 | 1.12 | 60 | 90 | 90 | C | C | 90 | C | C | 90 | 90 |
| 228 | 1.12 | 80 | 90 | C | C | C | C | C | C | C | C |
| 229 | 1.12 | 40 | 70 | C | 90 | C | C | C | C | C | C |
| 230 | 1.12 | 40 | 30 | 50 | 30 | 90 | C | C | C | 60 | 90 |
| 231 | 1.12 | 20 | 0 | 20 | 20 | 70 | 50 | 50 | 90 | 40 | 80 |
| 232 | 1.12 | 10 | C | C | C | 90 | 90 | C | C | 90 | C |
| 233 | 1.12 | 10 | 60 | 40 | 50 | 90 | 90 | C | 90 | 90 | 90 |
| 234 | 1.12 | 10 | 0 | 10 | 0 | 0 | 50 | 90 | C | 20 | C |
| 235 | 1.12 | 0 | 0 | 0 | 0 | 0 | 50 | 90 | C | 10 | 90 |
| 236 | 1.12 | 10 | 50 | 90 | C | 50 | C | 90 | C | C | 90 |
| 237 | 1.12 | 20 | 40 | 60 | 60 | 90 | 90 | 90 | C | 70 | 90 |
| 238 | 1.12 | 30 | 20 | 60 | 20 | 40 | 80 | 80 | 90 | 40 | C |
| 239 | 1.12 | 80 | 90 | 90 | C | C | C | C | C | C | 90 |
| 240 | 1.12 | 30 | C | C | C | C | C | C | C | C | C |
| 241 | 1.12 | 20 | C | 50 | 90 | C | 60 | 80 | C | 70 | 90 |
| 242 | 1.12 | 30 | 60 | 50 | 90 | C | 90 | 90 | C | C | C |
| 243 | 1.12 | 30 | 60 | 50 | C | C | 90 | 90 | C | 90 | C |
| 244 | 1.12 | 20 | 20 | 20 | 0 | 30 | 50 | 40 | 50 | 50 | 50 |
| 245 | 1.12 | 20 | 30 | 30 | 90 | 50 | 90 | 90 | C | 90 | 90 |
| 246 | 1.12 | 30 | C | C | C | C | C | C | C | C | C |
| 247 | 1.12 | 60 | 40 | 80 | C | C | 90 | 90 | C | C | C |
| 248 | 1.12 | 60 | 40 | 60 | 50 | C | 90 | 90 | 90 | 90 | C |
| 249 | 1.12 | 30 | 90 | 90 | C | C | 80 | 90 | C | C | C |
| 250 | 1.12 | 10 | C | C | C | C | C | 90 | C | C | 90 |
| 253 | 1.12 | 10 | 90 | 90 | 90 | 80 | 80 | 80 | C | 90 | C |
| 254 | 1.12 | 10 | C | C | C | C | C | C | C | C | C |
| 255 | 1.12 | 40 | C | C | C | C | C | C | C | C | C |
| 256 | 1.12 | 40 | 80 | C | 90 | 90 | 80 | 90 | C | 90 | C |
| 257 | 1.12 | 20 | 50 | 80 | 60 | 70 | C | 70 | C | 60 | 90 |
| 258 | 1.12 | 30 | 40 | 60 | 30 | 50 | C | 80 | C | 80 | 90 |
| 259 | 1.12 | 20 | 0 | 0 | 0 | 0 | 30 | 70 | 30 | 40 | 40 |
| 260 | 1.12 | 20 | 30 | 50 | 60 | 80 | 60 | 40 | C | 60 | 90 |
| 261 | 11.21 | 20 | C | C | C | C | C | C | C | C | C |
| 262 | 1.12 | 20 | C | C | C | C | C | C | C | C | C |
| 263 | 1.12 | 30 | 30 | 70 | 70 | 70 | 80 | 60 | C | 60 | 90 |
| 264 | 1.12 | 40 | C | C | C | C | C | C | C | C | C |
| 265 | 1.12 | 20 | C | C | C | C | C | 90 | C | 90 | C |
| 266 | 1.12 | 20 | C | C | 90 | C | C | C | C | 90 | C |
| 267 | 1.12 | 10 | C | C | C | 90 | 90 | 90 | C | 90 | C |
| 268 | 1.12 | 20 | 80 | 90 | C | C | 90 | C | C | 50 | 90 |
| 269 | 1.12 | 30 | 90 | C | 70 | 90 | C | 90 | C | 90 | N |
| 270 | 1.12 | 60 | 90 | 90 | C | C | C | 90 | C | 90 | C |
| 271 | 1.12 | 20 | 70 | 40 | 60 | 50 | C | C | C | 50 | C |
| 272 | 1.12 | 30 | 60 | 40 | 50 | 60 | C | C | C | 60 | C |
| 273 | 1.12 | 20 | 70 | 40 | 80 | 50 | C | 60 | 90 | 60 | C |
| 274 | 1.12 | 0 | 40 | 50 | 50 | 30 | C | 60 | 70 | 40 | 80 |
| 275 | 1.12 | 20 | 40 | 80 | 70 | 50 | C | 80 | 90 | 40 | C |
| 276 | 1.12 | 20 | 50 | 50 | 30 | 80 | 90 | 30 | 90 | 50 | N |
| 277 | 1.12 | 20 | 90 | C | 90 | C | C | 80 | C | 60 | C |
| 278 | 1.12 | 40 | C | C | C | C | C | C | C | 90 | C |
| 279 | 11.21 | 50 | 10 | C | 80 | C | C | C | C | C | C |
| 280 | 11.21 | 60 | 0 | C | 40 | 80 | C | C | C | C | C |
| 281 | 1.12 | 0 | 0 | 0 | 0 | 0 | 30 | 30 | 30 | 30 | 30 |
|  | 1.12 | 0 | 0 | 0 | 0 | 0 | 50 | 40 | 20 | 0 | 60 |
| 282 | 1.12 | 10 | 0 | 20 | 0 | 30 | 70 | C | C | 10 | C |
| 283 | 1.12 | 0 | 10 | 50 | 30 | 40 | 90 | C | C | 50 | 90 |
| 286 | 1.12 | 20 | 0 | 30 | 0 | 50 | C | C | C | 30 | 90 |
| 289 | 1.12 | 20 | 10 | 50 | 20 | 60 | 90 | C | C | 40 | C |
| 290 | 1.12 | 20 | 0 | 40 | 10 | 50 | C | C | C | 60 | C |
| 291 | 1.12 | 30 | 0 | 30 | 20 | 20 | C | C | C | 40 | 90 |
| 292 | 1.12 | 10 | 0 | 0 | 0 | 40 | 60 | 80 | C | 20 | C |
| 293 | 1.12 | 20 | 0 | 20 | 0 | 60 | C | C | C | 10 | C |
| 294 | 1.12 | 0 | 20 | 30 | 20 | 20 | 80 | 50 | 50 | 20 | 30 |
|  | 1.12 | 0 | 0 | 0 | 0 | 0 | 90 | 80 | 80 | 0 | 0 |
| 295 | 1.12 | 30 | 60 | 80 | 30 | 50 | 90 | 70 | 90 | 80 | C |

TABLE 8-continued

POST EMERGENCE TESTS % PLANT INHIBITION

| Cpd. No. | | Rate kg/ha | Yens | Anbg | Sejg | Dobr | Bygr | Mogl | Cobu | Vele | Inmu | Wibw |
|---|---|---|---|---|---|---|---|---|---|---|---|---|
| 296 | | 1.12 | 20 | 0 | 10 | 10 | 10 | 90 | 90 | C | 30 | 90 |
| 297 | | 1.12 | 10 | 20 | 20 | 20 | 0 | 60 | 60 | 80 | 20 | C |
| 298 | | 1.12 | 20 | 30 | 30 | 30 | 20 | 90 | C | C | 60 | C |
| 299 | | 1.12 | 20 | 20 | 30 | 30 | 30 | C | C | C | 30 | 90 |
| 300 | | 1.12 | 40 | 0 | 60 | 20 | 80 | C | C | C | 30 | 90 |
| 301 | | 11.21 | 0 | 10 | 60 | 40 | 60 | 60 | 20 | 30 | 20 | 90 |
| 302 | | 1.12 | 10 | C | C | C | C | C | C | C | C | C |
| 304 | | 1.12 | 30 | 90 | C | 80 | C | 90 | 90 | C | C | C |
| 305 | | 1.12 | 10 | 80 | 70 | 90 | C | C | C | C | C | C |
| 306 | | 1.12 | 40 | C | C | C | C | C | C | C | C | C |
| 307 | | 1.12 | 20 | 90 | C | C | C | C | C | 90 | C | C |
| 308 | | 1.12 | 20 | C | C | C | C | 90 | 90 | C | 90 | C |
| 309 | | 1.12 | 60 | C | C | C | C | C | C | C | 90 | C |
| 310 | | 1.12 | 30 | 40 | 40 | 30 | 60 | C | 80 | 90 | 60 | C |
| 311 | | 1.12 | 40 | C | 80 | C | 90 | C | C | C | 80 | C |
| 312 | — | 11.21 | 10 | C | C | C | C | C | C | C | 90 | C |
| 313 | | 1.12 | 20 | C | 90 | C | C | C | 70 | C | 60 | C |
| 314 | | 1.12 | 30 | 90 | 90 | C | C | C | 90 | C | 90 | C |
| 316 | | 1.12 | 20 | 30 | 50 | 40 | 40 | 50 | 50 | 60 | 30 | C |
| 317 | = | 1.12 | 20 | 20 | 70 | 0 | 70 | C | C | C | 80 | C |
| 318 | = | 11.21 | 40 | 40 | C | 80 | 90 | C | C | C | 90 | C |
| 319 | = | 1.12 | 20 | 0 | 0 | 0 | 0 | C | C | C | 60 | C |
| 320 | = | 1.12 | 20 | 20 | 80 | 30 | 70 | C | C | C | 80 | C |
| 321 | | 1.12 | 0 | 0 | 20 | 20 | 20 | 30 | 60 | C | 30 | C |
| 322 | | 1.12 | 30 | 70 | 80 | 50 | 60 | 60 | 80 | 90 | 50 | C |
| 323 | | 1.12 | 20 | 50 | 30 | 20 | 30 | 80 | 70 | 90 | 30 | C |
| 324 | | 1.12 | 20 | C | C | C | C | 90 | C | C | 90 | 90 |
| 325 | — | 11.21 | 10 | C | C | C | 90 | C | C | C | 90 | C |
| 326 | | 11.21 | 20 | C | C | C | 90 | C | C | C | 50 | C |
| 327 | | 11.21 | 0 | 20 | 0 | 20 | 50 | 50 | 30 | 50 | 10 | 90 |
| 328 | | 1.12 | 0 | 40 | 50 | 20 | 60 | 50 | 80 | C | 30 | C |
| 330 | | 1.12 | 10 | 20 | 60 | 30 | 90 | 90 | 90 | C | 60 | C |
| 331 | | 1.12 | 30 | 80 | C | C | 90 | C | C | C | 90 | C |
| 332 | | 1.12 | 0 | 20 | 50 | 30 | 60 | 80 | 60 | C | 60 | C |
| 333 | | 1.12 | 0 | 30 | 40 | 30 | 80 | 60 | 50 | 80 | 40 | C |
| 334 | | 1.12 | 20 | 40 | 40 | 20 | 30 | 70 | 50 | 80 | 50 | 90 |
| 335 | | 1.12 | 20 | 30 | 90 | 80 | 80 | C | C | C | 90 | C |
| 336 | | 1.12 | 20 | 60 | 60 | 90 | 90 | C | 80 | C | 80 | C |
| 337 | | 1.12 | 20 | 20 | 60 | 80 | 50 | C | C | C | 60 | C |
| 338 | | 1.12 | 20 | 30 | 90 | 90 | 80 | C | C | C | 80 | C |
| 339 | | 1.12 | 0 | 0 | 0 | 30 | 40 | C | C | C | 50 | 90 |
| 340 | | 1.12 | 0 | 30 | 30 | 0 | 50 | C | C | C | 60 | C |
| 341 | | 1.12 | 20 | C | C | C | C | C | C | C | 90 | C |
| 342 | | 1.12 | 40 | 90 | 90 | C | C | C | C | C | 80 | C |
| 343 | | 11.21 | 20 | 30 | 60 | 40 | 40 | 80 | 80 | 80 | 60 | 80 |
| 344 | | 1.12 | 10 | 0 | 0 | 0 | 0 | 20 | 20 | 40 | 0 | 0 |
| 345 | | 1.12 | 0 | 0 | 0 | 0 | 20 | 40 | 20 | 30 | 20 | 20 |
| 346 | | 11.21 | 30 | 0 | 20 | 10 | 10 | 50 | 50 | C | 60 | 70 |
| 347 | | 11.21 | 0 | 50 | 70 | 30 | 80 | C | 80 | 90 | 60 | 60 |
| 348 | | 1.12 | 0 | 20 | 30 | 20 | 50 | C | 50 | 80 | 40 | 40 |
| 349 | | 1.12 | 20 | 20 | 0 | 20 | 20 | 30 | 40 | 60 | 30 | 60 |
| 352 | | 11.21 | 0 | 0 | 10 | 0 | 0 | 10 | 10 | 0 | 0 | 90 |
| 353 | | 11.21 | 10 | 90 | C | C | 90 | 90 | 80 | C | 90 | C |
| 354 | | 1.12 | 10 | 30 | 40 | 20 | 0 | 20 | 10 | 10 | 30 | 30 |
| 355 | | 11.21 | 10 | 10 | 40 | 10 | 60 | 90 | 40 | 50 | 40 | C |
| 356 | | 11.21 | 20 | 20 | 90 | 30 | 80 | 80 | 40 | 90 | 30 | C |
| 357 | | 11.21 | 0 | 0 | 10 | 10 | 10 | 20 | 10 | 30 | 10 | 20 |
| 358 | | 11.21 | 10 | 0 | 10 | 10 | 20 | 90 | 30 | 90 | 90 | 90 |
| 359 | | 1.12 | 0 | 0 | 0 | 0 | 0 | 0 | 10 | 10 | 0 | 70 |
| 360 | | 11.21 | 0 | 0 | 0 | 0 | 0 | 0 | 0 | 40 | 20 | 50 |
| 361 | | 11.21 | 10 | 0 | 0 | 0 | 10 | 0 | 10 | 10 | 0 | 30 |
| 362 | | 11.21 | 10 | 0 | 0 | 0 | 0 | 0 | 10 | 10 | 0 | 20 |
| 363 | | 11.21 | 0 | 0 | 30 | 30 | 20 | 90 | 30 | C | 30 | 90 |
| 364 | | 11.21 | 0 | 0 | 0 | 10 | 0 | 20 | 10 | 10 | 10 | 40 |
| 365 | | 11.21 | 0 | 30 | 80 | 30 | 30 | 70 | 30 | 90 | 20 | C |
| 366 | — | 11.21 | 10 | 30 | 60 | 60 | 80 | C | 40 | C | 60 | C |
| 367 | | 11.21 | 0 | 0 | 0 | 10 | 10 | 30 | 20 | 20 | 10 | N |
| 368 | | 11.21 | 0 | 0 | 0 | 0 | 0 | 0 | 10 | 10 | 10 | N |
| 369 | | 11.21 | 0 | 20 | 0 | 0 | 30 | 20 | 20 | 20 | 40 | 90 |
| 370 | | 11.21 | 0 | 10 | 10 | 10 | 40 | 20 | 20 | 30 | 30 | C |
| 371 | | 11.21 | 0 | 0 | 0 | 0 | 0 | 0 | 0 | 0 | 0 | 0 |
| 372 | | 11.21 | 0 | 0 | 0 | 0 | 20 | 30 | 20 | 20 | 20 | 60 |
| 373 | | 11.21 | 0 | 10 | 10 | 10 | 80 | 20 | 50 | 50 | 50 | 90 |
| 374 | | 11.21 | 0 | 10 | 40 | 10 | 40 | 90 | 20 | 60 | 80 | C |

TABLE 8-continued

POST EMERGENCE TESTS % PLANT INHIBITION

| Cpd. No. | Rate kg/ha | Yens | Anbg | Sejg | Dobr | Bygr | Mogl | Cobu | Vele | Inmu | Wibw |
|---|---|---|---|---|---|---|---|---|---|---|---|
| 375 | 11.21 | 0 | 0 | 10 | 0 | 10 | 20 | 10 | 10 | 20 | 30 |
| 376 | 11.21 | 0 | C | 60 | 50 | 50 | 60 | 80 | 90 | 90 | 90 |
| 377 | 11.21 | 20 | 90 | 30 | 90 | 60 | 90 | 90 | 90 | 90 | 90 |
| 378 | 11.21 | 0 | 0 | 0 | 0 | 10 | 40 | 20 | 20 | 90 | 90 |
| 379 | 11.21 | 0 | 0 | 10 | 10 | 30 | 40 | 40 | C | 20 | C |
| 380 | 11.21 | 0 | 0 | 30 | 20 | 20 | 40 | 30 | 50 | 30 | 70 |
| 381 | 1.12 | 0 | 0 | 0 | 0 | 0 | 20 | 20 | 0 | 20 | 0 |
| 382 | 11.21 | 0 | 0 | 20 | 0 | 30 | 30 | 30 | 60 | 50 | 90 |
| 383 | 11.21 | 0 | 0 | 20 | 0 | 0 | 30 | 20 | 40 | 20 | 10 |
| 384 | 11.21 | 0 | 0 | 0 | 0 | 0 | 0 | 20 | 30 | 20 | 50 |
| 385 | 11.21 | 0 | 30 | 0 | 0 | 20 | 40 | 30 | 40 | 50 | 40 |
| 386 | 11.21 | 0 | 0 | 0 | 0 | 0 | 80 | 60 | 50 | 50 | 50 |
| 387 | 11.21 | 0 | 0 | 0 | 0 | 30 | 10 | 10 | 30 | 30 | 50 |
| 388 | 11.21 | 0 | 0 | 0 | 0 | 30 | 10 | 10 | N | 10 | 20 |
| 389 | 11.21 | 10 | 90 | 90 | 80 | 90 | C | 50 | C | C | C |
| 390 | 11.21 | 10 | C | C | C | 90 | C | 60 | C | 90 | C |
| 391 | 1.12 | 20 | 30 | 30 | 10 | 60 | 90 | 20 | 30 | 20 | C |
| 392 | 1.12 | 10 | 40 | 60 | 40 | 90 | C | 40 | 80 | 40 | C |
| 393 | 1.12 | 20 | 0 | 20 | 10 | 20 | C | 90 | C | 0 | N |
| 394 | 1.12 | 10 | 80 | 90 | 40 | 90 | 80 | 30 | C | 60 | C |
| 395 | 1.12 | 10 | 20 | 60 | 30 | 40 | 50 | 20 | 60 | 30 | C |
| 396 | 11.21 | 10 | 30 | 30 | 20 | 20 | C | 20 | 90 | 40 | C |
| 397 | 1.12 | 0 | 20 | 60 | 10 | 70 | 40 | 20 | 40 | 30 | 80 |
| 398 | 1.12 | 0 | 0 | 0 | 0 | 0 | 0 | 0 | 0 | 0 | 0 |
| 399 | 1.12 | 30 | 50 | 40 | 60 | 70 | 50 | 70 | 90 | 60 | 90 |
| 400 | 11.21 | 30 | 0 | 20 | 0 | 30 | 90 | 30 | C | 90 | C |
| 401 | 1.12 | 10 | 40 | 40 | 30 | 50 | 60 | 30 | 90 | 30 | C |
| 402 | 1.12 | 0 | 20 | 20 | 20 | 20 | 80 | 50 | 90 | 30 | C |
| 403 | 11.21 | 30 | 50 | C | 90 | C | C | 90 | C | C | C |
| 404 | 11.21 | 10 | 60 | 90 | 90 | C | C | 90 | C | 90 | C |
| 405 | 11.21 | 20 | 20 | 50 | 30 | C | C | 90 | 90 | C | C |
| 406 | 11.21 | 10 | 0 | 30 | 10 | 20 | 30 | 30 | C | 40 | 90 |
| 407 | 11.21 | 40 | 20 | C | C | 90 | C | C | C | C | C |
| 408 | 11.21 | 20 | 40 | 70 | 30 | 60 | 50 | 50 | C | 80 | C |
|  | 11.21 | 0 | 40 | 40 | 0 | 40 | 40 | 80 | C | 80 | C |
| 409 | 11.21 | 0 | 0 | 30 | 0 | 40 | 60 | 90 | 70 | 30 | 70 |
|  | 11.21 | 0 | 40 | 70 | 20 | 40 | 70 | 80 | 70 | 60 | 80 |
| 410 | 11.21 | 0 | 0 | 80 | 60 | 0 | 50 | 60 | 90 | 60 | C |
| 411 | 1.12 | 0 | 0 | 50 | 0 | 50 | 60 | 20 | 90 | 30 | C |
|  | 1.12 | 30 | 40 | 80 | 50 | 80 | 80 | 40 | C | 60 | C |
| 412 | 1.12 | 0 | 0 | 20 | 20 | 20 | 40 | 30 | 50 | 20 | 50 |
| 413 | 11.21 | 0 | 20 | 50 | 30 | 70 | 80 | 60 | C | 40 | C |
| 414 | 11.21 | 10 | C | C | C | 90 | C | 40 | C | C | C |
| 415 | 1.12 | 30 | 50 | 30 | 30 | 80 | 50 | 40 | 90 | 30 | C |
| 416 | 1.12 | 20 | 40 | 60 | 30 | 30 | 50 | 50 | 80 | 40 | 60 |
| 417 | 1.12 | 20 | 20 | 50 | 30 | 40 | 60 | 60 | 90 | 50 | 80 |
| 418 | 1.12 | 0 | 0 | 0 | 20 | 30 | 30 | 0 | 60 | 0 | 70 |
|  | 1.12 | 0 | 0 | 20 | 20 | 20 | 40 | 30 | 30 | 30 | 60 |
| 419 | 1.12 | 0 | 20 | 70 | 0 | 50 | 50 | 50 | C | 40 | C |
| 420 | 1.12 | 0 | 10 | 0 | 0 | 40 | 50 | 40 | 60 | 60 | 90 |
| 421 | 11.21 | 30 | 80 | C | C | C | C | C | C | C | C |
| 422 | 11.21 | 0 | 50 | 90 | 60 | 80 | 70 | 70 | C | 80 | C |
| 423 | 11.21 | 0 | 0 | 0 | 0 | 0 | 30 | 40 | 30 | 20 | 90 |
| 424 | 11.21 | 0 | 0 | 20 | 0 | 10 | 10 | 40 | 90 | 20 | 90 |
| 425 | 11.21 | 0 | 0 | 0 | 0 | 0 | 40 | 40 | 80 | 60 | 60 |
|  | 11.21 | 0 | 0 | 0 | 0 | 0 | 50 | 50 | 60 | 50 | 50 |
| 426 | 11.21 | 0 | 0 | 0 | 0 | 0 | 40 | 30 | 30 | 20 | 40 |
| 427 | 11.21 | 0 | 0 | 0 | 0 | 0 | 0 | 10 | 0 | 0 | 0 |
| 428 | 11.21 | 0 | 0 | 0 | 20 | 20 | 90 | 40 | 80 | 60 | 60 |
| 429 | 11.21 | 40 | 20 | 50 | 0 | 40 | 20 | 20 | 90 | C | 60 |
| 430 | 11.21 | 0 | 30 | 60 | 20 | 30 | 50 | 50 | 90 | 30 | 80 |
| 431 | 11.21 | 0 | 0 | 0 | 0 | 0 | 10 | 20 | 10 | 20 | 10 |
| 432 | 11.21 | 0 | 20 | C | 10 | 20 | 40 | 20 | 60 | C | C |
| 433 | 11.21 | 0 | 0 | 0 | 0 | 0 | 0 | 0 | 0 | 0 | 0 |
| 435 | 11.21 | 0 | 40 | 80 | 20 | 60 | 80 | 60 | C | 0 | C |
| 436 | 11.21 | 0 | 0 | 50 | 0 | 0 | 20 | 30 | 20 | 40 | 0 |
| 437 | 11.21 | 0 | 0 | 30 | 0 | 0 | 60 | 30 | 40 | 30 | 50 |
|  | 11.21 | 0 | 0 | 20 | 0 | 0 | 40 | 20 | 30 | 0 | 50 |
| 438 | 1.12 | 30 | 50 | 40 | 20 | 30 | 70 | 60 | 80 | 30 | 90 |
| 439 | 1.12 | 20 | 0 | 50 | 20 | 30 | 40 | 60 | 80 | 30 | 80 |
| 440 | 11.21 | 20 | 60 | 60 | 30 | 50 | 90 | 70 | C | 70 | C |
| 441 | 1.12 | 10 | 30 | 40 | 20 | 30 | 80 | 80 | 80 | 40 | 80 |
| 442 | 11.21 | 0 | 30 | 50 | 20 | 50 | 90 | 50 | C | 70 | C |
| 443 | 1.12 | 20 | C | C | C | C | C | C | C | 90 | C |

TABLE 8-continued

POST EMERGENCE TESTS % PLANT INHIBITION

| Cpd. No. | Rate kg/ha | Yens | Anbg | Sejg | Dobr | Bygr | Mogl | Cobu | Vele | Inmu | Wibw |
|---|---|---|---|---|---|---|---|---|---|---|---|
| 444 | 1.12 | 40 | 0 | 60 | 0 | 20 | 80 | 80 | C | 30 | 30 |
| 445 | 1.12 | 40 | C | C | C | C | C | C | C | 90 | C |
| 446 | 1.12 | 40 | C | 90 | C | C | C | C | C | C | C |
| 447 | 1.12 | 20 | 40 | 30 | 60 | 80 | C | C | C | 90 | 70 |
| 448 | 1.12 | 20 | 30 | 40 | 20 | 50 | 90 | 70 | 80 | 20 | 40 |
| 449 | 1.12 | 10 | 30 | 50 | 40 | 60 | C | 80 | C | 10 | 40 |
| 450 | 1.12 | 10 | 40 | 40 | 30 | 40 | C | 80 | C | 20 | 50 |
| 451 | 1.12 | 20 | 0 | 0 | 0 | 20 | 40 | 40 | 50 | 20 | 50 |
| 452 | 1.12 | 10 | 20 | 40 | 0 | 40 | C | 80 | 70 | 60 | 90 |
| 453 | 1.12 | 20 | 40 | 40 | 20 | 50 | C | C | 80 | 30 | 50 |
| 454 | 1.12 | 30 | C | C | C | C | C | C | C | 90 | 80 |
| 455 | 1.12 | 20 | C | C | C | C | C | 80 | C | C | 90 |
| 456 | 1.12 | 50 | C | 90 | C | 80 | C | C | C | 70 | 90 |
| 457 | 1.12 | 10 | 70 | 90 | C | C | C | 90 | C | C | 60 |
| 458 | 1.12 | 20 | C | C | C | C | C | 80 | C | C | C |
| 459 | 1.12 | 20 | C | C | C | C | C | C | C | C | C |
| 460 | 1.12 | 20 | C | C | C | C | C | 80 | C | C | C |
| 461 | 1.12 | 20 | C | C | C | C | C | C | C | C | C |
| 462 | 11.21 | 0 | 30 | 50 | 20 | 10 | 40 | 30 | C | 40 | 90 |
| 463 | 1.12 | 40 | 30 | 60 | 90 | C | 90 | C | C | C | 90 |
| 464 | 1.12 | 20 | C | C | C | C | C | C | C | C | C |
| 465 | 11.21 | 50 | C | C | C | C | C | C | C | C | C |
| 466 | 11.21 | 40 | 40 | 80 | 50 | 70 | C | C | C | C | C |
| 467 | 11.21 | 40 | 80 | 80 | 40 | 90 | C | 80 | C | C | C |
| 468 | 1.12 | 30 | C | C | C | C | 90 | C | C | C | C |
| 469 | 1.12 | 20 | 10 | 30 | 20 | 80 | 80 | 80 | C | 60 | 90 |
| 470 | 1.12 | 0 | 0 | 0 | 0 | 0 | 20 | 20 | 0 | 0 | 0 |
| 471 | 11.21 | 40 | 90 | C | 70 | C | C | C | C | C | C |
| 472 | 11.21 | 10 | 20 | 50 | 20 | 30 | 60 | 50 | C | C | 70 |
| 473 | 11.21 | 0 | 0 | 0 | 10 | 0 | 60 | 30 | 50 | 30 | 50 |
| 474 | 11.21 | 20 | 80 | C | 90 | C | C | C | C | C | C |
| 475 | 11.21 | 10 | 20 | 70 | 0 | 60 | C | 30 | C | C | 90 |
| 476 | 11.21 | 0 | 0 | 0 | 0 | 0 | 0 | 0 | 0 | 0 | 0 |
| 477 | 11.21 | 0 | 0 | 0 | 0 | 0 | 0 | 0 | 0 | 0 | 0 |
| 478 | 11.21 | 0 | 20 | 20 | 20 | 20 | 70 | 70 | 90 | 40 | 80 |
| 479 | 11.21 | 0 | 0 | 0 | 0 | 0 | 10 | 10 | 0 | 0 | 0 |
| 480 | 11.21 | 0 | 0 | 0 | 0 | 0 | 30 | 0 | 20 | 50 | 0 |
| 481 | 11.21 | 10 | 50 | 90 | 40 | 50 | 90 | 40 | C | 40 | 90 |
| 482 | 11.21 | 20 | C | C | C | C | 90 | C | C | C | C |
| 484 | 5.61 | 0 | 0 | 0 | 0 | 30 | 50 | 20 | 60 | 50 | 80 |
| 485 | 11.21 | 0 | 0 | 20 | 0 | 20 | 60 | 60 | 80 | 30 | 90 |
| 486 | 1.12 | 30 | 30 | 10 | 20 | 40 | 80 | 70 | 40 | 40 | 80 |
| 487 | 11.21 | 0 | 0 | 0 | 0 | 0 | 20 | 30 | 70 | 20 | 80 |
| 489 | 11.21 | 10 | 10 | 10 | 0 | 0 | 20 | 20 | 90 | 0 | 30 |
| = | 1.12 | 0 | 0 | 0 | 0 | 0 | 20 | 0 | 0 | 20 | 0 |
| 490 | 1.12 | 20 | 60 | C | 90 | C | C | 70 | C | 80 | C |
| 491 | 11.21 | 0 | 0 | 30 | 0 | 40 | 50 | 50 | 60 | 30 | 70 |
| 492 | 11.21 | 0 | 0 | 0 | 20 | 0 | 10 | 0 | 0 | 0 | 0 |
| 493 | 11.21 | 0 | 0 | 20 | 0 | 50 | 40 | 40 | 50 | 20 | 60 |
|  | 11.21 | 0 | 0 | 0 | 0 | 30 | 0 | 0 | 20 | 20 | 40 |
| 494 | 11.21 | 0 | 0 | 0 | 0 | 0 | 20 | 20 | 20 | 0 | 10 |
| 495 | 1.12 | 0 | 0 | 0 | 0 | 20 | 20 | 20 | 40 | 50 | 50 |
| 496 | 1.12 | 0 | 0 | 0 | 0 | 0 | 0 | 10 | 10 | 30 | 0 |
| 497 | 11.21 | 0 | 0 | 0 | 0 | 0 | 0 | 0 | 0 | 20 | 40 |
| 498 | 11.21 | 0 | 0 | 0 | 0 | 0 | 80 | 50 | 90 | 30 | 90 |
| 499 | 11.21 | 10 | 0 | 10 | 0 | 30 | 20 | 20 | 20 | 20 | 40 |
| 501 | 11.21 | 0 | 50 | 60 | 30 | 30 | 80 | 30 | 80 | 30 | 50 |
|  | 1.12 | 0 | 0 | 0 | 0 | 0 | 0 | 0 | 0 | 0 | 0 |

~Wibw was generally thin.
=Cobu germination was erratic
−VOLATILE.
\TEST CONTAMINATION DUE TO VOLATILE COMPOUNDS.

TABLE 8A

POST EMERGENCE TESTS
% PLANT INHIBITION

| Cpd. No. | Rate kg/ha | Yens | Abg | Sejg | Dobr | Bygr | Mogl | Cobu | Vele | Inmu | Wibw |
|---|---|---|---|---|---|---|---|---|---|---|---|
| 89 | 11.21 | 0 | 10 | 70 | 10 | 20 | C | C | C | 80 | 80 |
| 93 | 1.12 | 0 | 10 | 40 | 50 | 70 | 60 | 70 | 90 | 60 | 90 |
| 98 | 1.12 | 0 | 70 | 90 | 90 | 80 | C | C | C | 80 | 80 |
| 136 | 1.12 | 10 | C | C | C | C | C | C | C | C | C |
| 139 | 1.12 | 10 | 90 | C | C | C | C | 90 | C | C | C |
| 140 | 1.12 | 10 | C | C | C | C | C | C | C | 90 | 90 |
| 141 | 1.12 | 0 | 90 | 90 | C | 70 | C | 90 | C | 80 | C |
| 178 | 1.12 | 0 | 90 | 70 | 90 | 70 | C | 90 | C | 70 | C |
| 198 | 1.12 | 0 | 50 | 70 | 70 | 50 | 90 | 70 | C | C | C |
| 203 | 11.21 | 0 | 20 | 60 | 30 | 50 | 60 | 60 | C | 60 | 90 |
| 205 | 11.21 | 0 | 40 | 70 | 50 | 10 | 80 | 60 | C | 60 | 90 |
| 251 | 1.12 | 10 | 80 | C | C | 90 | C | 90 | C | 70 | 90 |
| 252 | 1.12 | 20 | 90 | C | C | 90 | C | C | C | C | C |
| 285 | 1.12 | 40 | 30 | 50 | 40 | 70 | C | C | C | C | C |
| 287 | 1.12 | 10 | 0 | 80 | 10 | 70 | C | C | C | 20 | 90 |
| 288 | 1.12 | 10 | 0 | 20 | 0 | 50 | C | C | C | 90 | C |
| 303 | 11.21 | 70 | C | C | C | C | C | C | C | C | C |
| 315 | 11.21 | 20 | C | C | C | C | C | C | C | C | C |
| 329 | 1.12 | 0 | 90 | 90 | 90 | 90 | C | 90 | C | C | C |
| 350 | 1.12 | 30 | 20 | 70 | 0 | 60 | 90 | C | C | C | C |
| 351 | 1.12 | 30 | 30 | 60 | 40 | 70 | C | C | C | C | C |
| 488 | 1.12 | 0 | 90 | C | 90 | 90 | C | C | C | C | C |
| 500 | 11.21 | — | — | — | 0 | 0 | 0 | 0 | 0 | 0 | 0 |
|  | 11.21 | 0 | 50 | 90 | 70 | 90 | C | C | C | 90 | C |

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, and polymethylene bisnaphthalene sulfonate. Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 parts) of inert solid extender, all parts being by weight of the total composition. Where required, from about 0.1 to 2.0 parts of the solid inert extender can be replaced by a corrosion inhibitor or antifoaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring a nonaqueous solution of a water-insoluble active ingredient and an emulsification agent with water until uniform and then homogenizing to give stable emulsion of very finely divided particles. The resulting concentrated aqueous suspension is characterized by its extremely small particle size, so that when diluted and sprayed, coverage is very uniform. Suitable concentrations of these formulations contain from about 0.1–60%, preferably 5–50% by weight of active ingredient, the upper limit being determined by the solubility limit of active ingredient in the solvent. Concentrates are usually solutions of active ingredient in water-immiscible or partially water-immiscible solvents together with a surface active agent. Suitable solvents for the active ingredient of this invention include dimethylformamide, dimethylsulfoxide, N-methylpyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 5 to 94 parts solvent, all parts being be weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate extender, a surface active agent can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, sulfonylureas, carbamates, acetamides, acetanilides, uracils, acetic acid or phenol derivatives, thiolcarbamates, triazoles, azolopyrimidines, benzoic acid and its derivatives, nitriles, biphenyl ethers, nitrobenzenes and the like such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2-dioxide
3-Amino-1,2,4-triazole
6,7-Dihydrodipyrido(1,2-:2',1'-c)-pyrazidiinium salt
5-Bromo-3-isopropyl-6-methyluracil
1,1'-Dimethyl-4,4'-bypyridinium
2-(4-Isopropyl-4-methyl-5-oxo-2-imidazolin-2-yl)-3-quinolinecarboxylic acid
Isopropylamine salt of 2-(4-isopropyl-4-methyl-5-oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate

Ureas/Sulfonylureas

N-(4-Chlorophenoxy) phenyl-N,N-dimethylurea
N,N-dimethyl-N'-(3-chloro-4-methylphenyl) urea
3-(3,4-dichlorophenyl)-1,1-dimethylurea
1,3-Dimethyl-3-(2-benzothiazolyl) urea
3-(p-Chlorophenyl)-1,1-dimethylurea
1-Butyl-3-(3,4-dichlorophenyl)-1-methylurea
2-Chloro-N[(4-methoxy-6-methyl-l,3,5-triazin-2-yl) aminocarbonyl]-benzenesulfonamide
N-(2-methoxycarbonylphenyl sulfonyl()-N'-(4,6-bisdifluoromethoxypyrimidin-2-yl)urea
Methyl 2-(((((4,6-dimethyl-2-pyrimidinyl)amino)carbonyl)amino)sulfonyl) benzoate
Ethyl 1-[methyl 2-(((((4,6-dimethyl-2-pyrimidinyl)amino)carbonyl)amino)sulfonyl)] benzoate
Methyl-2 ((4,6-dimethoxy pyrimidin-2-yl) aminocarbonyl)amino sulfonyl methyl) benzoate
Methyl 2-(((((4-methoxy-6-methyl-l,3,5-triazin-2-yl)amino)carbonyl)amino)sulfonyl) benzoate

Carbamates/Thiolcarbamates

2-Chloroallyl diethyldithiocarbamate
S-(4-chlorobenzyl)N,N-diethylthiolcarbamate
Isopropyl N-(3-chlorophenyl) carbamate
S-2,3-dichloroallyl N,N-diisopropylthiolcarbamate
S-N,N-dipropylthiolcarbamate
S-propyl N,N-dipropylthiolcarbamate
S-2,3,3-trichloroallyl-N,N-diisopropylthiolcarbamate

Acetamides/Acetanilides/Anilines/Amides

2-Chloro-N,N-diallylacetamide
N,N-dimethyl-2,2-diphenylacetamide
N-(2,4-dimethylthien-3-yl)-N-(1-methoxyprop-2-yl)-2-chloroacetamide
N-(1H-pyrazol-1-ylmethyl-N-(2,4-dimethylthien-3-yl)-2-chloroacetamide
N-(1-pyrazol-1-ylmethyl)-N-(4,6-dimethoxypyrimidin-5-yl)-2-chloroacetamide
N-(2,4-dimethyl-5-[[[(trifluoromethyl)sulfonyl]amino]-phenyl]acetamide
N-Isopropyl-2-chloroacetanilide
N-Isopropyl-1-(3,5,5-trimethylcyclohexen-1-yl)-2-chloroacetamide
2',6'-Diethyl-N-(butoxymethyl)-2-chloroacetanilide
2',6'-Diethyl-N-(2-n-propoxyethyl)-2-chloroacetanilide
2',6'-Dimethyl-N-(1-pyrazol-1-ylmethyl)-2-chloroacetanilide
2',6'-Diethyl-N-methoxymethyl-2-chloroacetanilide
2'-Methyl-6'-ethyl-N-(2-methoxyprop-2-yl)-2-chloroacetanilide
2'-Methyl-6'-ethyl-N-(ethoxymethyl)-2-chloroacetanilide
α,α,α-Trifluoro-2,6-dinitro-N,N-dipropyl-p-toluidine
N-(1,1-dimethylpropynyl)-3,5-dichlorobenzamide

Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol
N-(phosphonomethyl)glycine and its salts
Butyl (R)-2-[4-[(5-(trifluoromethyl)-2-pyridinyl)oxy]phenoxy] propanoate

Ethers 2,4-Dichlorophenol-4-nitrophenyl ether
2-Chloro-δ,δ,δ-trifluoro-p-tolyl-3-ethoxy-4-nitrodiphenyl ether
5-(2-chloro-4-trifluoromethylphenoxy)-N-methylsulfonyl 2-nitrobenazmide
1'-(Carboethoxy) ethyl 5-[2-chloro-4-(trifluoromethyl)phenoxy]-2-nitrobenzoate

Miscellaneous 2,6-Dichlorobenzonitrile
Monosodium acid methanearsonate
Disodium methanearsonate
2-(2-chlorophenyl)methyl-4,4-dimethyl-3-isoxazolidinone
7-Oxabicyclo (2.2.1) heptane, 1-methyl-4-(1-methylethyl)-2-(2-methylphenylmethoxy)-, exo-
Glyphosate and salts thereof.

Fertilizers useful in combination with the active ingredients include, for example, ammonium nitrate, urea, potash and superphosphate. Other useful additaments include materials in which plant organisms take root and grow such as compost, manure, humus, sand and the like.

Herbicidal formulations of the types described above contemplated as within the purview of this invention are exemplified in several illustrative embodiments below.

|  |  | Weight Percent |
|---|---|---|
| I. Emulsifiable Concentrates | | |
| A. | Compound No. 308 | 11.0 |
|  | Free acid of complex organic phosphate or aromatic or aliphatic hydrophobe base (e.g., GAFAC RE-610, registered trademark of GAF Corp.) | 5.59 |
|  | Polyoxyethylene/polyoxypropylene block copolymer with butanol (e.g., Tergitol XH, registered trademark of Union Carbide Corp.) | 1.11 |
|  | Phenol | 5.34 |
|  | Monochlorobenzene | 76.96 |
|  |  | 100.00 |
| B. | Compound No. 261 | 25.00 |
|  | Free acid of complex organic phosphate of aromatic or aliphatic hydrophobe | 5.00 |

-continued

| | | Weight Percent |
|---|---|---|
| | base (e.g., GAFAC RE-610) Polyoxyethylene/polyoxypropylene block copolymer with butanol (e.g., Tergitol XH) | 1.60 |
| | Cyclohexanone | 4.75 |
| | Monochlorobenzene | 63.65 |
| | | 100.00 |
| C. | Compound No. 291 | 12.0 |
| | Free acid of complex organic phosphate or aromatic or aliphatic hydrophobe base (e.g., GAFAC RE-610, registered trademark of GAF Corp.) | 6.0 |
| | Polyoxyethylene/polyoxypropylene block copolymer with butanol (e.g., Tergitol XH, registered trademark of Union Carbide Corp.) | 1.5 |
| | Cyclohexanone | 5.5 |
| | Monochlorobenzene | 75.0 |
| | | 100.00 |
| D. | Compound of No. 229 | 20.0 |
| | Free acid of complex organic phosphate of aromatic or aliphatic hydrophobe base (e.g., GAFAC RE-610 | 5.00 |
| | Polyoxyethylene/polyoxypropylene block copolymer with butanol (e.g., Tergitol XH) | 2.0 |
| | Cyclohexanone | 5.0 |
| | Monochlorobenzene | 68.0 |
| | | 100.00 |
| E. | Compound No. 312 | 11.0 |
| | Free acid of complex organic phosphate or aromatic or aliphatic hydrophobe base (e.g. GAFAC RE-610, registered trademark of GAF Corp.) | 5.59 |
| | Polyoxyethylene/polyoxypropylene block copolymer with butanol (e.g., Tergitol XH, registered trademark of Union Carbide Corp.) | 1.11 |
| | Cyclohexanone | 5.34 |
| | Monochlorobenzene | 76.96 |
| | | 100.00 |
| F. | Compound No. 282 | 25.00 |
| | Free acid of complex organic phosphate of aromatic or aliphatic hydrophobe base (e.g., GAFAC RE-610 | 5.00 |
| | Polyoxyethylene/polyoxypropylene block copolymer with butanol (e.g., Tergitol XH) | 1.60 |
| | Cyclohexanone | 4.75 |
| | Monochlorobenzene | 63.65 |
| | | 100.00 |

II. Flowables

| | | Weight Percent |
|---|---|---|
| A. | Compound No. 261 | 25.0 |
| | Methyl cellulose | 0.3 |
| | Silica Aerogel | 1.5 |
| | Sodium lignosulfonate | 3.5 |
| | sodium N-methyl-N-oleyl taurate | 1.0 |
| | Water | 67.7 |
| | | 100.00 |
| B. | Compound No. 270 | 45.0 |
| | Methyl cellulose | .3 |
| | Silica aerogel | 1.5 |
| | Sodium lignosulfonate | 3.5 |
| | Sodium N-methyl-N-oleyl taurate | 1.0 |
| | Water | 47.7 |
| | | 100.00 |
| C. | Compound No. 294 | 30.0 |
| | Methyl cellulose | 0.3 |
| | Silica Aerogel | 1.5 |

-continued

| | | Weight Percent |
|---|---|---|
| | Sodium lignosulfonate | 3.5 |
| | Sodium N-methyl-N-oleyl taurate | 3.0 |
| | Water | 62.0 |
| | | 100.00 |
| D. | Compound No. 135 | 23.0 |
| | Methyl cellulose | 0.5 |
| | Silica Aerogel | 2.0 |
| | Sodium lignosulfonate | 3.5 |
| | Sodium N-methyl-N-oleyl taurate | 2.0 |
| | Water | 69.0 |
| | | 100.00 |
| E. | Compound No. 148 | 45.0 |
| | Methyl cellulose | .3 |
| | Silica aerogel | 1.5 |
| | Sodium lignosulfonate | 3.5 |
| | Sodium N-methyl-N-oleyl taurate | 1.0 |
| | Water | 47.7 |
| | | 100.00 |

III. Wettable Powders

| | | Weight Percent |
|---|---|---|
| A. | Compound No. 261 | 25.0 |
| | Sodium lignosulfonate | 3.0 |
| | Sodium N-methyl-N-oleyl-taurate | 1.0 |
| | Amorphous silica (synthetic) | 71.0 |
| | | 100.0 |
| B. | Compound No. 312 | 45.0 |
| | Sodium dioctyl sulfosuccinate | 1.25 |
| | Calcium lignosulfonate | 1.75 |
| | Amorphous silica (synthetic) | 52.0 |
| | | 100.0 |
| C. | Compound No. 237 | 10.0 |
| | Sodium lignosulfonate | 3.0 |
| | Sodium N-methyl-N-oleyl-taurate | 1.0 |
| | Kaolinite clay | 86.0 |
| | | 100.00 |
| D. | Compound No. 463 | 30.0 |
| | Sodium lignosulfonate | 3.0 |
| | Sodium N-methyl-N-oleyl-taurate | 1.0 |
| | Kaolin | 56.0 |
| | Amorphous silica (synthetic) | 10.0 |
| | | 100.0 |
| E. | Compound No. 446 | 75.0 |
| | Sodium dioctyl sulfosuccinate | 1.25 |
| | Calcium lignosulfonate | 1.75 |
| | Kaolin | 12.0 |
| | Amorphous silica synthetic | 10.0 |
| | | 100.00 |
| F. | Compound No. 482 | 15.0 |
| | Sodium lignosulfonate | 3.0 |
| | Sodium N-methyl-N-oleyl-taurate | 1.0 |
| | Amorphous silica, synthetic | 10.0 |
| | Kaolinite clay | 71.0 |
| | | 100.00 |

IV. Granules

| | | Weight Percent |
|---|---|---|
| A. | Compound No. 74 | 15.0 |
| | Dipropylene Glycol | 5.0 |
| | Granular attapulgite (20/40 mesh) | 80.0 |
| | | 100.0 |
| B. | Compound No. 390 | 15.0 |
| | Dipropylene Glycol | 5.0 |
| | Diatomaceous earth (20/40) | 80.0 |
| | | 100.0 |
| C. | Compound No. 399 | 1.0 |
| | Ethylene glycol | 5.0 |
| | Methylene blue | 0.1 |

|   |   | Weight Percent |
|---|---|---|
|   | Pyrophyllite | 93.9 |
|   |   | 100.0 |
| D. | Compound No. 393 | 5.0 |
|   | Ethylene Glycol | 5.0 |
|   | Pyrophyllite (20/40) | 90.0 |
|   |   | 100.0 |
| E. | Compound No. 312 | 15.0 |
|   | Propylene Glycol | 5.0 |
|   | Granular attapulgite (20/40 mesh) | 80.0 |
|   |   | 100.0 |
| F. | Compound No. 324 | 25.0 |
|   | Diatomaceous earth (20/40) | 75.0 |
|   |   | 100.0 |
| G. | Compound No. 261 | 5.0 |
|   | Ethylene glycol | 5.0 |
|   | Methylene blue | 0.5 |
|   | Pyrophyllite | 94.5 |
|   |   | 100.00 |
| H. | Compound No. 262 | 10.0 |
|   | Propylene Glycol | 5.0 |
|   | Pyrophyllite (20/40) | 85.0 |
|   |   | 100.0 |

V. Suspension Concentrates

|   |   | Weight Percent |
|---|---|---|
| A. | Compound No. 262 | 16.0 |
|   | Nonylphenol ethoxylate 9.5 mole EO Sterox NJ | 13.8 |
|   | Sodium lignosulfonate (Reax 88B) | 12.2 |
|   | Water | 58.0 |
|   |   | 100.0 |
| B. | Compound No. 446 | 32.5 |
|   | Potassium salt of napthalene sulfonate formaldehyde condensate (DAXAD 11 KLS) | 9.0 |
|   | Nonylphenol ethoxylate 10 mole EO (Igepal CO-660) | 9.0 |
|   | Water | 49.5 |
|   |   | 100.0 |
| C. | Compound No. 76 | 10.0 |
|   | Sodium dioctyl sulfosuccinate Aerosol OTB | 11.0 |
|   | Castor oil + 36 Ethylene oxide (FloMo 3G) | 11.0 |
|   | Water | 70.0 |
|   |   | 100.0 |
| D. | Compound No. 261 | 15.0 |
|   | Nonylphenol ethoxylate 9.5 mole EO Sterox NJ | 1.0 |
|   | Sodium lignosulfonate (Reax 88B) | 5.0 |
|   | Water | 79.0 |
|   |   | 100.0 |
| E. | Compound No. 290 | 30.0 |
|   | Potassium salt of napthalene sulfonate formaldehyde condensate (DAXAD 11 KLS) | 4.0 |
|   | Nonylphenol ethoxylate 10 mole EO (Igepal CO-660) | 2.0 |
|   | Water | 64.0 |
|   |   | 100.0 |
| F. | Compound No. 135 | 18.0 |
|   | Nonylphenol ethoxylate 9.5 mole EO Sterox NJ | 14.0 |
|   | Sodium lignosulfonate (Reax 88B) | 12.0 |
|   | Water | 56.0 |
|   |   | 100.0 |
| G. | Compound No. 148 | 34.0 |
|   | Potassium salt of napthalene sulfonate formaldehyde condensate (DAXAD aag) | 8.0 |
|   | Nonylphenol ethoxylate 10 mole EO (Igepal CO-660) | 10.0 |
|   | Water | 48.0 |
|   |   | 100.0 |
| H. | Compound No. 482 | 14.0 |
|   | Sodium dioctyl sulfosuccinate Aerosol OTB | 3.0 |
|   | Castor oil + 36 Ethylene oxide (FloMo 3G) | 3.0 |
|   | Water | 80.0 |
|   |   | 100.0 |

VI. Liquid Concentrates

|   |   | Weight Percent |
|---|---|---|
| A. | Compound No. 76 | 20.0 |
|   | Xylene | 80.0 |
|   |   | 100.0 |
| B. | Compound No. 229 | 10.0 |
|   | Xylene | 90.0 |
|   |   | 100.0 |
| C. | Compound No. 217 | 25.0 |
|   | Xylene | 75.0 |
|   |   | 100.0 |
| D. | Compound No. 482 | 15.0 |
|   | Xylene | 85.0 |
|   |   | 100.0 |

VII. Microcapsules

|   |   | Weight Percent |
|---|---|---|
| A. | Compound No. 135 encapsulated in a polyurea shell wall | 4.5 |
|   | Reax ® C-21 | 1.5 |
|   | NaCl | 5.0 |
|   | Water | 9.0 |
|   |   | 100.0 |
| B. | Compound No. 137 encapsulated in a polyurea shell wall | 20.0 |
|   | Reax ® 88B | 2.0 |
|   | $NaNO_3$ | 10.0 |
|   | Xylene | 30.0 |
|   | Water | 38.0 |
|   |   | 100.0 |
| C. | Compound No. 138 encapsulated in a polyurea shell wall | 4.8 |
|   | Reax ® 88B | 1.2 |
|   | $NaNO_3$ | 5.0 |
|   | Kerosene | 20.0 |
|   | Water | 69.0 |
|   |   | 100.0 |
| D. | Compound No. 148 encapsulated in a urea-formaldehyde polymer shell wall | 50.0 |
|   | Reax ® C-21 | 1.5 |
|   | NaCl | 8.5 |
|   | Petroleum oil (Aromatic 200) | 20.0 |
|   | Water | 20.0 |
|   |   | 100.0 |
| E. | Compound No. 229 encapsulated in a thiourea-formaldehyde shell wall | 30.0 |
|   | Reax ® C-21 | 2.0 |
|   | NaCl | 8.0 |
|   | Xylene | 30.0 |
|   | Water | 30.0 |
|   |   | 100.0 |
| F. | Compound No. 261 encapsulated in a polyurea shell wall | 7.5 |

-continued

|   |   | Weight Percent |
|---|---|---|
|   | Reax ® 88B | 1.5 |
|   | NaCl | 8.0 |
|   | Aromatic 200 | 30.0 |
|   | Water | 53.0 |
|   |   | 100.0 |
| G. | Compound No. 308 encapsulated in a melamine-formaldehyde co-polymeric shell wall | 9.0 |
|   | Reax ® 88B | 2.0 |
|   | NaNO$_3$ | 10.0 |
|   | Kerosene | 40.0 |
|   | Water | 39.0 |
|   |   | 100.0 |
| H. | Compound No. 446 encapsulated in a urea-formaldehyde polymeric shell wall | 15.0 |
|   | Reax ® 88B | 10.0 |
|   | NaNO$_3$ | 8.0 |
|   | Xylene | 42.0 |
|   | Water | 25.0 |
|   |   | 100.0 |
| I. | Compound No. 312 encapsulated in a polyurea shell wall | 22.0 |
|   | Reax ® 88B | 2.0 |
|   | NaCl | 8.0 |
|   | Xylene | 35.0 |
|   | Water | 33.0 |
|   |   | 100.0 |

When operating in accordance with the present invention, effective amounts of the compounds of this invention are applied to the soil containing the seeds, or vegetative propagules or may be incorporated into the soil media in any convenient fashion. The application of liquid and particulate solid compositions to the soil can be carried out by conventional methods, e.g., power duster, boom and hand sprayers and spray dusters. The compositions can also be applied from airplanes as a dust or a spray because of their effectiveness at low dosages. The exact amount of active ingredient to be employed is dependent upon various factors, including the plant species and stage of development thereof, the type and condition of soil, the amount of rainfall and the specific compounds employed. In elective pre-emergence application or to the soil, a dosage of from about 0.02 to about 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in *Webster's New International Dictionary*, Second Edition, Unabridged (1961). Thus, the term refers to any substance or medium in which vegetation may take root and grow, and includes not only earth but also compost, manure, muck, humus, loam, silt, mire, clay, sand and the like, adapted to support plant growth.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

We claim:

1. Process for the method of using

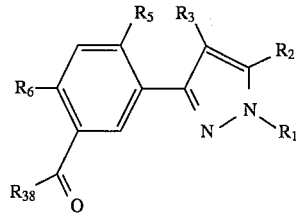

compounds according to Formula Y,

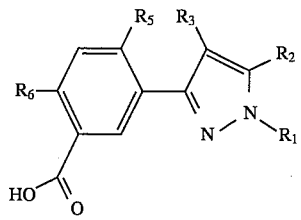

in the preparation of compounds of Formula Z

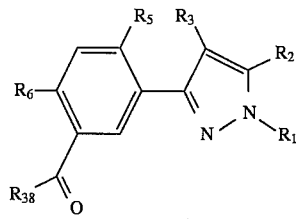

comprising the reaction of a compound of Formula Y with (1) a $C_{1-5}$ alcohol in the presence of a mineral acid or (2) a mineral acid followed by a $C_{1-5}$ alcohol, and thereafter isolating a compound of Formula Z, wherein $R_1$ is methyl;

$R_2$ is $C_{1-5}$ haloalkyl;

$R_3$ is halo;

$R_5$ is halo;

$R_6$ is halo; and $R_{38}$ is —$OC_{1-5}$ alkyl.

2. Process according to claim 1 wherein in Formula Z, $R_{38}$ is —$OCH_3(CH_2)_3$.

3. Process according to claim 2 wherein $R_2$ is trifluoromethyl, $R_5$ is fluoro, and $R_6$ is chloro.

* * * * *